United States Patent
Xie et al.

(10) Patent No.: US 10,265,298 B2
(45) Date of Patent: Apr. 23, 2019

(54) METHOD OF INCREASING THE BIOAVAILABILITY OF SILYBIN

(71) Applicant: Macau University of Science and Technology, Macau (CN)

(72) Inventors: Ying Xie, Macau (CN); Liang Liu, Macau (CN); Hua Zhou, Macau (CN)

(73) Assignee: Macau University of Science and Technology, Macau (CN)

( * ) Notice: Subject to any disclaimer, the term of this patent is extended or adjusted under 35 U.S.C. 154(b) by 0 days.

(21) Appl. No.: 15/682,564

(22) Filed: Aug. 22, 2017

(65) Prior Publication Data

US 2019/0060273 A1 Feb. 28, 2019

(51) Int. Cl.
| | |
|---|---|
| *A61K 31/357* | (2006.01) |
| *A61K 31/352* | (2006.01) |
| *A61K 9/20* | (2006.01) |
| *A61P 1/16* | (2006.01) |
| *A61K 9/00* | (2006.01) |

(52) U.S. Cl.
CPC .......... *A61K 31/357* (2013.01); *A61K 9/0053* (2013.01); *A61K 9/20* (2013.01); *A61K 31/352* (2013.01)

(58) Field of Classification Search
CPC ...... A61K 31/357; A61K 9/0053; A61K 9/20; A61K 31/352
See application file for complete search history.

(56) References Cited

U.S. PATENT DOCUMENTS

| | | | | |
|---|---|---|---|---|
| 2003/0215462 A1* | 11/2003 | Wacher | ................ | A61K 31/16 424/195.18 |
| 2010/0086627 A1* | 4/2010 | Zabrecky | ............. | A61K 31/198 424/746 |

OTHER PUBLICATIONS

Jiang et al. RSC Advances 2012, 2, 7948-7963.*
Van Zanden et al. Biochemical Pharmacology 2005, 69, 699-708.*
Ueng et al. Life Sciences 2000, 67, 2189-2200.*
Walsky et al. Drug Metabolsim and Disposition 2012, 40 (5), 1051-1065.*
Park, JD., et al. (1996). Effects of Ginseng Saponin on Modulation of Multidrug Resistance. Arch. Pharm. Res., 19(3), 213-218.
Shoba, G., et al. (1998). Influence of piperine on the pharmacokinetics of curcumin in animals and human volunteers. Planta Med., 64(4), 353-356.
Kesarwani, K. and Gupta, R. (2013). Bioavailability enhancers of herbal origin: an overview. Asian Pac J Trop Biomed., 3(4), 253-266.
Dudhatra, G.B., et al. (2012). A comprehensive review on pharmacotherapeutics of herbal bioenhancers. The Scientific World Journal., 1-33.
Ajazuddin, A.A., et al. (2014). Role of herbal bioactives as a potential bioavailability enhancer for Active Pharmaceutical Ingredients. Fitoterapia, 97, 1-14.
Flora, K., et al. (1998). Milk thistle (*Silybum marianum*) for the therapy of liver disease. Am J Gastroenterol., 93(2), 139-143.
Kim, N.C., et al. (2003). Complete isolation and characterization of silybins and isosilybins from milk thistle (*Silybum marianum*). Org Biomol Chem., 1(10), 1684-1689.
Abenavoli, L., et al. (2010). Milk thistle in liver diseases: past, present, future. Phytother Res., 24(10), 1423-1432.
Liang, L.D., et al. (2015). Ginsenoside-Rg5 induces apoptosis and DNA damage in human cervical cancer cells. Mol Med Rep., 11(2), 940-946.
Ahmed-Belkacem, A., et al. (2010). Silibinin and related compounds are direct inhibitors of hepatitis C virus RNA-dependent RNA polymerase. Gastroenterology, 138(3), 1112-1122.
Polyak, S.J., et al. (2010). Identification of hepatoprotective flavonolignans from silymarin. Proc Natl Acad Sci U S A., 107(13), 5995-5999.
Rutter, K., et al. (2011). Intravenous silibinin as 'rescue treatment' for on-treatment non-responders to pegylated interferon/ribavirin combination therapy. Antivir Ther., 16(8), 1327-1333.
Hawke, R.L., et al. (2010). Silymarin ascending multiple oral dosing phase I study in noncirrhotic patients with chronic hepatitis C. J Clin Pharmacol., 50(4), 434-449.
Zhang, J., et al. (2010). 20(S)-ginsenoside Rh2 noncompetitively inhibits P-glycoprotein in vitro and in vivo: a case for herb-drug interactions. Drug Metab Dispos., 38(12), 2179-2187.
Wen, Z., et al. (2008). Pharmacokinetics and metabolic profile of free, conjugated, and total silymarin flavonolignans in human plasma after oral administration of milk thistle extract. Drug Metab Dispos., 36(1), 65-72.
Lo, D., et al. (2014). Hepatoprotective effect of silymarin on di(2-ethylhexyl)phthalate (DEHP) induced injury in liver FL83B cells. Environmental Toxicology and Pharmacology, 38(1), 112-118.
Piscitelli, S.C., et al. (2002). Effect of milk thistle on the pharmacokinetics of indinavir in healthy volunteers. Pharmacotherapy: The Journal of Human Pharmacology and Drug Therapy, 22(5), 551-556.
Loguercio, C. and Festi, D., et al. (2011). Silybin and the liver: From basic research to clinical practice. World J Gastroenterol., 17(18), 2288-2301.
Fried, M., et al. (2012). Effect of silymarin (milk thistle) on liver disease in patients with chronic hepatitis C unsuccessfully treated with interferon therapy: a randomized controlled trial. JAMA, 308(3), 274-282.
Mateen, S., et al. (2013). Chemopreventive and anti-cancer efficacy of silibinin against growth and progression of lung cancer. Nutr Cancer, 65 Suppl 1, 3-11.

(Continued)

*Primary Examiner* — Irina Neagu

(74) *Attorney, Agent, or Firm* — Eagle IP Limited; Jacqueline C. Lui

(57) ABSTRACT

One example embodiment relates to a method of increasing bioavailability of silybin in a person. The method includes providing silybin and a flavonoid to the person, wherein the flavonoid is tangeretin or baicalein. Another example embodiment relates to a method of treating chronic liver disease in a person by administering silybin and a flavonoid to the person to treat the chronic liver disease.

12 Claims, 74 Drawing Sheets
(31 of 74 Drawing Sheet(s) Filed in Color)

(56) References Cited

OTHER PUBLICATIONS

Swift, B., et al. (2010). Sandwich-cultured hepatocytes: an in vitro model to evaluate hepatobiliary transporter-based drug interactions and hepatotoxicity. Drug Metab Rev, 42(3), 446-471.

Annaert, P.P., et al. (2001). P-glycoprotein-mediated in vitro biliary excretion in sandwich-cultured rat hepatocytes. Drug Metab Dispos, 29(10), 1277-1283.

Lee, J.K., et al. (2010). Sulindac and its metabolites inhibit multiple transport proteins in rat and human hepatocytes. J Pharmacol Exp Ther, 334(2), 410-418.

Liu, X. et al. (1999). Use of Ca2+ modulation to evaluate biliary excretion in sandwich-cultured rat hepatocytes. J Pharmacol Exp Ther., 259, 1592-1599.

Kobayashi, S., et al. (2013). Transport mechanisms for soy isoflavones and microbial metabolites dihydrogenistein and dihydrodaidzein across monolayers and membranes. Biosci Biotechnol Biochem, 77(11), 2210-2217.

Papaj, K., et al. (2014). Absorption and metabolism of biologically active genistein derivatives in colon carcinoma cell line (Caco-2). Acta Pol Pharm, 71(6), 1037-1044.

Li, Y. and Zhu, C. (2016). Enhanced hepatic-targeted delivery via oral administration using nanoliposomes fnctionalized with a novel DSPE-PEG-cholic acid conjugate. RSC Adv., 6, 28110-28120.

U.S. Department of Health and Human Services, F.D.A., Center for Drug Evaluation and Research (CDER), Guidance for industry, drug interaction studies—study design, data analysis, implications for dosing, and labeling recommendations. Feb. 2012. Clinical Pharmacology.

Xie, Y. et al. (2017). Role of UDP-Glucuronosyltransferase 1A1 in the Metabolism and Pharmacokinetics of Silymarin Flavonolignans in Patients with HCV and NAFLD. Molecules, 22(1), 1-15.

Miranda, S.R., et al. (2008). Hepatic metabolism and biliary excretion of silymarin flavonolignans in isolated perfused rat livers: role of multidrug resistance-associated protein 2 (Abcc2). Drug Metab Dispos, 36(11), 2219-2226.

Feng, S.L., et al. (2016). Tangeretin, a citrus pentamethoxyflavone, antagonizes ABCB1-mediated multidrug resistance by inhibiting its transport function. Pharmacol Res., 110, 193-204.

Ding, R.B., et al. (2012). Herbal medicines for the prevention of alcoholic liver disease: a review. J Ethnopharmacol, 144(3), 457-465.

Surai, P.F. (2015). Silymarin as a Natural Antioxidant: An Overview of the Current Evidence and Perspectives. Antioxidants, 4(1), 204-247.

Karimi, G., et al. (2011). "Silymarin", a Promising Pharmacological Agent for Treatment of Diseases. Iranian Journal of Basic Medical Sciences, 14(4), 308-317.

* cited by examiner

| | Papp$_{AP-BL}$(×10$^{-6}$) | | Papp$_{BL-AP}$(×10$^{-6}$) | | Efflux Ratio | |
|---|---|---|---|---|---|---|
| | SBa | SBb | SBa | SBb | SBa | SBb |
| 10μM Silybin | 0.47±0.03 | 0.45±0.02 | 1.69±1.08 | 2.05±0.08 | 5.05±0.23 | 4.61±0.34 |
| +MK 571 (50 μM) | 1.37±0.04 | 1.36±0.06 | 1.60±0.19 | 1.60±0.05 | 1.24±0.03 | 1.21±0.06 |
| +Ko143 (0.5 μM) | 0.63±0.05 | 0.56±0.04 | 1.48±0.76 | 1.76±0.22 | 3.08±0.44 | 3.15±0.20 |
| +QND (20μM) | 0.53±0.04 | 0.45±0.05 | 1.60±0.92 | 1.72±0.25 | 4.12±0.19 | 3.82±0.33 |
| +CsA (10μM) | 0.61±0.04 | 0.52±0.04 | 1.18±0.47 | 1.22±0.05 | 2.37±0.30 | 2.38±0.23 |

| | $P_{app\,AP\text{-}BL}(\times 10^{-6})$ | | $P_{app\,BL\text{-}AP}(\times 10^{-6})$ | | Efflux Ratio | |
|---|---|---|---|---|---|---|
| | SBa | SBb | SBa | SBb | SBa | SBb |
| 10μM SB | 1.52±0.39 | 1.23±0.14 | 7.10±0.77 | 6.45±0.26 | 4.87±1.21 | 5.26±0.40 |
| +MK(A) | 3.30±0.24 | 3.38±1.06 | 4.82±1.02 | 4.25±0.12 | 1.47±0.36 | 1.34±0.41 |
| +Fisetin(M) | 1.88±0.03 | 2.16±0.03 | 6.71±0.17 | 7.31±0.07 | 3.58±0.04 | 3.39±0.01 |
| +Curcumin(N) | 2.45±0.03 | 2.03±0.19 | 6.99±0.02 | 7.02±0.11 | 2.85±0.03 | 3.47±0.29 |
| +Myricetin(O) | 2.6±0.03 | 2.34±0.05 | 8.15±0.21 | 8.69±0.27 | 3.13±0.04 | 3.71±0.17 |
| +Genistein(P) | 2.28±0.20 | 2.02±0.36 | 7.15±0.02 | 6.20±0.29 | 3.15±0.27 | 3.16±0.75 |
| +Chrysin(Q) | 2.00±0.17 | 2.22±0.08 | 6.91±0.01 | 6.83±0.07 | 3.47±0.31 | 3.08±0.09 |
| +Quercetin(R) | 2.49±0.01 | 1.78±0.06 | 7.79±0.83 | 8.19±0.15 | 3.13±0.33 | 4.60±0.09 |
| +Kaempferol(S) | 2.12±0.07 | 2.19±0.43 | 7.35±0.24 | 7.40±0.05 | 3.47±0.18 | 3.48±0.73 |
| +Dihydromyricetin(T) | 1.57±0.03 | 1.45±0.10 | 7.12±0.19 | 7.15±0.19 | 4.53±0.10 | 4.93±0.21 |
| +Baicalin (U) | 2.01±0.24 | 1.66±0.07 | 7.33±0.27 | 6.66±0.92 | 3.67±0.33 | 3.99±0.39 |
| +Baicalein (V) | 2.63±0.12 | 2.7±0.050 | 6.54±0.69 | 6.84±0.93 | 2.48±0.15 | 2.53±0.31 |
| +Resveratrol(W) | 2.50±0.06 | 2.54±0.07 | 8.86±0.19 | 9.00±0.14 | 3.55±0.08 | 3.54±0.08 |
| +Tangeretin(X) | 3.40±0.23 | 3.11±0.23 | 6.05±0.3 | 5.42±0.27 | 1.79±0.21 | 1.75±0.14 |
| +Hesperidin(Y) | 1.86±0.02 | 1.40±0.04 | 8.70±0.17 | 6.87±0.17 | 4.68±0.13 | 4.91±0.22 |

| | Papp$_{AP-BL}$(×10$^{-6}$) | | Papp$_{BL-AP}$(×10$^{-6}$) | | Efflux Ratio | |
|---|---|---|---|---|---|---|
| | SBa | SBb | SBa | SBb | SBa | SBb |
| 10µM Silybin | 0.46±0.04 | 0.42±0.06 | 2.69±0.45 | 2.35±0.54 | 5.94±1.46 | 5.59±0.96 |
| +MK-571(A) | 1.25±0.13 | 1.15±0.20 | 1.58±0.41 | 1.63±0.16 | 1.25±0.19 | 1.44±0.24 |
| +Galangin(B) | 0.41±0.01 | 0.41±0.01 | 1.69±0.08 | 1.41±0.42 | 4.12±0.17 | 3.45±0.96 |
| +Biochanin A(C) | 0.43±0.01 | 0.43±0.01 | 1.72±0.10 | 1.73±0.20 | 3.98±0.26 | 4.07±0.52 |
| +Apigenin(D) | 0.30±0.01 | 0.36±0.01 | 1.61±0.07 | 1.58±0.10 | 5.36±0.21 | 4.44±0.31 |
| +Kaempferide(E) | 0.26±0.02 | 0.23±0.02 | 1.15±0.01 | 0.88±0.02 | 4.49±0.29 | 3.90±0.30 |
| +Isorhamnetin(F) | 0.27±0.02 | 0.27±0.03 | 1.17±0.05 | 1.06±0.04 | 4.40±0.27 | 4.00±0.36 |
| +Luteolin(G) | 0.83±0.02 | 0.85±0.02 | 2.48±0.14 | 2.11±0.11 | 3.00±0.12 | 2.47±0.08 |
| +Morin(H) | 0.80±0.01 | 0.66±0.11 | 2.87±0.17 | 2.21±0.19 | 3.57±0.23 | 3.41±0.44 |
| +Diosmetin(I) | 0.77±0.01 | 0.72±0.03 | 2.59±0.05 | 2.21±0.19 | 3.36±0.11 | 3.06±0.14 |
| +Myricetrin(J) | 0.56±0.02 | 0.57±0.01 | 1.75±0.20 | 1.78±0.05 | 3.15±0.45 | 3.12±0.02 |
| +Chelerythrine(K) | 0.78±0.01 | 0.87±0.01 | 1.76±0.04 | 1.73±0.08 | 2.27±0.06 | 1.99±0.11 |
| +(-)-ECG(L) | 0.69±0.05 | 0.75±0.07 | 1.60±0.16 | 1.83±0.03 | 2.32±0.18 | 2.45±0.23 |

Fig. 4B

| | Peak area of silybin glucuronides | | | Inhibitor Ratio (%) | |
|---|---|---|---|---|---|
| | AP-BL | BL-AP | | AP-BL | BL-AP |
| 10μM Silybin | 5944.42±2741.46 | 6006.76±2803.06 | | | |
| +MK-571(A) | 0 | 0 | | 100 | 100 |
| +Galangin(B) | 0 | 0 | | 100 | 100 |
| +Biochanin A(C) | 1358.77±18.59 | 615.24±38.60 | | 77.14±0.31 | 90.69±0.58 |
| +Apigenin(D) | 0 | 0 | | 100 | 100 |
| +Kaempferide(E) | 2288.36±94.46 | 679.63±33.21 | | 61.50±1.59 | 89.71±0.50 |
| +Isorhamnetin(F) | 1285.70±45.71 | 375.94±55.73 | | 78.37±0.77 | 94.31±0.84 |
| +Luteolin(G) | 0 | 0 | | 100 | 100 |
| +Morin(H) | 0 | 1071.23±236.36 | | 100 | 83.79±3.58 |
| +Diosmetin(I) | 0 | 0 | | 100 | 100 |
| +Myricetin(J) | 5271.37±151.21 | 7186.49±40.77 | | 11.15±2.54 | 0 |
| +Chelerythrine(K) | 4434.28±450.16 | 4499.25±502.52 | | 25.40±7.58 | 31.90±7.61 |
| +(-)-ECG(L) | 3579.43±203.24 | 5203.57±258.02 | | 39.79±3.42 | 21.24±3.91 |

Fig. 7A

| | Peak area of silybin glucuronides | | | Inhibitor Ratio (%) | |
|---|---|---|---|---|---|
| | AP-BL | BL-AP | AP-BL | BL-AP |
| 10μM SB | 10245.94±224.94 | 8302.27±558.28 | - | - |
| +MK(A) | 0 | 0 | 100 | 100 |
| +Fisetin(M) | 4083.36±329.35 | 2251.82±1023.8 | 60.15±3.21 | 72.88±1.23 |
| +Curcumin(N) | 3216.57±341.66 | 1775.23±17.87 | 68.61±3.33 | 78.62±0.22 |
| +Myricetin(O) | 6581.34±156.89 | 3587.87±55.77 | 35.77±1.53 | 55.69±2.21 |
| +Genistein(P) | 6267.96±29.57 | 5094.81±249.34 | 38.82±0.29 | 37.15±0.91 |
| +Chrysin(Q) | 3696.16±113.92 | 2215.03±184.58 | 63.93±1.11 | 72.69±1.34 |
| +Quercetin(R) | 2350.15±37.53 | 1103.85±128.53 | 77.06±0.56 | 86.4±1.12 |
| +Kaempferol(S) | 3400.74±122.29 | 2329.54±2.16 | 66.81±1.19 | 71.24±0.96 |
| +Dihydromyricetin(T) | 4873.60±159.66 | 4048.53±216.65 | 52.43±1.56 | 49.97±4.40 |
| +Baicalin(U) | 4380.52±9.29 | 2948.13±112.23 | 57.25±0.09 | 63.63±0.13 |
| +Baicalein(V) | 0 | 0 | 100 | 100 |
| +Resveratrol(W) | 565.53±16.07 | 750.45±38.52 | 94.48±0.16 | 90.73±0.79 |
| +Tangeretin(X) | 6903.21±958.13 | 5716.27±234.27 | 32.62±9.35 | 29.48±0.46 |
| +Hesperidin(Y) | 7458.56±201.07 | 3614.84±21.88 | 27.2±1.96 | 55.37±1.81 |

Fig. 7B

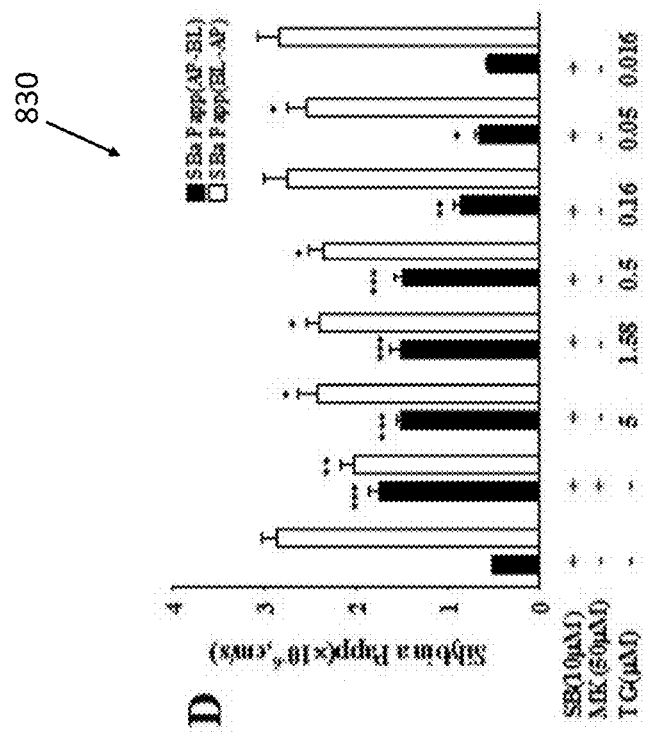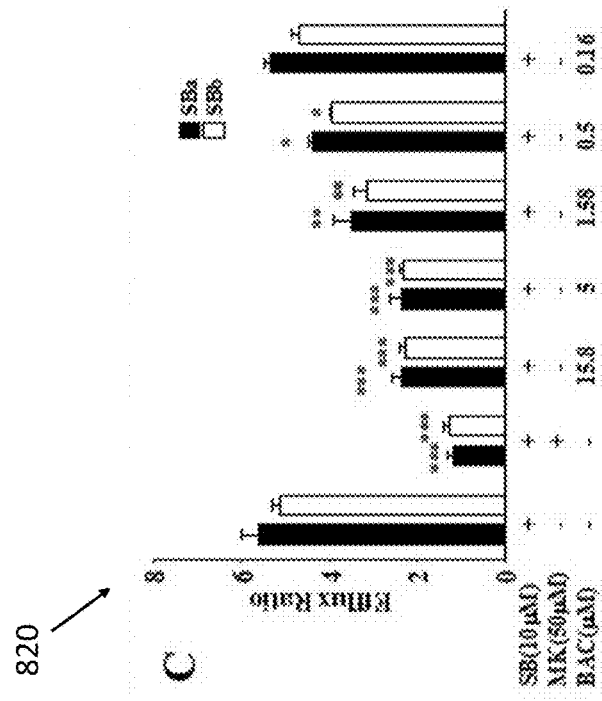

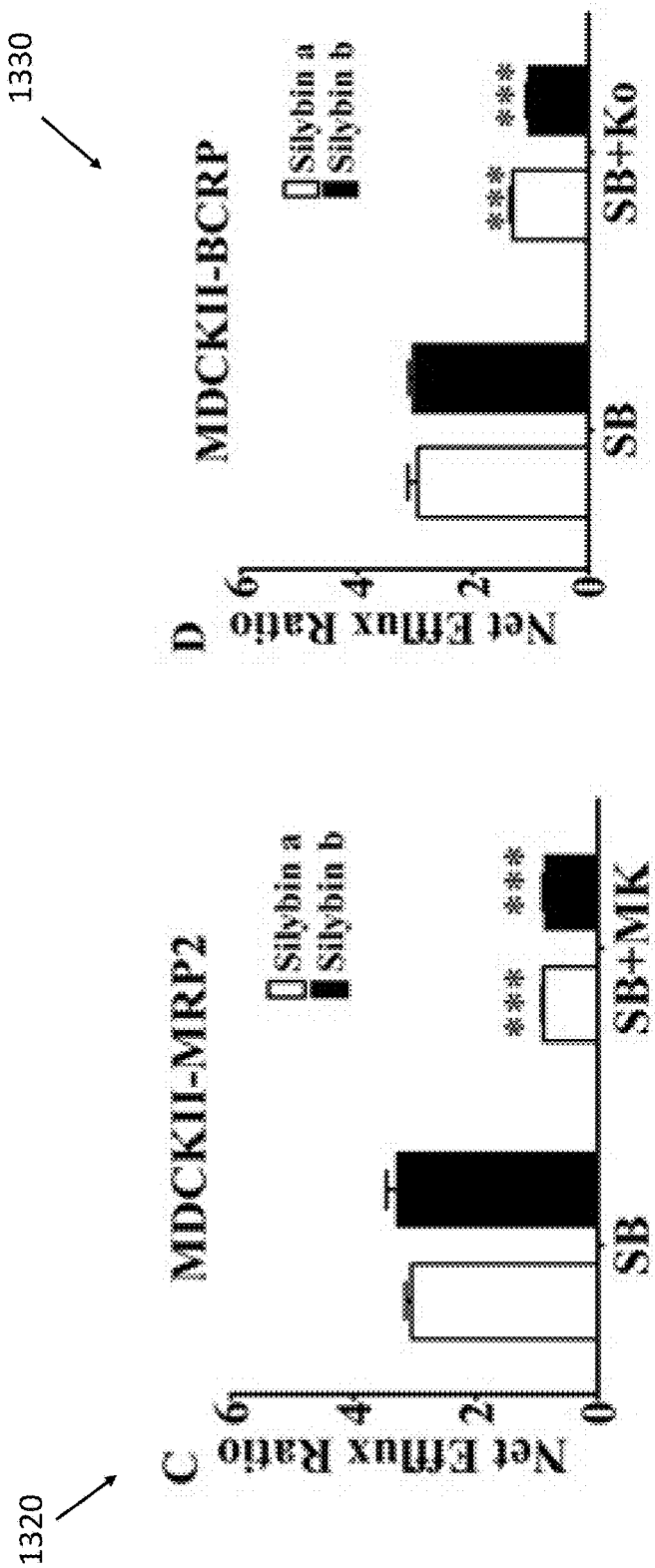

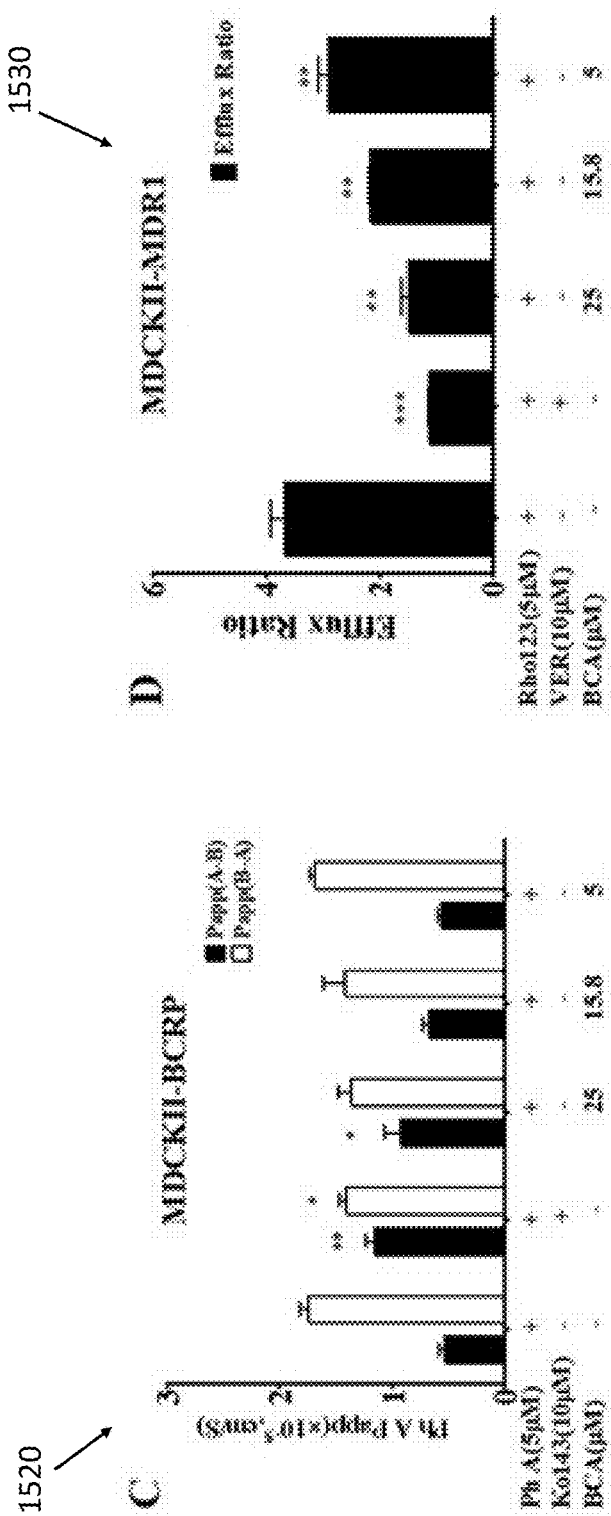

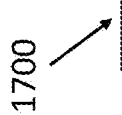

| Parameters[a] | Without baicalein | | With baicalein | |
|---|---|---|---|---|
| | Free SBa | Free SBb | Free SBa | Free SBb |
| AUC$_{(0-t)}$ (ng/ml*h) | 80±9 | 72±14 | 1550±157*** | 393±35*** |
| AUC$_{(0-\infty)}$ (ng/ml*h) | 124±44 | 212±210 | 1855±675*** | 557±71** |
| MRT$_{(0-t)}$(h) | 3.29±0.67 | 3.93±0.53 | 4.00±0.59 | 3.89±0.39 |
| t 1/2z(h) | 4.43±1.94 | 5.39±2.27 | 3.82±3.61 | 5.41±2.30 |
| T$_{max}$(h) | 0.75±0.50 | 2.00±3.35 | 1.00±0.32 | 0.67±0.38 |
| CL$_z$/F(ml/h/kg) | 89.43±32.27 | 68.01±54.14 | 5.83±1.47*** | 18.20±2.46*** |
| C$_{max}$(ng/ml) | 26±13 | 16±5 | 418±80*** | 136±30*** |

[a]: $C_{max}$: Maximum plasma concentration; $T_{max}$: Time to reach maximum plasma concentration; $T_{1/2A\ phase}$: Half-life of absorption phase; CL/F: Oral clearance; AUC$_{0-t}$: Area under the concentration-time curve from zero up to a definite time t; AUC$_{0-\infty}$: Area under the concentration-time curve from zero up to infinite time. [b]: Data are expressed as the mean ± SD. of 6 rats. *, $P<0.05$; , $P<0.01$; *, $P<0.01$ VS only administrate with silybin.

Fig. 17

| Parameters [a] | Without baicalein | | | | With baicalein | | | |
|---|---|---|---|---|---|---|---|---|
| | Total SBa | Total SBb | Total SBa | Total SBb |
| $AUC_{(0-t)}$ (ng/ml*h) | 3336±424 | 8133±1597 | 12450±2553*** | 15683±2695*** |
| $AUC_{(0-\infty)}$ (ng/ml*h) | 3494±453 | 8512±1675 | 14475±4646*** | 15882±2658*** |
| $MRT_{(0-t)}$ (h) | 3.49±0.49 | 3.40±0.68 | 3.79±0.20 | 2.74±0.09 |
| $t_{1/2}$ (h) | 2.77±0.96 | 2.54±0.66 | 4.14±2.58 | 1.82±0.52 |
| $T_{max}$ (h) | 1.40±0.42 | 1.10±0.22 | 1.83±0.26 | 1.83±0.26 |
| $CL_{z/F}$ (ml/h/kg) | 2.90±0.41 | 1.21±0.25 | 0.75±0.21 | 0.65±0.11 |
| $C_{max}$ (ng/ml) | 1109±158 | 2478±284 | 2978±632*** | 4911±804*** |

[a]: $C_{max}$: Maximum plasma concentration; $T_{max}$: Time to reach maximum plasma concentration; $T_{1/2\,A\,phase}$: Half-life of absorption phase; CL/F: Oral clearance; $AUC_{0-t}$: Area under the concentration-time curve from zero up to a definite time t; $AUC_{0-\infty}$: Area under the concentration-time curve from zero up to infinite time. [b]: Data are expressed as the mean ± SD. of 6 rats. *, $P<0.05$; , $P<0.01$; *, $P<0.01$ VS only administrate with silybin.

Fig. 18

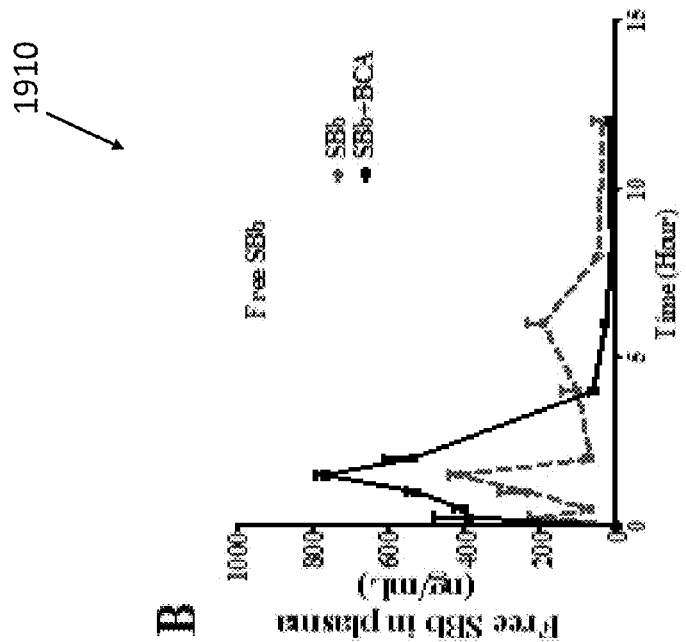
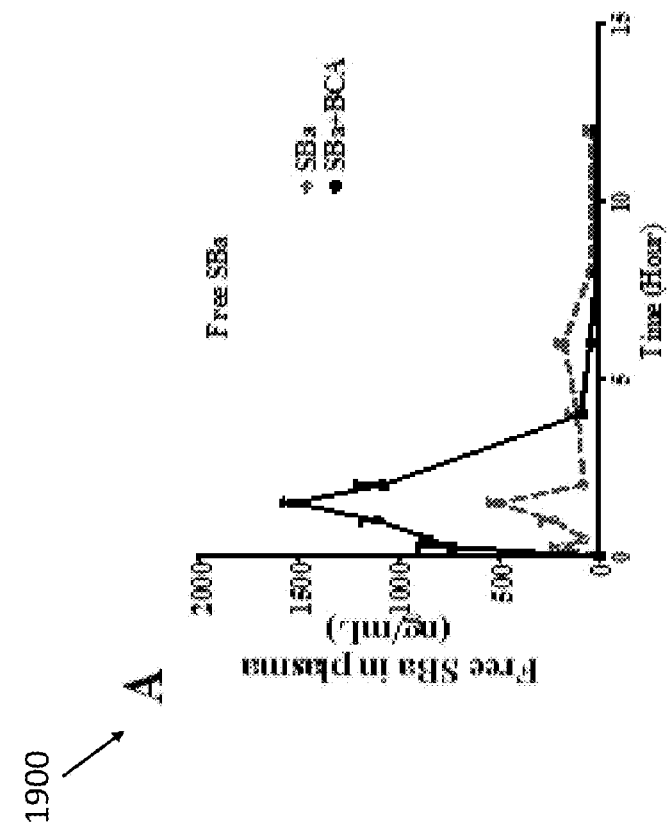
Fig. 19A
Fig. 19B

| Parameters [a] | Without baicalein | | With baicalein | |
| --- | --- | --- | --- | --- |
| | Free SBa | Free SBb | Free SBa | Free SBb |
| $AUC_{(0-t)}$ (ng/ml*h) | 1292±341 | 1195±302 | 3534±344*** | 1808±225** |
| $AUC_{(0-\infty)}$ (ng/ml*h) | 2305±1147 | 2087±931 | 3599±410* | 1812±223 |
| MRT (0-t)(h) | 4.1±0.9 | 4.21±0.98 | 1.9±0.2 | 2.1±0.3 |
| $t_{1/2z}$(h) | 1.5±0.2 | 1.7±0.3 | 1.6±2.3 | 1.34±0.53 |
| T max(h) | 1.50±0 | 1.50±0 | 1.5±0 | 1.29±0.51 |
| CLz/F(ml/h/kg) | 25.0±8.5 | 27.0±8.6 | 14.0±1.6 | 17.9±3.7 |
| C max(ng/ml) | 507±114 | 412±69 | 1526±126*** | 915±150*** |

[a]: $C_{max}$: Maximum plasma concentration; $T_{max}$: Time to reach maximum plasma concentration; $T_{1/2\ D/A\ phase}$: Half-life of distribution phase; $T_{1/2\ A\ phase}$: Half-life of absorption phase; CL/F: Oral clearance; $AUC_{0-t}$: Area under the concentration-time curve from zero up to a definite time t; $AUC_{0-\infty}$: Area under the concentration-time curve from zero up to infinite time.

[b]: Data are expressed as the mean ± SD. of 6 rats.

*, $P<0.05$; , $P<0.01$; *, $P<0.01$ vs only administrate with silybin

Fig. 20

| Parameters [a] | Without baicalein | | With baicalein | |
|---|---|---|---|---|
| | Total SBa | Total SBb | Total SBa | Total SBb |
| AUC$_{(0-t)}$ (ng/ml*h) | 12450±2553 | 53184±7340 | 25921±2277*** | 97584±23856** |
| AUC$_{(0-\infty)}$ (ng/ml*h) | 14475±4645 | 54680±7924 | 26906±3129*** | 98637±24179** |
| MRT$_{(0-t)}$ (h) | 3.7±0.4 | 3.7±0.3 | 3.8±0.2 | 3.2±0.2 |
| t$_{1/2}$ (h) | 2.1±0.9 | 1.9±0.9 | 4.1±2.6 | 1.6±0.2 |
| T$_{max}$ (h) | 1.3±0.3 | 1.6±0.4 | 1.8±0.3 | 1.8±0.3 |
| CL$_{z/F}$ (ml/h/kg) | 1.9±0.2 | 0.9±0.1 | 0.8±0.2 | 0.6±0.2 |
| C$_{max}$ (ng/ml) | 6427±2284 | 9668±2134 | 18194±3634** | 23522±3643*** |

[a]: $C_{max}$: Maximum plasma concentration; $T_{max}$: Time to reach maximum plasma concentration; $T_{1/2\ D/A\ phase}$: Half-life of distribution phase; $T_{1/2\ A\ phase}$: Half-life of absorption phase; CL/F: Oral clearance; AUC$_{0-t}$: Area under the concentration-time curve from zero up to a definite time t; AUC$_{0-\infty}$: Area under the concentration-time curve from zero up to infinite time.
[b]: Data are expressed as the mean ± SD. of 6 rats.
*, $P<0.05$; , $P<0.01$; *, $P<0.01$ vs only administrate with silybin

Fig. 21

| Parameters [a] | Without Tangeretin | | With Tangeretin [b] | |
|---|---|---|---|---|
| | Free SBa | Free SBb | Free SBa | Free SBb |
| AUC(0-t) (ng·h/ml) | 64±13 | 65±16 | 199±44** | 221±57** |
| AUC(0-8)(ng·h/ml) | 98±53 | 90±55 | 292±103* | 366±218* |
| MRT (h) | 3.80±0.49 | 4.06±0.50 | 1.62±0.36 | 1.47±0.39 |
| Tmax (h) | 0.5±0 | 1.33±0.76 | 0.25±0 | 0.25±0 |
| t1/2 (h) | 2.72±0.98 | 1.53±0.18 | 4.45±1.52 | 4.23±2.03 |
| CL/F(ml/h/kg) | 122.72±59.72 | 137.49±69.04 | 37.78±12.31 | 36.18±20.09 |
| Cmax(ng/ml) | 15±1 | 16±1 | 97±29*** | 107±42** |

[a]: $C_{max}$: Maximum plasma concentration; $T_{max}$: Time to reach maximum plasma concentration; $T_{1/2}$: Half-life; MRT: Mean residence time; CL/F: Oral clearance; $AUC_{0-t}$: Area under the concentration-time curve from zero up to a definite time t; $AUC_{0-\infty}$: Area under the concentration-time curve from zero up to infinite time.
[b]: Data are expressed as the mean ± S.D. of 6 rats.
*, P<0.05; , P<0.01; *, P<0.01 vs only administrate with silybin.

Fig. 22

| Parameters[a] | Without Tangeretin | | | | With Tangeretin | | | |
|---|---|---|---|---|---|---|---|---|
| | Total SBa | Total SBb | Total SBa | Total SBb | Total SBa | Total SBb | Total SBa | Total SBb |
| AUC(0-t) (ng·h/ml) | 3255±738 | 8778±1445 | | | 7371±1066*** | 12731±2534* | | |
| AUC(0-8)(ng·h/ml) | 3450±642 | 9228±1572 | | | 7758±1078*** | 13096±2520* | | |
| MRT (h) | 3.15±0.28 | 3.01±0.26 | | | 3.17±0.47 | 2.62±0.22 | | |
| $T_{max}$ (h) | 1.33±0.29 | 1.33±0.29 | | | 0.75±0.42 | 0.67±0.26 | | |
| $t1/2$ (h) | 2.98±1.29 | 2.80±0.77 | | | 3.03±0.58 | 2.30±1.10 | | |
| CL/F (ml/h/kg) | 2.96±0.51 | 1.11±0.19 | | | 1.31±0.19 | 0.78±0.13 | | |
| $C_{max}$(ng/ml) | 952±261 | 2436±341 | | | 2528±281*** | 4366±478*** | | |

Fig. 23

[a]: $C_{max}$: Maximum plasma concentration; $T_{max}$: Time to reach maximum plasma concentration; $T_{1/2}$: Half-life; MRT: Mean residence time; CL/F: Oral clearance; $AUC_{0-t}$: Area under the concentration-time curve from zero up to a definite time t; $AUC_{0-\infty}$: Area under the concentration-time curve from zero up to infinite time.
[b]: Data are expressed as the mean ± S.D. of 6 rats.
*, $P<0.05$; , $P<0.01$; *, $P<0.01$ vs only administrate with silybin.

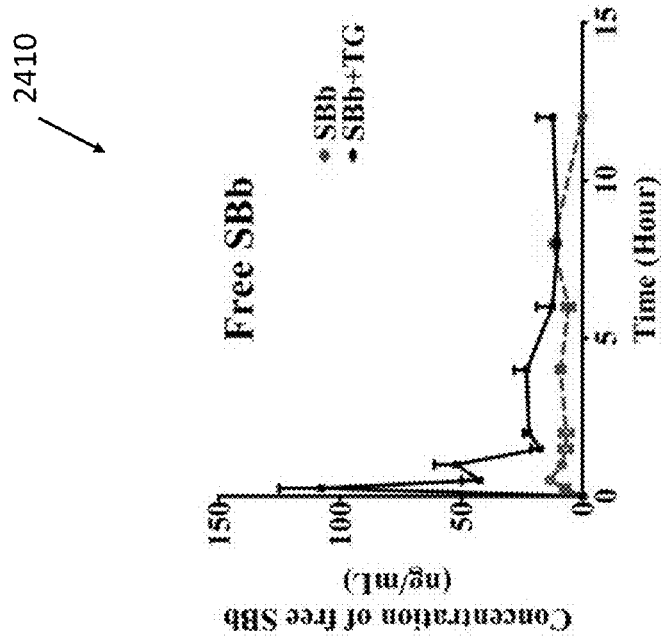
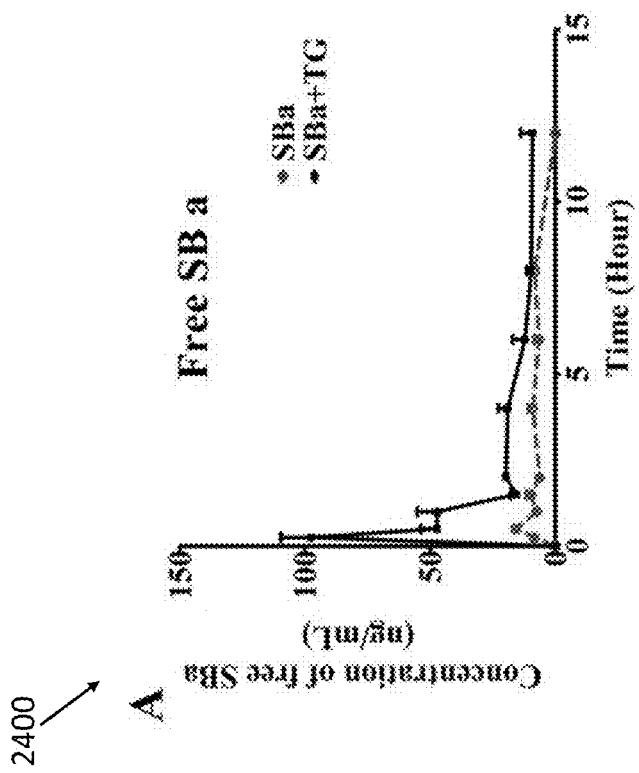
Fig. 24B
Fig. 24A

| | Liver weight (g) | Body weight (g) | Liver weight/Body weight |
|---|---|---|---|
| Control | 6.41±0.17 | 219.0±12.25 | 0.029±0.002 |
| Model | 10.51±0.90### | 221.8±8.26 | 0.048±0.005## |
| SB100 mg/kg | 9.00±1.28* | 222.0±19.99 | 0.041±0.005* |
| SB100 mg/kg +TG100 mg/kg | 7.55±0.71** a | 221.3±19.87 | 0.034±0.006** a |
| SB50 mg/kg +TG50 mg/kg | 7.69±0.38** | 205.0±13.23 | 0.038±0.003* |
| TG100mg/kg | 9.48±1.91 | 223.3±10.11 | 0.042±0.008 |

Note: Values are means± S.D., n=6 in each group.
### P<0.001, vs. normal group, * P<0.05, ** P<0.01 vs model group, a P<0.05, vs. silybin (100 mg/kg) group.

Fig. 28

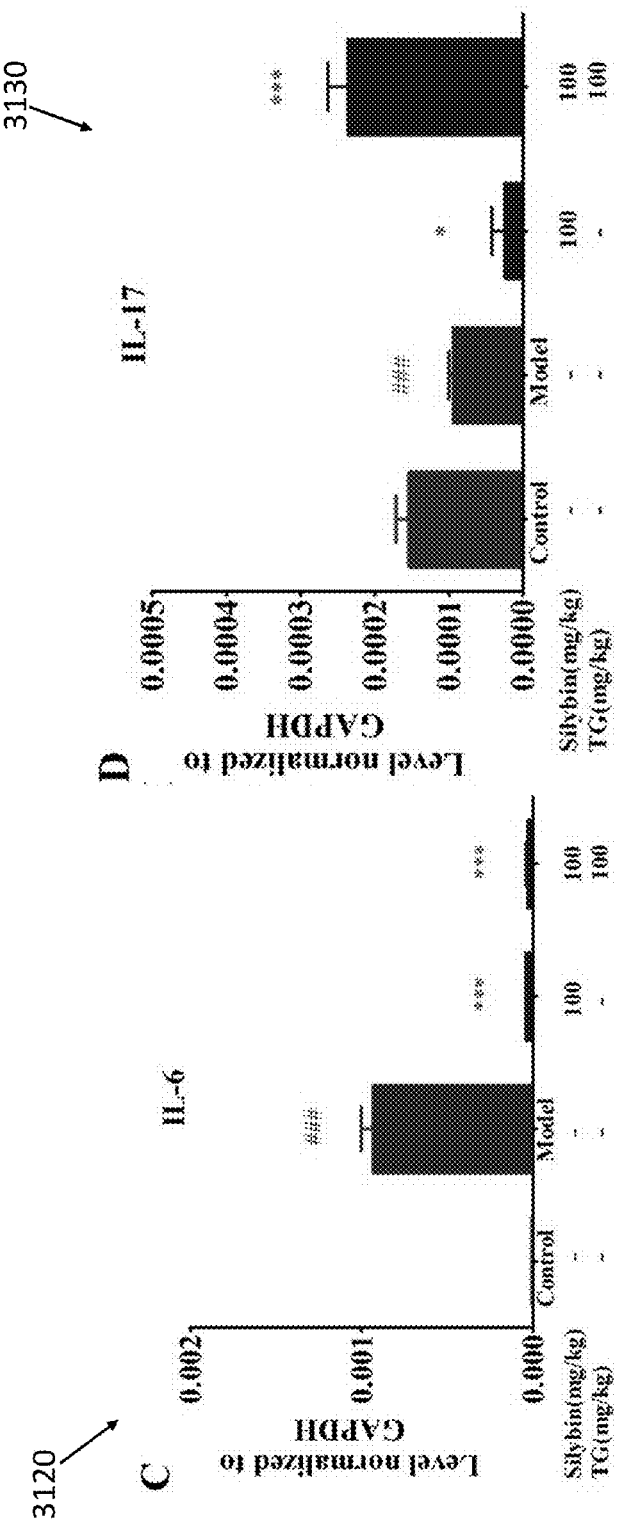

|  | Necrosis | Haemorrhage | Inflammation | Steatosis |
|---|---|---|---|---|
| Control | 0±0 | 0±0 | 0±0 | 0±0 |
| Model | 3.50±0.58 | 2.25±0.50 | 2.25±0.50 | 2.25±0.50 |
| Silybin(100mg/kg) | 2.25±0.50* | 1.50±0.58 | 1.75±0.50 | 1.25±0.50 |
| Silybin(100mg/kg)+TG(100mg/kg) | 1.50±0.58** | 0.75±0.50** | 1.25±0.50* | 1.00±0.82* |
| Silybin(50mg/kg)+TG(50mg/kg) | 2.00±0.82* | 1.25±0.50* | 1.50±0.58 | 1.50±0.58 |
| TG (100mg/kg) | 2.75±0.96 | 1.75±0.50 | 1.75±0.50 | 1.50±0.58 |

Statistically significant differences with respect to the model are expressed as * $P<0.05$,  $P<0.01$, and * $P<0.001$.

Fig. 33

| | Body weight(g) | Liver weight(g) | Liver / body weight ratio (%) |
|---|---|---|---|
| Control | 20.88±0.62 | 0.83±0.04 | 3.97±0.28 |
| Model | 12.29±1.04 | 0.64±0.06### | 5.23±0.59### |
| SB 300 mg/kg | 11.06±0.67 | 0.52±0.03 | 4.73±0.20* |
| SB 150 mg/kg | 10.99±0.52 | 0.59±0.04 | 5.17±0.33 |
| TG 150mg/kg | 11.91±0.48 | 0.65±0.07 | 5.41±0.51 |
| (SB+TG)-L | 11.63±0.99 | 0.61±0.07 | 5.27±0.72 |
| (SB+TG)-M | 12.70±1.16 | 0.60±0.08 | 4.48±0.61* |
| (SB+TG)-H | 12.76±0.44 | 0.53±0.02 | 4.17±0.15** |

Values are mean ± S.D., n=6-8 in each group.* $P<0.05$, ** $P<0.01$ vs. model group, ### $P <0.001$ vs. control group. (SB+TG)-L: orally given silybin 75mg/kg and tangeretin 75mg/kg; (SB+TG)-M: orally given silybin 150 mg/kg and tangeretin 150 mg/kg; (SB+TG)-H: orally given silybin 300 mg/kg and tangeretin 300 mg/kg.

Fig. 34

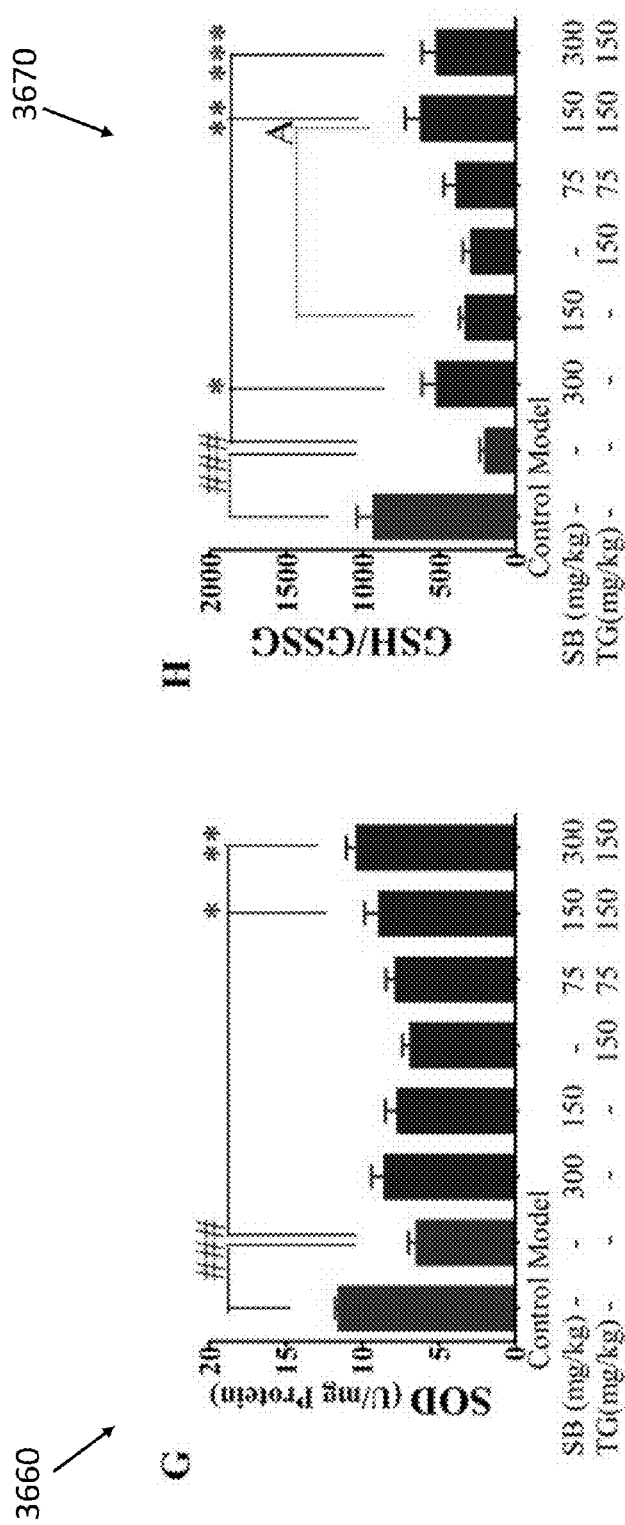

3680

| | Control | Model | SB 300 mg/kg | SB 150 mg/kg | TG 150 mg/kg | (SB+TG)-L | (SB+TG)-M | (SB+TG)-H |
|---|---|---|---|---|---|---|---|---|
| ALT (karmen/ml) | 12.88±2.95 | 205.8±20.5### | 112.3±12.2** | 165.4±21.6 | 185.5±25.8 | 150.1±13.8 | 97.31±12.64** | 40.88±4.55*** |
| AST (karmen/ml) | 41.15±5.48 | 127.5±12.11### | 77.63±5.69** | 111.8±7.66 | 125.3±9.96 | 100.9±11.8 | 73.76±11.44** | 49.83±6.28*** |
| TG (mmol/mg protein) | 0.12±0.01 | 0.35±0.04### | 0.23±0.02* | 0.31±0.01 | 0.37±0.04 | 0.32±0.02 | 0.25±0.01* | 0.19±0.01** |
| TC(mmol/mg protein) | 0.01±0.003 | 0.1±0.02### | 0.05±0.01** | 0.07±0.02 | 0.1±0.01 | 0.08±0.01 | 0.05±0.01* | 0.02±0.004*** |
| SOD(U/mg protein) | 11.57±0.23 | 6.47±0.52### | 8.56±0.84 | 7.72±0.79 | 6.89±0.52 | 7.83±0.63 | 8.91±0.93* | 10.36±0.72** |
| IL-6 (pg/mg Protein) | 114.3±15.7 | 543.6±50.1### | 309.1±32.1** | 463.7±32.3 | 512.0±73.2 | 447.7±50.4 | 342.9±20.2** | 180.6±20.9*** |
| TNF-a(pg/mg Protein) | 121.1±43.3 | 685.1±44.6### | 425.1±47.6** | 572.7±56.4 | 642.3±71.9 | 563.6±57.8 | 374.97±56.97* | 224.4±33.37*** |

Statistically significant differences with respect to the control are expressed as ### $P < 0.001$;
Statistically significant differences with respect to the model are expressed as * $P < 0.05$,  $P < 0.01$, and * $P < 0.001$.

Fig. 37

|  | Steatosis | Ballooning | Inflammation |
|---|---|---|---|
| Control | 0 | 0 | 0 |
| Model | 1.80±0.13 | 1.93±0.07 | 2.47±0.08 |
| SB 300mg/kg | 0.92±0.13* | 0.83±0.09** | 0.88±0.12** |
| SB 150mg/kg | 1.00±0* | 0.96±0.04* | 0.92±0.10** |
| TG 150mg/kg | 1.21±0.11* | 1.86±0.04 | 2.29±0.13 |
| (SB+TG)-L | 1.00±0* | 1.00±0** | 0.73±0.13** |
| (SB+TG)-M | 0.87±0.13* | 0.78±0.14** | 0.72±0.10** |
| (SB+TG)-H | 0.83±0.17** | 0.72±0.18** | 0.50±0.08** |

Statistically significant differences with respect to the model are expressed as * $P < 0.05$,  $P < 0.01$, and * $P < 0.001$.

Fig. 38

METHOD OF INCREASING THE BIOAVAILABILITY OF SILYBIN

FIELD OF THE INVENTION

The present invention relates to a method of increasing the bioavailability of silybin.

BACKGROUND

Silybin is a herbal medicine that is used in chronic liver disease. Silybin undergoes rapid first-pass metabolism, primarily by glucuronidation, resulting in short half-lives and low systemic exposures following oral administration.

In view of the demand for enhancing the therapeutic effects of silybin in treating chronic liver disease in a patient, improvements in methods for increasing the bioavailability of silybin are desired.

SUMMARY OF THE INVENTION

One example embodiment is a method of increasing bioavailability of silybin in a person. The method includes providing silybin and a flavonoid to the person, wherein the flavonoid is tangeretin or baicalein.

Other example embodiments are discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A illustrates the effect of different candidate compounds on basal to apical and apical to basal flux of silybin across Caco-2 (human colorectal adenocarcinoma) cell monolayers in accordance with an example embodiment.

FIG. 4B illustrates the effect of different candidate compounds on basal to apical and apical to basal flux of silybin across Caco-2 (human colorectal adenocarcinoma) cell monolayers in accordance with an example embodiment.

FIG. 7A illustrates the effect of test compounds on the glucuronidation of silybin in Caco-2 (human colorectal adenocarcinoma) cells in accordance with an example embodiment.

FIG. 7B illustrates the effect of test compounds on the glucuronidation of silybin in Caco-2 (human colorectal adenocarcinoma) cells in accordance with an example embodiment.

FIG. 8C illustrates the inhibitory effect of baicalein (BAC) at different dosages on the efflux transport of silybin across Caco-2 (human colorectal adenocarcinoma) cell monolayers in accordance with an example embodiment.

FIG. 8D illustrates the inhibitory effect of tangeretin (TG) at different dosages on the efflux transport of silybin across Caco-2 (human colorectal adenocarcinoma) cell monolayers in accordance with an example embodiment.

FIG. 13C illustrates the transport of silybin across the Madin-Darby canine kidney II-multidrug resistance-associated protein 2 (MDCKII-MRP2) cell line in accordance with an example embodiment.

FIG. 13D illustrates the transport of silybin across the Madin-Darby canine kidney II-breast cancer resistance protein (MDCKII-BCRP) cell line in accordance with an example embodiment.

FIG. 15C illustrates the effect of baicalein (BCA) on the function of BCRP overexpressing MDCK II cell monolayers in accordance with an example embodiment.

FIG. 15D illustrates the effect of baicalein (BCA) on the function of MDR1 overexpressing MDCK II cell monolayers in accordance with an example embodiment.

FIG. 17 illustrates the mean pharmacokinetic parameters of free silybin after oral administration at a dose of 10 mg/kg with or without simultaneous oral administration of 10 mg/kg baicalein in rats in accordance with an example embodiment.

FIG. 18 illustrates the mean pharmacokinetic parameters of total silybin after oral administration at a dose of 10 mg/kg with or without simultaneous oral administration of 10 mg/kg baicalein in rats in accordance with an example embodiment.

FIG. 19A illustrates the mean plasma concentration-time profile for 50 mg/kg silybin with or without simultaneous oral administration of 50 mg/kg BCA in accordance with an example embodiment.

FIG. 19B illustrates the mean plasma concentration-time profile for 50 mg/kg silybin with or without simultaneous oral administration of 50 mg/kg BCA in accordance with an example embodiment.

FIG. 20 illustrates mean pharmacokinetic parameters of free silybin after oral administration at a dose of 50 mg/kg with or without simultaneous oral administration of 50 mg/kg baicalein in rats in accordance with an example embodiment.

FIG. 21 illustrates mean pharmacokinetic parameters of total silybin after oral administration at a dose of 50 mg/kg with or without simultaneous oral administration of 50 mg/kg baicalein in rats in accordance with an example embodiment.

FIG. 22 illustrates the mean pharmacokinetic parameters of free silybin after oral administration at a dose of 10 mg/kg with or without simultaneous oral administration of 10 mg/kg tangeretin in rats in accordance with an example embodiment.

FIG. 23 illustrates the mean pharmacokinetic parameters of total silybin after oral administration at a dose of 10 mg/kg with or without simultaneous oral administration of 10 mg/kg tangeretin in rats in accordance with an example embodiment.

FIG. 24A illustrates the mean plasma concentration-time profile for 10 mg/kg silybin with or without simultaneous oral administration of 10 mg/kg tangeretin (TG) in accordance with an example embodiment.

FIG. 24B illustrates the mean plasma concentration-time profile for 10 mg/kg silybin with or without simultaneous oral administration of 10 mg/kg tangeretin (TG) in accordance with an example embodiment.

FIG. 28 illustrates the effects of silybin co-administered with or without tangeretin (TG) in biochemical parameters in $CCl_4$-treated rats in accordance with an example embodiment.

FIG. 31C illustrates the verification of interleukin 6 (IL-6) in livers from acute liver injury rat model in accordance with an example embodiment.

FIG. 31D illustrates the verification of interleukin 17 (IL-17) in livers from acute liver injury rat model in accordance with an example embodiment.

FIG. 33 illustrates the semi-quantitative histopathological changes of $CCl_4$-induced acute liver injury in rats with different treatment by using slides stained with hematoxylin and eosin (H&E) in accordance with an example embodiment.

FIG. 34 illustrates the characteristics of C57BL/6 mice fed with methionine-choline-sufficient (MCS) diet, methionine choline-deficient (MCD) diet, and MCD diet with silybin only or co-treatment with tangeretin (TG) in accordance with an example embodiment.

FIG. 36G illustrates the enhanced protective effect of silybin on liver function index superoxide dismutase (SOD) levels by co-treatment with tangeretin (TG) in methionine choline-deficient (MCD)-induced nonalcoholic steatohepatitis (NASH) mouse model in accordance with an example embodiment.

FIG. 36H illustrates the enhanced protective effect of silybin on liver function index by co-treatment with tangeretin (TG) in methionine choline-deficient (MCD)-induced nonalcoholic steatohepatitis (NASH) mouse model in accordance with an example embodiment.

FIG. 37 illustrates the effect of treatment with silybin with or without tangeretin (TG) on biochemical parameters in mice fed with methionine choline-deficient (MCD) diet in accordance with an example embodiment.

FIG. 38 illustrates the effect of semi quantitative evaluation of liver damage in mice of different treatment groups using slides stained with hematoxylin and eosin (H&E) in accordance with an example embodiment.

FIG. 39 illustrates a method to increase the bioavailability of silybin in a person in accordance with an example embodiment.

FIG. 40 illustrates a method to treat chronic liver disease in a person in accordance with an example embodiment.

DETAILED DESCRIPTION

Figure 1B:
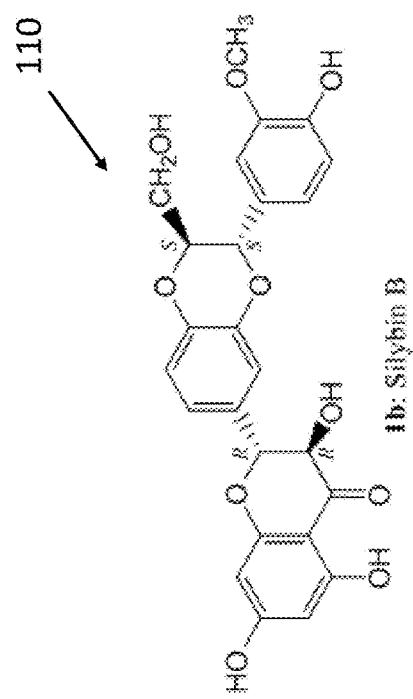
FIG. 1B illustrates the structure of silybin B in accordance with an example embodiment.

Example embodiments relate to methods of increasing bioavailability of silybin in a person by providing to the person silybin and a flavonoid. In one example embodiment, the flavonoid is tangeretin. In another example embodiment, the flavonoid is baicalein.

Example embodiments relate to a pharmaceutical composition to treat chronic liver diseases that include silybin, a flavonoid that increases the bioavailability of silybin. In an example embodiment, the flavonoid is tangeretin. In an example embodiment, the flavonoid is baicalein.

Example embodiments relate to methods to treat chronic liver disease by administering, to a person, silybin and a flavonoid to treat the chronic liver disease. In an example embodiment, the flavonoid is baicalein. In an example embodiment, the flavonoid is tangeretin. In an example embodiment, tangeretin significantly increased the liver-protecting effects of silybin.

In an example embodiment, silybin is an active component of silymarin, extracted from *silybum marianum* and encompasses two diastereoisomers, namely silybin A and silybin B. In an example embodiment, the weight percentage of silybin A in silybin ranges from 40%-70%, 45%-65%, 48%-62%, 50%-60%, 52%-58%, or 54%-56%. In an example embodiment, the weight percentage of silybin B in silybin ranges from 40%-70%, 45%-65%, 48%-62%, 50%-60%, 52%-58%, or 54%-56%. In an example embodiment, silybin A accounts for 50% by weight of silybin, and silybin B accounts for 50% by weight of silybin.

In an example embodiment, the silybin and the flavonoid are provided simultaneously or administered simultaneously to increase the bioavailability of silybin and treat chronic liver disease of the person. In an example embodiment, the silybin and the flavonoid are provided sequentially or administered sequentially to increase the bioavailability of silybin and treat chronic liver disease of the person. In an example embodiment, the silybin and flavonoid are provided to the person by oral administration. In an example embodiment, the flavonoid is provided to the person prior to the silybin.

In an example embodiment, the silybin and the flavonoid are provided or administered at a ratio of 1:1 by weight.

In an example embodiment, the flavonoid provided to the person can inhibit a function of efflux transporters and increase the plasma concentration of silybin. In an example embodiment, the efflux transporter is multi-drug resistance protein 2 (MRP2). In an example embodiment, the efflux transporter is breast cancer resistance protein (BCRP).

In an example embodiment, the pharmaceutical composition of the silybin and flavonoid to treat chronic liver disease is formulated as a form of tablet.

Example 1: Material and Methods 1.1 Chemicals and Reagents

Silybin (48% SA and 52% SB), β-glucuronidase (type B-10 from bovine liver), sulfatase (type H-1 from *Helix pomatia*), quinidine, cyclosporin A, Ko143 [(3S, 6S, 12aS)-1, 2, 3, 4, 6, 7, 12, 12a-Octahydro-9-methoxy-6-(2-methylpropyl)-1, 4-dioxopyrazino[1 ',2':1,6] pyrido [3, 4-b] indole-3-propanoic acid 1, 1-dimethylethyl ester hydrate], MK-571 [5-(3-(2-(7-Chloroquinolin-2-yl)ethenyl)phenyl)-8-dimethylcarbamyl-4,6-dithiaoctanoic acid sodium salt hydrate] and naringenin (NG) were purchased from Sigma-Aldrich (St. Louis, Mo., USA). Baicalein, galangin, biochanin A, apigenin, kaempferide, isorhamnetin, luteolin, morin, diosmetin, myricetrin, chelerythrine, (−)-ECG, fisetin, curcumin, myricetin, genistein, chrysin, quercetin, kaempferol, dihydromyricetin, resveratrol, hesperidin and tangeretin were purchased from MelonePharma (Dalian Melone Biology Technology Co., Ltd., Dalian, China). The identity and purity of these chemicals were performed by liquid chromatography-mass spectrometry (LC-MS) in our laboratory. All other chemicals and reagents were of analytical grade or higher and were purchased from commercial sources. Serial dilution of the stock solutions with dimethyl sulfoxide (DMSO) was made to generate various working concentrations of all compounds. The percentage of DMSO in the final reaction solution was 1%.

1.2 Animals

Male Sprague-Dawley (SD) rats weighing 200-250 grams (g) and male wild-type (WT) C57BI/6 mice were purchased from the Guangdong Medical Laboratory Animal Center. Animals were housed 4 per cage with food and water provided ad libitum and acclimated in the laboratory for at least one week prior to experimentation. All procedures involving animals and animal care were compliant with regulations of the Committee on Care and Use of Laboratory Animals at Guangzhou University of Chinese Medicine (No # ZYYL20150807).

1.3 Cell Culture

Human colorectal adenocarcinoma-2 (Caco-2) cells was obtained from American Type Culture Collection (Manassas, Va.) and frozen at −80° C. For transport study, cells were cultured at 37° C./5% $CO_2$ in Dulbecco's modified Eagle's medium supplemented with 10% fetal bovine serum, 1% nonessential amino acids, and 1% penicillin-streptomycin. After harvesting at 90% confluence, a cell monolayer was prepared by seeding $0.6 \times 10^5$ cells/cm$^2$ onto polyester filter membranes in 12-well TRANSWELL® plates (COSTAR® Cat. No. #3460, Corning Costar Co., NY, USA.), or $1.0 \times 10^5$ cells/cm$^2$ onto polyester filter membranes in 6-well TRANSWELL® plates (COSTAR® Cat. No. #3450, Corning Costar Co., NY, USA.). The culture medium was changed 24 hours after seeding to remove cell debris and dead cells; after which the medium was changed on alternate days. Monolayers were used for transport assays between 21 and 23 days for Caco-2 cells. Prior to transport study, cell monolayers were certified based on internal criteria on transepithelial electrical resistance (TEER) values.

Parental Madin-Darby canine kidney II (MDCKII), multidrug resistance gene 1-Madin-Darby canine kidney II (MDR1-MDCKII), breast cancer resistance protein-Madin- Darby canine kidney II (BCRP-MDCKII), and multi-drug resistance protein 2-Madin-Darby canine kidney II (MRP2-MDCKII) cells were kindly provided by the Netherlands Cancer Institute (Amsterdam, Netherlands) and frozen at −80° C. The MDCKII cells were cultured at 37° C./5% $CO_2$ in Dulbecco's modified Eagle's medium supplemented with 10% fetal bovine serum, 1% nonessential amino acids, and 2% penicillin-streptomycin. The cells were seeded on transwell inserts (Corning Inc.) at a density of $2.0 \times 10^5$ cells/$cm^2$ and grown for 4-5 days to form confluent monolayers.

Prior to transport study, cell monolayers were certified based on our internal criteria on transepithelial electrical resistance (TEER) values, and only monolayers that met the acceptance criteria (transepithelial electrical resistance >500 $\Omega \cdot cm^2$ for Caco-2 cells and >200 $\Omega \cdot cm^2$ for MDCK cells) were selected for transport studies.

1.4 Bidirectional Transport Studies with Caco-2 Cell and MDCK II

Bidirectional transport assays in human colorectal adenocarcinoma 2 (Caco-2) and Madin-Darby canine kidney II (MDCK II) was carried out by dosing substrates in assay buffer to either the apical chamber (A-to-B) or the basolateral chamber (B-to-A); cells were then incubated at 37° C. with shaking at 50 rotations per minute (rpm), and 100 µl samples were collected at 30, 60, 90, 120 and 180 minutes from the basolateral chamber to study the drug transport of AP to BL, or apical chamber to study the drug transport of BL to AP. Cell monolayers were then washed twice with ice-cold assay buffer and lysed with methanol on ice for 10 minutes. For inhibition studies, Caco-2 or MDCK II cell monolayers were pre-incubated with an inhibitor in both apical and basolateral chambers for 30 minutes, and bidirectional transport of 10 µM silybin was conducted in the absence (control) or presence of the inhibitor in both chambers. Sample (100 µl) was mixed with 50 µl methanol containing internal standard (25 ng/ml), and stored at −80° C. until liquid chromatography-mass spectrometry (LC-MS)/mass spectrometry (MS) analysis. For fluorescence intensity detection, samples collected from AP or BL side were immediately detected in 96 well black plate by Microplate ultraviolet-visible spectroscopy (UV/VIS) spectrophotometer (TECAN infinite M200 PRO, Männedorf, Switzerland). In all cases, each determination was performed in triplicate.

The apparent permeability coefficients (Papp) were calculated as $Papp = dQ/dt \times 1/(C"0"A)$ where dQ/dt (mM/sec) is the rate of permeation of the drug across the cells, C0 (millimolar (mM)) is the donor compartment concentration at time zero and A ($cm^2$) is the area of the cell monolayer. C0 is obtained from analysis of the dosing solution at the start experiment. Efflux Ratio (ER)=Papp (B to A)/Papp (A to B), while Papp (B–A) is the Papp value measured in the B to A direction, and Papp (A–B) is the Papp value measured in the A to B direction.

1.5 Preparation of Rat Sandwich-Cultured Hepatocytes

Sandwich-cultured rat hepatocytes (SCHs) were established according to previously described methods with minor modifications. Primary rat hepatocytes were isolated from male Sprague Dawley® (SD) rats (220-270 g) using a collagenase perfusion as described previously and plated at a density of $7.4 \times 10^5$ cells/2 ml/well onto six-well BioCoat plates. Approximately 24 hours later, hepatocytes were overlaid with 2 ml of 0.25 mg/ml BD Matrigel basement membrane matrix in Dulbecco's modified Eagle medium (DMEM) containing 1% volume by volume percentage (v/v) insulin/transferrin/selenium culture supplement, 0.1 M dexamethasone, 2 mM L-glutamine, 1% (v/v) minimum essential medium nonessential amino acids, 1% penicillin-streptomycin. Hepatocytes were cultured for 4 days to allow extensive formation of canalicular networks between cells before experimentation and the medium was changed daily.

1.6 Accumulation Experiments Using Rat Sandwich-Cultured Hepatocytes

Sandwich-cultured hepatocytes (SCHs) were pre-incubated in 2 milliliters (ml) of warm Hank's Balanced Salt Solution (HBSS) with or without $Ca^{2+}$ at 37° C. for 15 minutes; the tight junctions of the bile canaliculi open temporally after exposure to HBSS without $Ca^{2+}$. Subsequently, cells were incubated at 37° C. for 20 minutes with 1.5 ml of standard HBSS containing silybin (10 µM), or MK 571 (50 µM) as a positive control, or baicalein (25, 15.8, 5, 1.58, 0.5, 0.16 µM), or tangeretin (25, 15.8, 5, 1.58, 0.5 µM). After 20 min, cells were washed three times with ice-cold standard HBSS. The cell samples were lysed by sonication in 1 ml of water for 5 seconds with the ultrasonic cell disruption system (SONICS & MATERIACS, INC., Newtown, Conn., USA). Conjugated silybin and unconjugated (free) silybin were quantified by high-performance liquid chromatography-tandem mass spectrometry (HPLC-MS/MS). Transport function was normalized to the protein content of the hepatocytes which was evaluated by bicinchoninic acid (BCA) protein assay (Pierce Chemical, Rockford, Ill.). The biliary excretion index (BEI; %) and in vitro biliary clearance (Clbiliary; ml/min/kg) were calculated by using B-CLEAR technology (Qualyst, Inc., Research Triangle Park, N.C.) based on the following equations:

$$CLbile, int = \frac{Uptake(+Ca^{2+}/Mg^{3+}) - Uptake(-Ca^{3+}/Mg^{2+})}{Incubation\ time \times Concentration(medium)} \quad Eq1.$$

$$BEI\% = \frac{Uptake(+Ca^{3+}/Mg^{2+}) - Uptake(-Ca^{2+}/Mg^{2+})}{Uptake(+Ca^{2+}/Mg^{2+})} \times 100\% \quad Eq2.$$

1.7 Pharmacokinetic Studies

The rats were randomly divided into three groups with six rats in each group. The oral administration dosages of silybin were 10 and 50 mg/10 ml/kg body weight without or with baicalein/tangeretin at the same dosage. Before experimentation, the animals were fasted for 24 hours with water ad libitum, and maintained at a temperature of 21° C. with 70% relative humidity and a 12 hour light/dark cycle. After oral administration, tail vein blood samples were collected (0.1 ml) into heparinized 0.65 ml micro-centrifuge tubes at the following time intervals: 0, 15, 30, 45, 60, 90, 120, 240, 360, 480, and 720 minutes. The blood samples then were immediately centrifuged at 4,000 rotations per minute (rpm) for 15 minutes at 4 degrees Celsius (° C.), and the resulting plasma was collected and stored at −80° C. until analysis.

1.8 Quantification of Conjugated Silybin and Free Silybin

To estimate the concentration of total glucuronide and sulfate conjugates of silybin in bio-samples including plasma, cell, and media, enzymatic hydrolysis with bovine liver (8000 U/ml) and sulfatase (80 units per milliliter (U/ml)) was performed with 10 microliter (µl) aliquot of samples. The reactions were terminated by the addition of 40 µl of ice-cold acetonitrile containing 1% glacial acetic acid and internal standard NG (25 ng/ml). After centrifugation at 13,500 rotations per minute (rpm) for 15 minutes at 4° C., the supernatants were evaporated to dryness by nitrogen evaporator, and the residue was reconstituted with 60 µl of 30% methanol in water containing 1% ascorbic acid. An aliquot of 10 µl of the final solution was injected into LC-MS/MS for analysis. The completion of de-conjugation reaction was monitored by mass spectrometry. In parallel, 10 µl aliquots of samples without enzymes were treated with 40 µl of ice-cold acetonitrile containing 1% glacial acetic acid and naringenin (NG) (25 nanogram per milliliter (ng/ml)) to determine the concentration of free silybin. The total concentrations of glucuronides and sulfates in samples were estimated from the difference between the amount of silybin released by incubation with both glucuronidase and sulfatase and the amount of free silybin without enzymes incubation.

1.9 Bioanalytical Assay with LC-MS/MS

The analysis of silybin and total concentrations of glucuronides and sulfates was performed on an Agilent HP 1100 LC-MS system (Agilent, CA). A Waters ACQUITY UPLC® BEH C18 Column (1.7 µm, 2.1×50 mm, Waters Corp., Ireland) was used for detection with a C18 Security Guard cartridge (4×2.0 mm i.d., Phenomenex, Torrance, Calif.). Silybin A and silybin B were well separated using optimized gradient elution with methanol (mobile phase B) and 0.1% formic acid in water (mobile phase A) as mobile phase at a flow rate of 0.4 ml/min with a run time of 10 minutes. The gradient employed was as follows (time: mobile phase B percentage): 0 min: 25%, 6 minutes: 40%, 6.5 minutes: 25%.

MS parameters including: capillary voltage, −4000 V; nebulizer pressure, 40 pounds per square inch (psi); drying gas, 9 liters per minute (L/min); drying gas temperature, 325° C.; fragment voltage, 35 volts; dwell time, 200 milliseconds (ms); scan mode, selective ion monitoring (SIM) with [M-H]− for silybin (mass-to-charge ratio (m/z) 481), mono-glucuronide (m/z 657), and NG (m/z 271), respectively. LC-MS data were obtained by Agilent ChemStation Software.

The limit of quantification and linear quantitative range for the silybin A and silybin B was 5 nanogram per milliliter (ng/ml) and 5 ng/ml to 12500 ng/ml, respectively. To quantify the different compounds in plasma samples, calibration curves and three quality control (QC) samples were used with every set of unknown samples.

1.10 Effects of Silybin on Acute Liver Damage Induced by Carbon Tetrachloride ($CCl_4$) in Rats Male SD rats were randomly divided into six groups: 1) Group I orally received blank vehicle for 7 days, and intraperitoneally (i.p.) injected with olive oil (2 ml/kg body weight) on day 7; 2) Group II orally received blank vehicle for 7 days, and injected with $CCl_4$-olive oil mixture (40% $CCl_4$, i.p., 2 ml/kg body weight) on day 7; 3) Group III was treated with silybin (100 mg/kg bodyweight, per os (p.o.) for 7 days, and injected with $CCl_4$-olive oil mixture (40% $CCl_4$, i.p., 2 ml/kg body weight) on day 7, 2 hour after administration of silybin; 4) Group IV was treated with silybin (100 mg/kg bodyweight, p.o.) and tangeretin (100 mg/kg bodyweight, p.o.) mixture for 7 days, and injected with $CCl_4$-olive oil mixture (40% $CCl_4$, i.p., 2 ml/kg body weight) on day 7, 2 hour after administration of the mixture; 5) Group V was treated with silybin (50 mg/kg bodyweight, p.o.) and tangeretin (50 mg/kg bodyweight, p.o.) mixture for 7 days, and injected with $CCl_4$-olive oil mixture (40% $CCl_4$, i.p., 2 ml/kg body weight) on day 7, 2 hour after administration of the mixture; 6) Group VI was treated with tangeretin (100 mg/kg bodyweight, p.o.) for 7 days, and injected with $CCl_4$-olive oil mixture (40%, i.p., 2 ml/kg body weight) on day 7, 2 hour after administration of tangeretin. Model and control group were daily treated orally with blank solvent (35% PEG400: 15% Cremophor EL: 5% ethanol: 45% saline).

24 hours after the $CCl_4$-induced toxic liver injury was initiated, rats were sacrificed under ether anesthesia. Blood was collected from the abdominal aorta for biochemical estimations. The liver was immediately removed and weighed. A large portion of the liver was snap-frozen in the liquid nitrogen and the remaining tissue was fixed in 10% buffer formalin, processed and embedded in paraffin for histological examination after hematoxylin and eosin (H&E) staining. Steatohepatitis was evaluated by level of alanine aminotransferase (ALT), aspartate aminotransferase (AST), triglycerides, total cholesterol and superoxide dismutase (SOD) using commercial kits (Nanjing Jiancheng Bioengineering Institute, Nanjing, China) according to manufacturer's instructions and histological assessment and scoring according to standardized criteria by a pathologist blind to the study.

1.11 Effects of Silybin on the Methionine-Choline Deficient (MCD) Diet Induced Mice Nonalcoholic Steatohepatitis (NASH) Model Male wild-type (WT) mice C57l BI/6 were fed either methionine/choline-sufficient (MCS) chow diet (Trophic Animal Feed High-tech Co., Ltd, China) or MCD diet (Trophic Animal Feed High-tech Co., Ltd, China) for 7 weeks. Animals were randomly divided into eight groups: 1) control, fed a standard control MCS diet and given vehicle (35% polyethylene glycol (PEG) 400:15% Cremophor EL:5% ethanol:45% saline); 2) rats fed a MCD diet and given vehicle; 3) rats fed the MCD diet and orally treated with silybin (300 milligrams per kilogram (mg/kg)); 4) rats fed the MCD diet and orally treated with silybin (150 mg/kg); 5) rats fed the MCD diet and orally treated with tangeretin (150 mg/kg); 6) rats fed the MCD diet and orally treated with 75 mg/kg silybin and 75 mg/kg tangeretin (SB & TG—L); 7) rats fed the MCD diet and orally treated 150 mg/kg silybin and 150 mg/kg tangeretin (SB & TG—M); 8) rats fed the MCD diet and orally treated with 300 mg/kg silybin and 150 mg/kg tangeretin (SB & TG—H). Body weight was intermittently monitored during the diet-induction period and every two or three days during the intervention period.

At the end of 8 weeks, mice were sacrificed under ether anesthesia. The following procedures are same as the description under "2.10 Effects of silybin on acute liver damage induced by $CCl_4$ in rats". The cytokine levels including tumor necrosis factor alpha (TNF-α) (eBioscience Inc, San Diego, Calif., USA), interleukin-6 (IL-6) assay kit (Raybiotech, Norcross, Ga., USA) in serum of NASH model were further measured using commercially available enzyme-linked immunosorbent assay (ELISA) kits.

1.12 Pharmacokinetic Calculations and Statistical Analysis

Pharmacokinetic parameters including half-life (T1/2), volume of distribution (Vd), oral clearance (CL/F), and area under the concentration-time curve (AUC) were calculated using the software package PK Solutions 2.0.2 (SUMMIT Co., Ashland, Ohio, USA) with non-compartment analysis. One-way analysis of variance (ANOVA) was used when multiple groups were compared and the Bonferroni post hoc correction was used to accommodate multiple testing. The two-sided unpaired Student's t-test was used when treatments or differences between two groups were compared. Data that did not show normal distribution were log transformed to normalize the distribution of the data sets and enable statistical comparison. During all statistical analyses, differences in group sizes were considered in the calculations. Differences were considered statistically significant when P<0.05. All data is presented as geometric mean±S.D.

Example 2: Screening the Bioenhancer Candidates Using Caco-2 Cell Model

Caco-2 cells monolayer both structurally and functionally resembles the small intestinal epithelium and show promise as a simple in vitro model for study of drug absorption and metabolism during absorption in the intestinal mucosa. Therefore, the absorbability of the silybin and the enhanced absorption effect of the test compounds was evaluated under the conditions of this experiment using the validated Caco-2 cell monolayer model. To validate this model, the bidirectional transport of genistein were examined each time and the mean Papp values of genistein tested with the monolayers were $1.30\pm0.30\times10^{-5}$ centimeters per second (cm/s), which were consistent with the values reported in the literature.

Figure 1A:
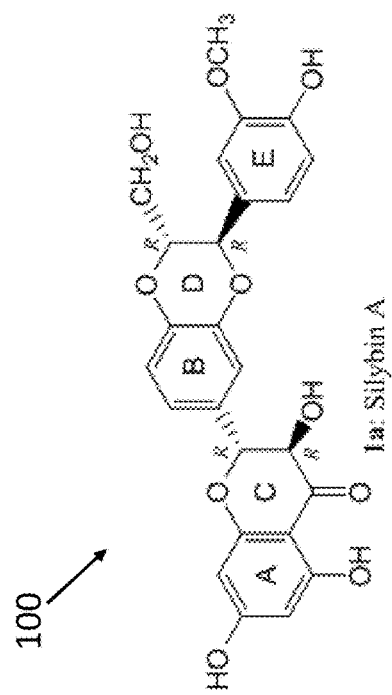
FIG. 1A illustrates the structure of silybin A in accordance with an example embodiment.

FIG. 1 shows the structures 100 and 110 of silybin A and silybin B.

Figure 2:
FIG. 2 illustrates the effects of quinidine (QND), cyclosporin A (CsA), (E)-3-[[[3-[2-(7-chloro-2-quinolinyl) ethenyl]phenyl][[3-(dimethylamino)-3-oxopropyl]thio] methyl]thio]-propanoic acid, sodium salt (MK571) and (3S, 6S,12aS)-1,2,3,4,6,7,12,12a-octahydro-9-methoxy-6-(2-methylpropyl)-1,4-dioxo-pyrazino[1',2':1,6]pyrido[3,4-b] indole-3-propanoic acid 1,1-dimethylethyl ester (Ko143) on the transport of silybin across Caco-2 (human colorectal adenocarcinoma) cell monolayers in accordance with an example embodiment.

FIG. 2 shows a table 200 illustrating the effects of quinidine, cyclosporine A, MK571 and Ko143 on the transport of silybin across Caco-2 cell monolayers.

Figure 3A:
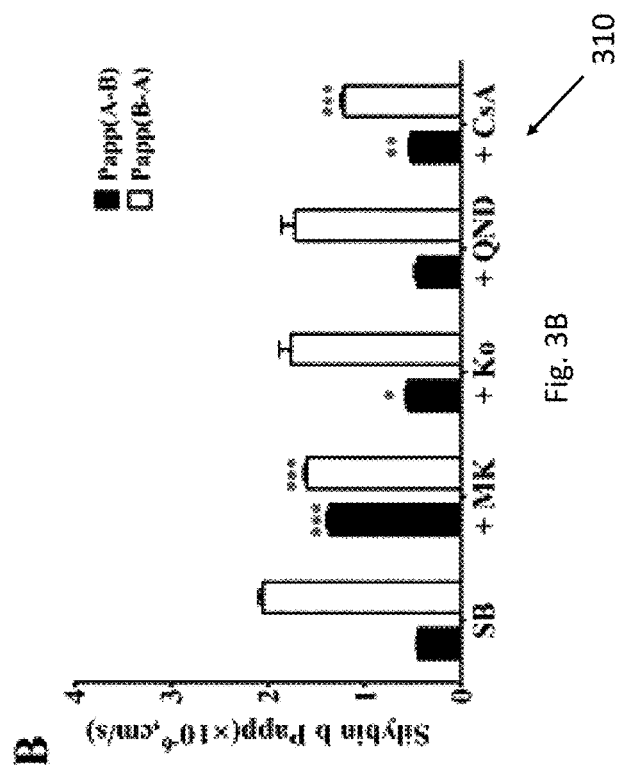
FIG. 3A illustrates the effects of efflux transporter inhibitors QND, CsA, MK571 and Ko143 on the transport behavior of silybin across Caco-2 (human colorectal adenocarcinoma) cell monolayers model in accordance with an example embodiment.
Figure 3B:
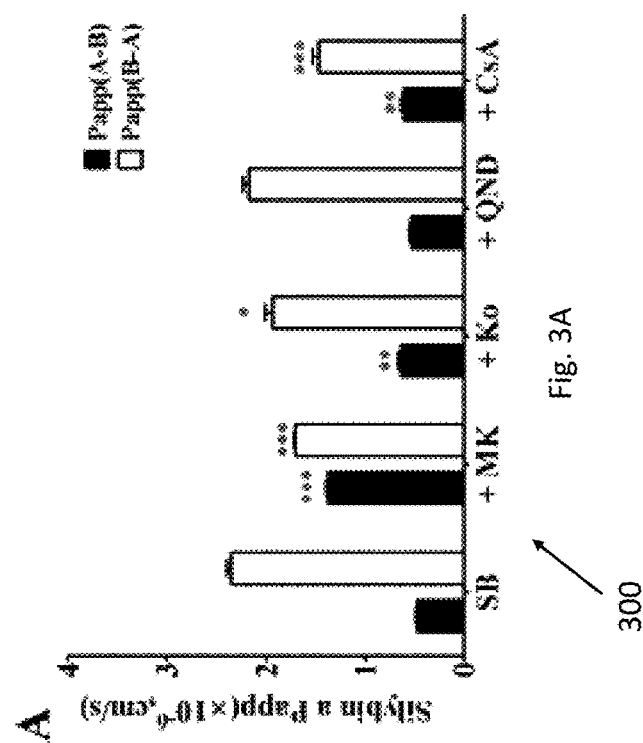
FIG. 3B illustrates the effects of efflux transporter inhibitors QND, CsA, MK571 and Ko143 on the transport behavior of silybin across Caco-2 (human colorectal adenocarcinoma) cell monolayers model in accordance with an example embodiment.
Figure 3C:
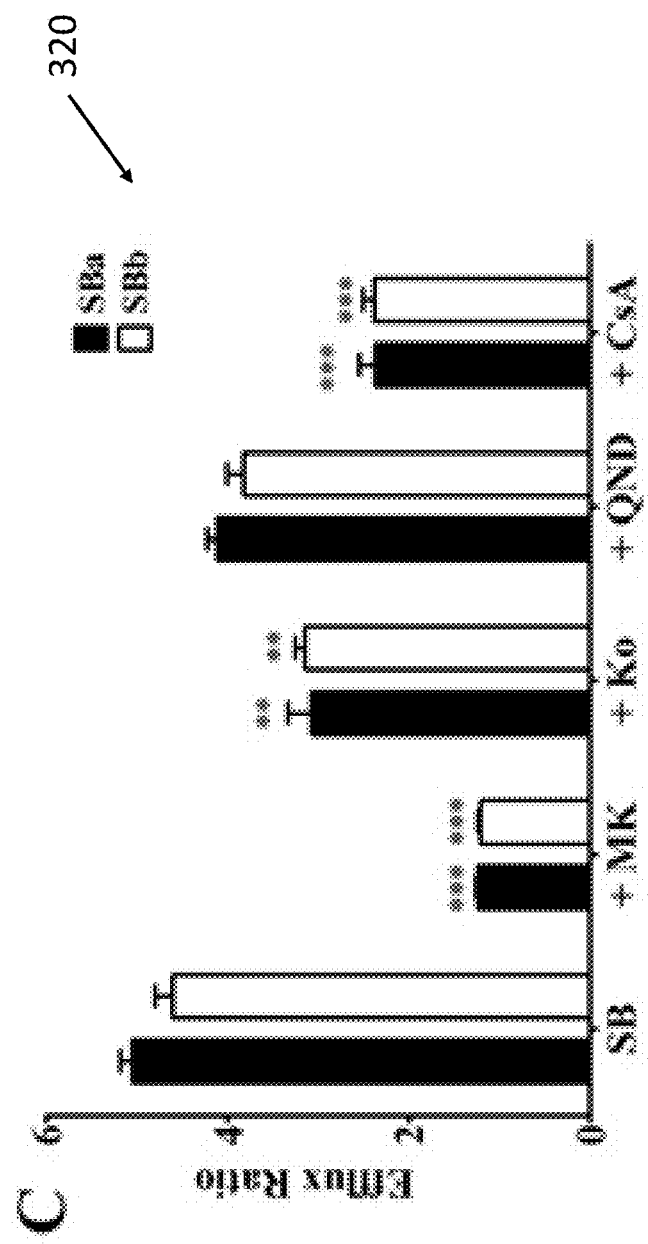
FIG. 3C illustrates the effects of efflux transporter inhibitors QND, CsA, MK571 and Ko143 on the transport behavior of silybin across Caco-2 (human colorectal adenocarcinoma) cell monolayers model in accordance with an example embodiment.
Figure 5B:
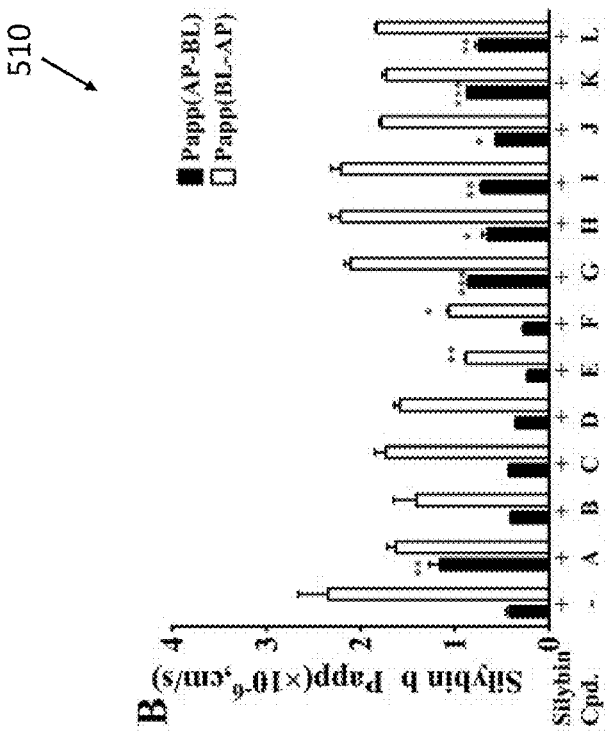
FIG. 5B illustrates the effect of different candidate compounds on basal to apical and apical to basal flux of silybin across Caco-2 (human colorectal adenocarcinoma) cell monolayers in accordance with an example embodiment.
Figure 5A:
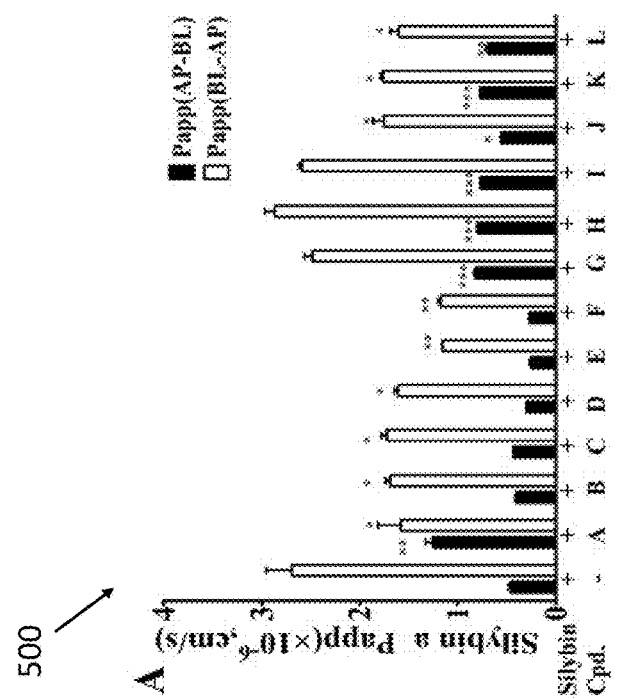
FIG. 5A illustrates the effect of different candidate compounds on basal to apical and apical to basal flux of silybin across Caco-2 (human colorectal adenocarcinoma) cell monolayers in accordance with an example embodiment.
Figure 5D:
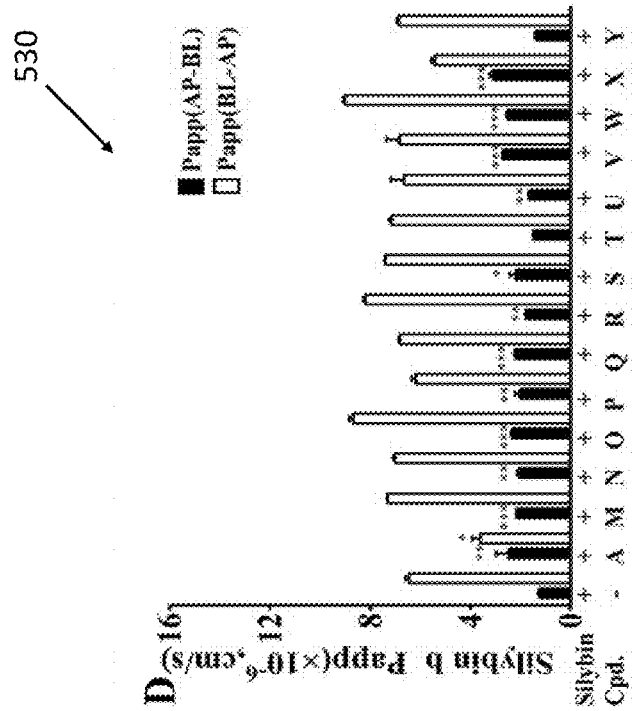
FIG. 5D illustrates the effect of different candidate compounds on basal to apical and apical to basal flux of silybin across Caco-2 (human colorectal adenocarcinoma) cell monolayers in accordance with an example embodiment.
Figure 5C:
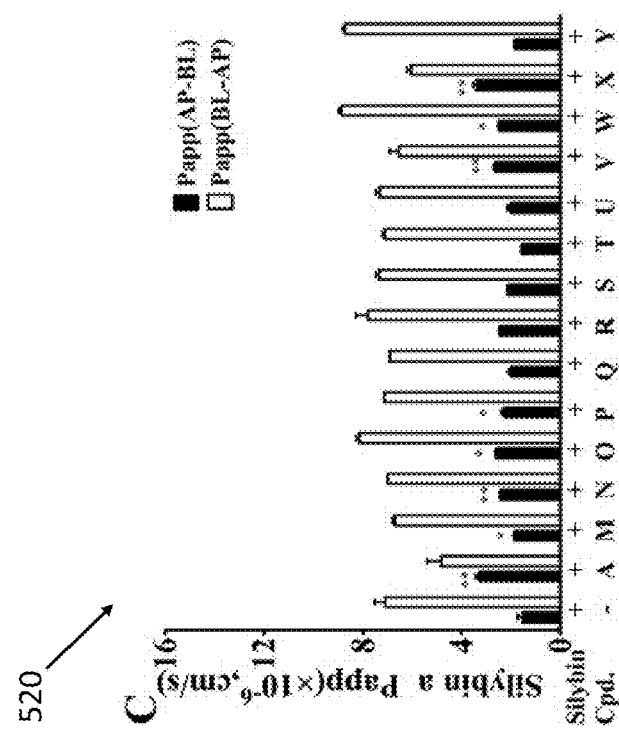
FIG. 5C illustrates the effect of different candidate compounds on basal to apical and apical to basal flux of silybin across Caco-2 (human colorectal adenocarcinoma) cell monolayers in accordance with an example embodiment.
Figures 5E, 5F:
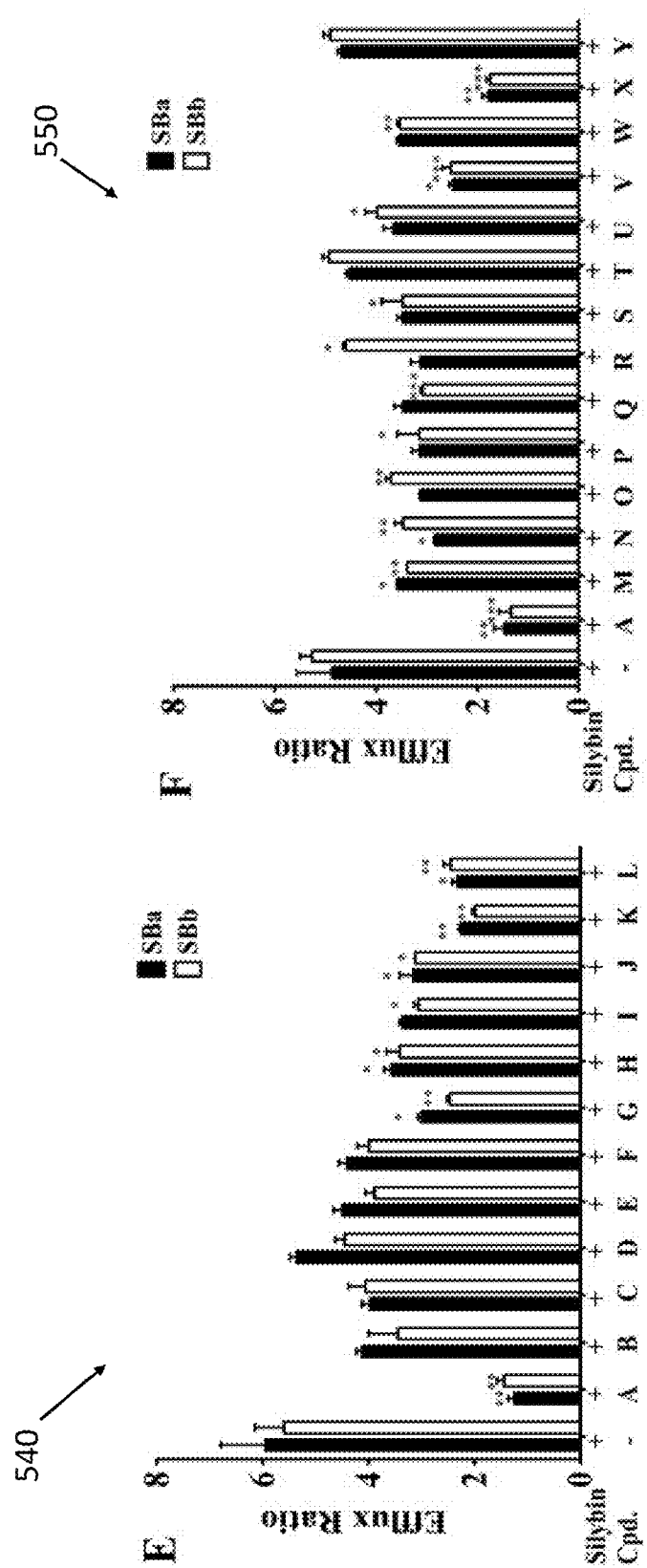
FIG. 5E illustrates the effect of different candidate compounds on basal to apical and apical to basal flux of silybin across Caco-2 (human colorectal adenocarcinoma) cell monolayers in accordance with an example embodiment.
FIG. 5F illustrates the effect of different candidate compounds on basal to apical and apical to basal flux of silybin across Caco-2 (human colorectal adenocarcinoma) cell monolayers in accordance with an example embodiment.

FIGS. 3A, 3B and 3C show graphs 300, 310, 320 illustrating the effects of efflux transporter inhibitors quinidine (QND, 20 μM), cyclosporin A (CsA, 10 μM), MK571 (MK, 50 μM) and Ko143 (Ko, 0.5 μM) on the transport behavior of silybin across Caco-2 cell monolayers model. The permeability values of SBa (A) and SBb (B) as well as efflux ratio (C) have been used for evaluating the effects of efflux transporter inhibitors in Caco-2 cells model. *, P<0.05; , P<0.01; *, P<0.001 vs silybin only.

FIGS. 4A and 4B shows tables 400, 410 illustrating the effect of different candidate compounds (20 μM) on basal to apical and apical to basal flux of silybin across Caco-2 cell monolayers.

As shown in FIG. 2 and FIGS. 3A, 3B and 3C, the efflux ratio of silybin A (SBa) and Silybin B (SBb) were significantly decreased to 1.24 and 1.21 for SBa and SBb with 50 μM MK571 (the inhibitor of MRPs) in Caco-2 cell model indicating MRPs could be the major efflux transporter of silybin. Inhibitor of BCRP, Ko143 at 0.5 μM, also inhibited the efflux ratio of silybin, indicating that silybin may be the substrate of BCRP. In addition, cyclosporine A (10 μM), an inhibitor of both P-gp and MRPs, could significantly inhibit the efflux of silybin with a reduced efflux ratio around 2.3 for both SBa and SBb. However, quinidine (inhibitor of P-gp at 20 μM) did not significantly affect the absorption and efflux of silybin. Therefore, both MRPs and BCRP play the key roles in efflux and absorption of silybin on Caco-2 cells.

The PA-B values of silybin A and silybin B (12-well plate) were $0.47\pm0.03\times10^{-6}$ cm/s, and $0.45\pm0.02\times10^{-6}$ cm/s, respectively, which are consistent with previous reports (FIG. 2 and FIG. 4A). The mean efflux ratios (PB-A/PA-B) of silybin A and silybin B were 5.05 and 4.61 respectively, which is above 2.0. This data indicates there are efflux transporters that modulate the permeation of silybin based on the Food and Drug Administration (FDA) guidelines. However, the major efflux transporter of silybin is still unknown. Thus, special inhibitors for P-glycoprotein (P-gp), breast cancer resistance protein (BCRP) and the multidrug resistance-associated protein (MRPs) were used to evaluate the role of these transporters in the absorption of silybin. To find out the bioenhancer candidates, silybin was co-incubated with different flavonoids. The bidirectional Papp values of the silybin (10 μM) in the presence or absence of test compound (20 μM) were evaluated and summarized in FIGS. 3A, 3B, 3C, 4A and 4B. Significant inhibitions with the efflux ratio of silybin <2.5 following co-incubation were observed with baicalein, tangeretin, chelerythrine and (−)-ECG. MRPs inhibitor MK571 was used as a positive control.

FIGS. 5A, 5B, 5C, 5D, 5E and 5F show graphs 500, 510, 520, 530, 540, 550 illustrating the effect of different candidate compounds (20 μM) on basal to apical and apical to basal flux of silybin across Caco-2 cell monolayers. The permeability values of SBa and SBb in the 12-well transwell plate (A, B) or in the 6-well transwell plate (C, D) were compared in the absence and in the presence of test compounds. The efflux ratio indicates the degree of inhibition on the transport of silybin by various candidate compounds across 6 and 12-well transwell plate (E, F).*, P<0.05; , P<0.01; *, P<0.001 vs silybin only.

Figure 6:
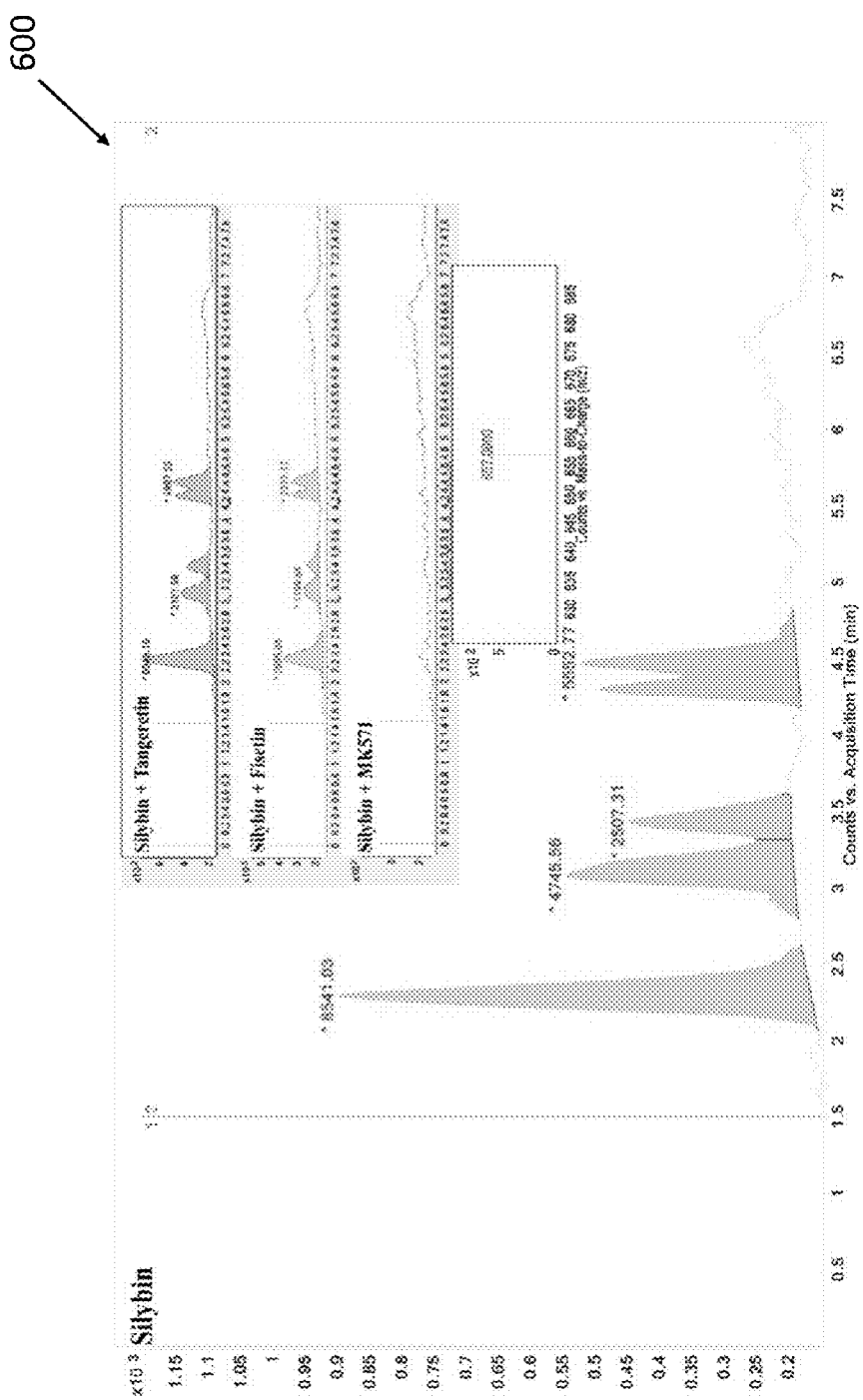
FIG. 6 illustrates a liquid chromatography-mass spectrometry (LC-MS) chromatogram of glucuronides of silybin incubated in the absence and presence of test compounds in Caco-2 (human colorectal adenocarcinoma) cell monolayers in accordance with an example embodiment.
Figure 8B:
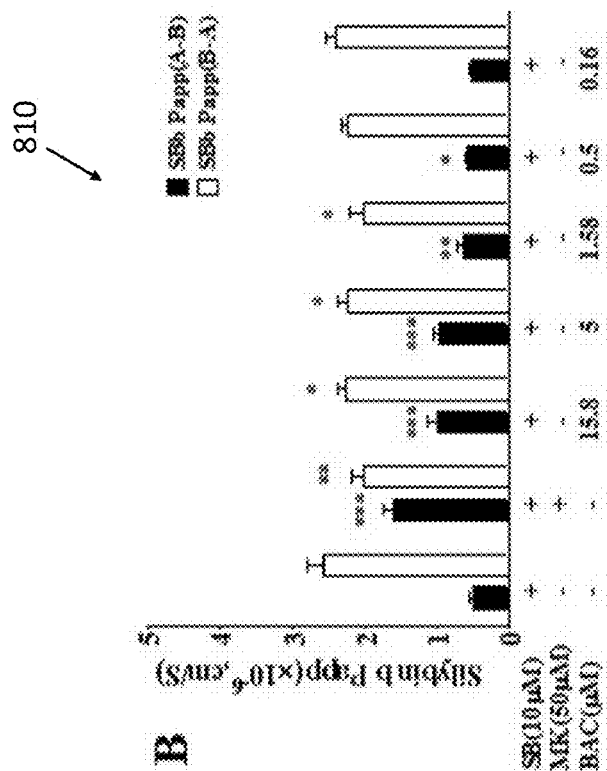
FIG. 8B illustrates the inhibitory effect of baicalein (BAC) at different dosages on the efflux transport of silybin across Caco-2 (human colorectal adenocarcinoma) cell monolayers in accordance with an example embodiment.
Figure 8A:
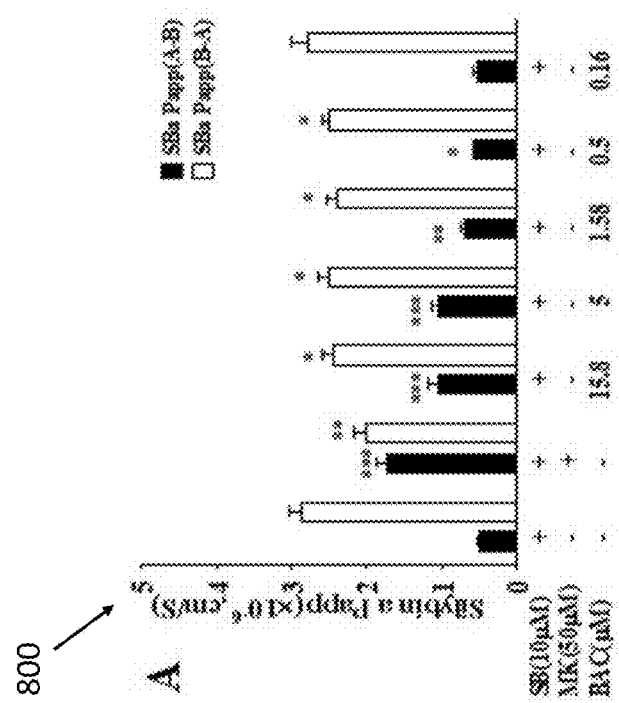
FIG. 8A illustrates the inhibitory effect of baicalein (BAC) at different dosages on the efflux transport of silybin across Caco-2 (human colorectal adenocarcinoma) cell monolayers in accordance with an example embodiment.
Figure 8E:
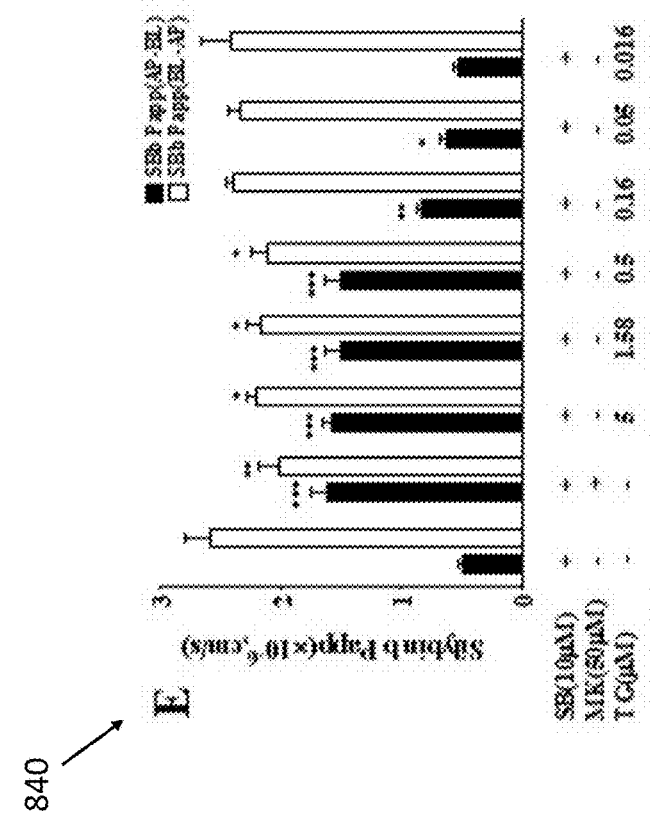
FIG. 8E illustrates the inhibitory effect of tangeretin (TG) at different dosages on the efflux transport of silybin across Caco-2 (human colorectal adenocarcinoma) cell monolayers in accordance with an example embodiment.
Figure 8F:
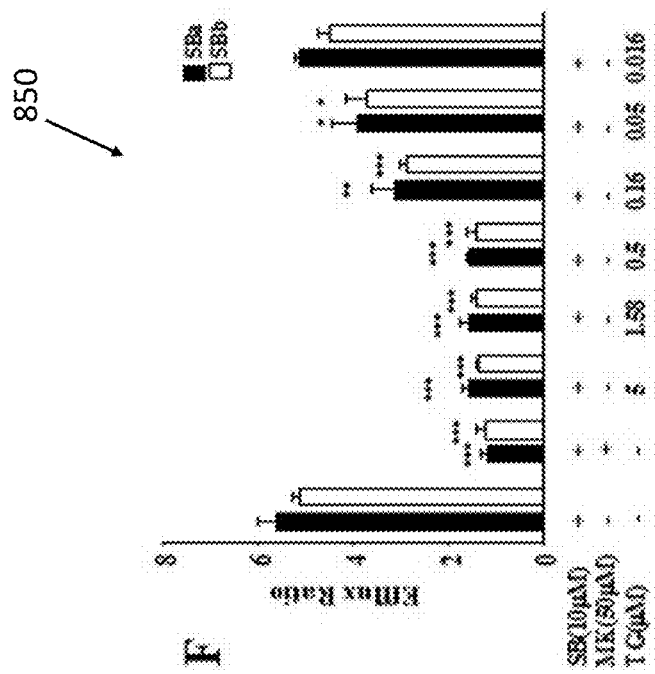
FIG. 8F illustrates the inhibitory effect of tangeretin (TG) at different dosages on the efflux transport of silybin across Caco-2 (human colorectal adenocarcinoma) cell monolayers in accordance with an example embodiment.
Figures 9A, 9B:
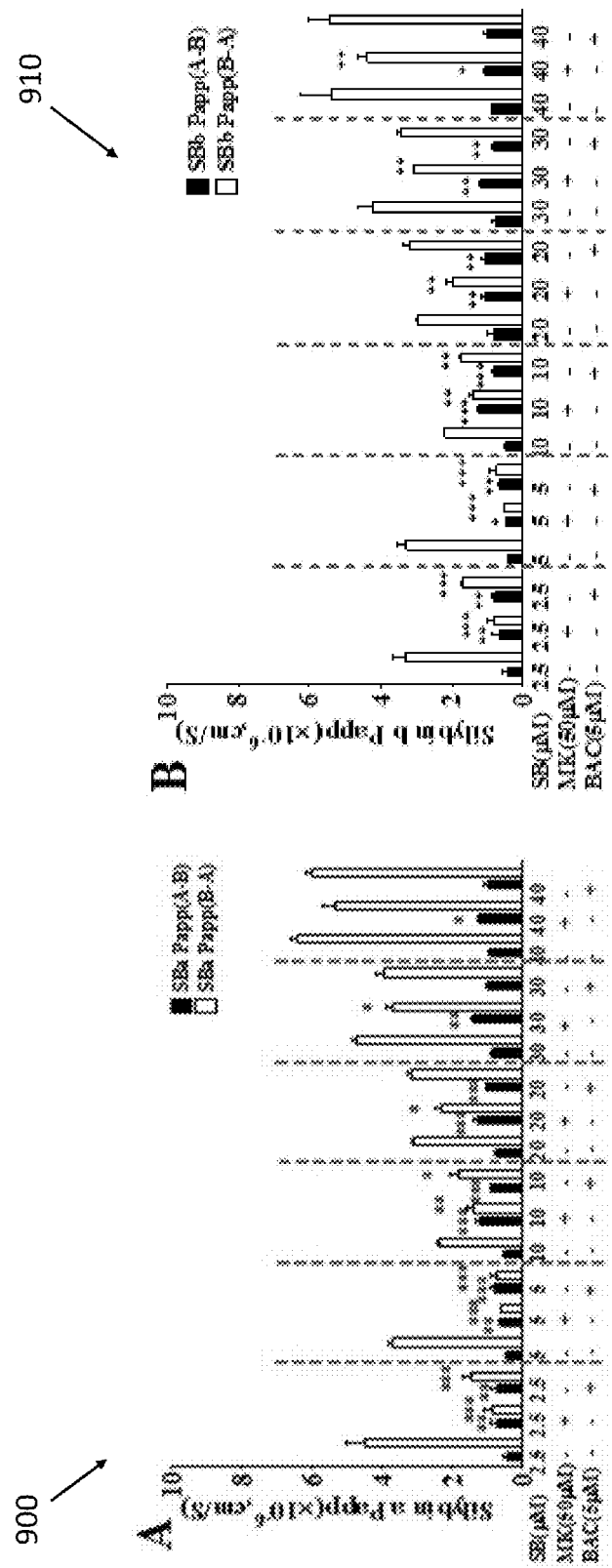
FIG. 9A illustrates the inhibitory effect of baicalein (BAC) on bidirectional flux of silybin at different concentrations across Caco-2 (human colorectal adenocarcinoma) cell monolayers in accordance with an example embodiment.
FIG. 9B illustrates the inhibitory effect of baicalein (BAC) on bidirectional flux of silybin at different concentrations across Caco-2 (human colorectal adenocarcinoma) cell monolayers in accordance with an example embodiment.
Figure 9D:
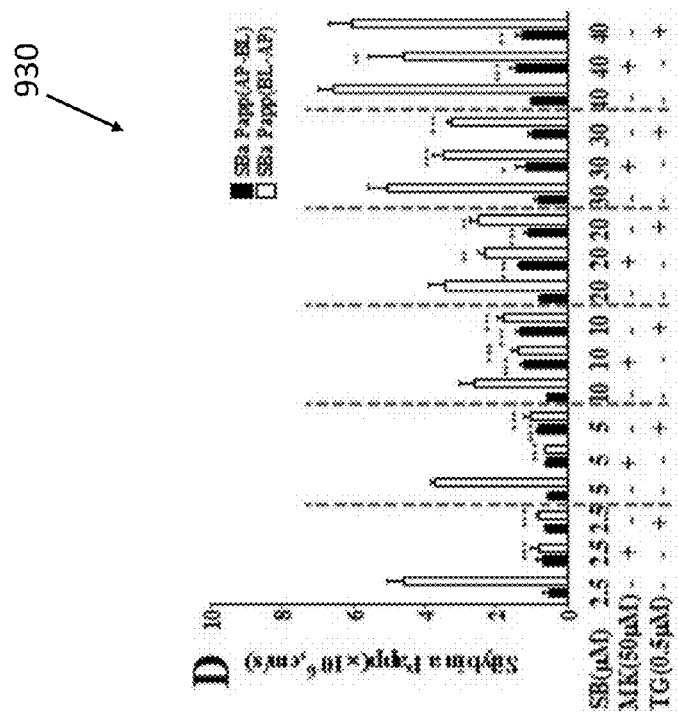
FIG. 9D illustrates the inhibitory effect of tangeretin (TG) on bidirectional flux of silybin at different concentrations across Caco-2 (human colorectal adenocarcinoma) cell monolayers in accordance with an example embodiment.
Figure 9C:
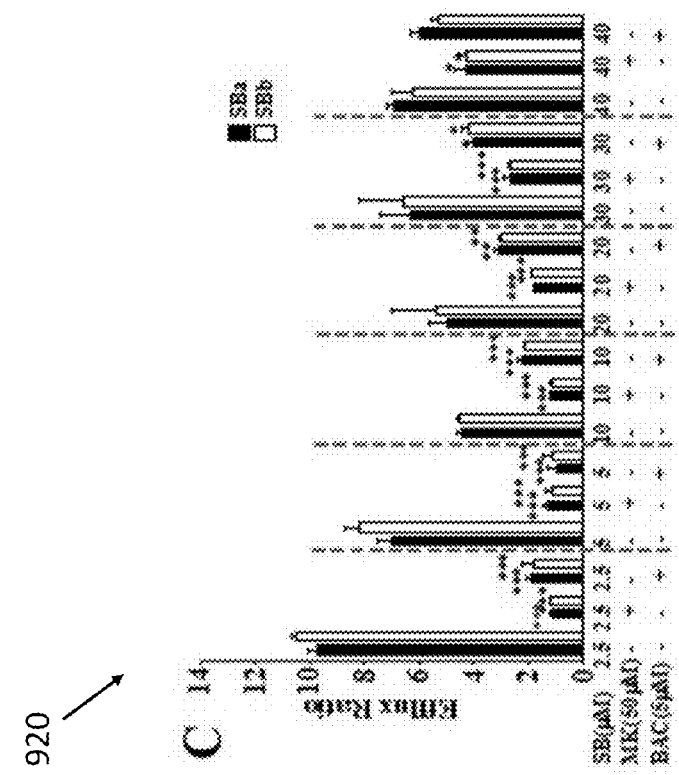
FIG. 9C illustrates the inhibitory effect of baicalein (BAC) on bidirectional flux of silybin at different concentrations across Caco-2 (human colorectal adenocarcinoma) cell monolayers in accordance with an example embodiment.
Figure 9F:
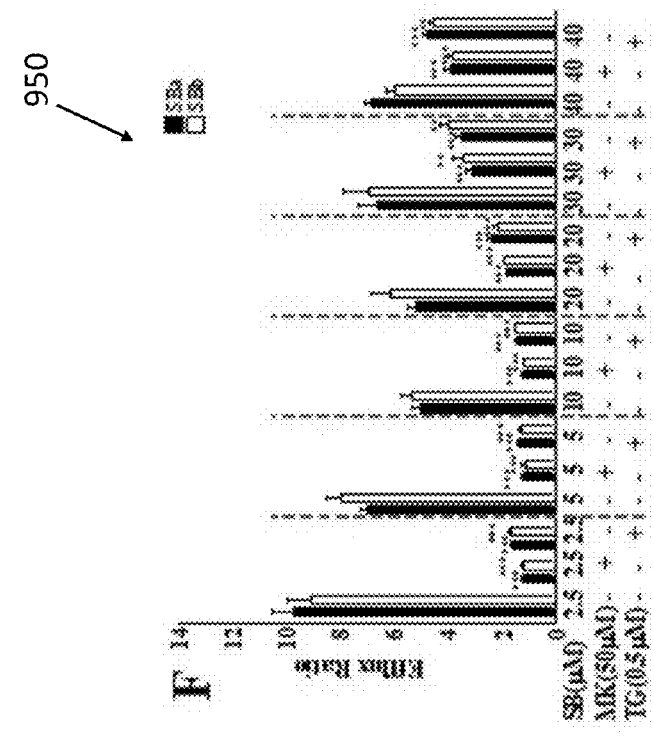
FIG. 9F illustrates the inhibitory effect of tangeretin (TG) on bidirectional flux of silybin at different concentrations across Caco-2 (human colorectal adenocarcinoma) cell monolayers in accordance with an example embodiment.
Figure 9E:
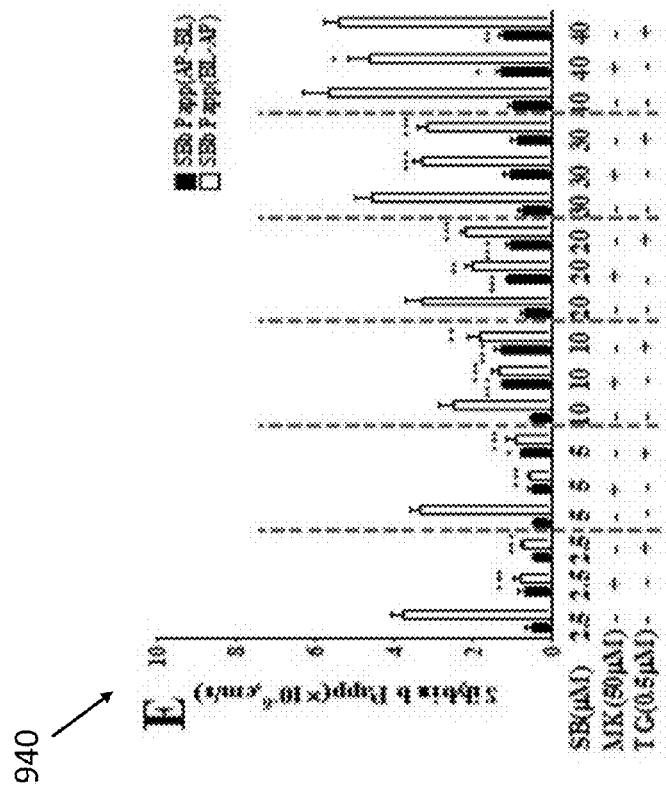
FIG. 9E illustrates the inhibitory effect of tangeretin (TG) on bidirectional flux of silybin at different concentrations across Caco-2 (human colorectal adenocarcinoma) cell monolayers in accordance with an example embodiment.

Example 3: Effect of Test Compounds on the Metabolism of Silybin in Caco-2 Cells Silybin is primarily metabolized to glucuronide (about 55%) and sulfate (about 28%) conjugates in human plasma after oral administration. To examine whether the co-incubation of flavonoids could affect the conjugation of silybin, the peak area of silybin glucuronides was measured by LC-MS (FIG. 6). Identification of glucuronides in the samples was based on their MS in-source fragmentations (m/z 657).

FIG. 6 shows a LC-MS chromatogram 600 of glucuronides of silybin (10 μM) incubated in the absence or presence of testing flavonoids (such as tangeretin and fisetin as well as MK571) in Caco-2 cell monolayers.

FIGS. 7A and 7B show tables 700 and 710 illustrating the effect of test compounds (20 μM) on the glucuronidation of silybin in Caco-2 cells Glucuronide metabolites of silybin were almost undetected with co-incubation of baicalein, resveratrol, diosmetin, morin, luteolin, galangin, and MK-571. Compounds such as fisetin, curcumin, chrysin, quercetin, kaempferol, dihydromyricetin, baicalin, kaempferide, and isorhamnetin had more than 50% inhibition on the glucuronide conjugation of silybin, while chelerythrine, ECG, tangeretin and hesperidin did not significantly inhibit the conjugation as shown in FIGS. 7A and 7B. Tangeretin and baicalein were further evaluated for the bio-enhancing effect on both the pharmacokinetic and therapeutic profile of silybin.

Example 4: Effect of Baicalein and Tangeretin on the Efflux Transport of Silybin in Caco-2 Cells FIGS. 8A, 8B, 8C, 8D, 8E and 8F show graphs 800, 810, 820, 830, 840 and 850 illustrating the inhibitory effect of baicalein or tangeretin at different dosages on the efflux transport of silybin across Caco-2 cell monolayers. The permeability values of silybin A (SBa, A) and silybin B (SBb, B) as well as the efflux ratio (C) of silybin in the absence or the presence of baicalein (BAC) in Caco-2 cells model; the permeability values of silybin A (SBa, D) and silybin B (SBb, E) as well as the efflux ratio (F) of silybin in the absence or the presence of tangeretin (TG) in Caco-2 cells model are shown. (*, P<0.05; , P<0.01; *, P<0.01 vs only treated with silybin. n=3).

FIGS. 9A, 9B, 9C, 9D, 9E and 9F show graphs 900, 910, 920, 930, 940 and 950 illustrating the inhibitory effect of baicalein or tangeretin on bidirectional flux of silybin at different concentrations across Caco-2 cell monolayers. The permeability values of silybin A (SBa, A) and silybin B (SBb, B) as well as the efflux ratio (C) of silybin in the absence or the presence of baicalein (BAC) in Caco-2 cells model; the permeability values of silybin A (SBa, 6D) and silybin B (SBb, 6E) as well as the efflux ratio (6F) of silybin in the absence or the presence of tangeretin (TG) in Caco-2 cells model are shown. (*, P<0.05; , P<0.01; *, P<0.01 vs only treated with silybin. n=3).

As shown in FIGS. 8A-8F, baicalein and tangeretin inhibited the efflux transport of silybin (10 μM) in a dose-dependent manner in the Caco-2 cell monolayers with the lowest effective dosage at 0.5 μM for baicalein and 0.05 μM for tangeretin. The efflux ratio of silybin A and B reduced to 2.4 by 5 μM baicalein and to 1.5 by 0.5 μM tangeretin, respectively. A higher dosage (above 5 μM) for baicalein or higher dosage (above 0.5 μM) for tangeretin revealed similar effects as 5 μM baicalein or 0.5 μM tangeretin, indicating that the inhibition on the efflux of silybin by baicalein and tangeretin could be saturated.

The relationship between the inhibitory effect and the concentrations of silybin (2.5, 5, 10, 20, 30, 40 μM) was evaluated. As shown in FIGS. 9A-9F, 5 μM baicalein significantly inhibited the efflux of silybin with a concentration below 30 μM, but did not affect the efflux of silybin at 40 μM. The efflux ratio of silybin reduced to around 1.0 with 5 μM baicalein co-incubation with 5 μM silybin, similar to the effect of positive control MK571 at 50 μM. Thus, a suitable ratio for co-incubation of silybin and baicalein is 1:1 within a dosage of 40 μM in Caco-2 cell model. The same inhibition trend was observed for 0.5 μM tangeretin incubated with different concentrations of silybin (2.5, 5, 10, 20, 30, 40 μM). With the rising concentration of substrate (silybin), the efflux ratio decreased with co-incubation of 0.5 μM tangeretin. Significant inhibitory effects were observed within 2.5 to 40 μM of silybin by co-incubation of 0.5 μM tangeretin. Tangeretin at 0.5 μM also reduced the efflux ratios of silybin (2.5, 5, and 10 μM) to around 1.0, to the effect of positive control MK571 at 50 μM as shown in FIGS. 9A-9F. Baicalein and tangeretin can significantly inhibit the efflux of silybin in a dose-dependent manner in Caco2 cells.

Example 5: Effect of Baicalein and Tangeretin on the Biliary Excretion of Silybin in Subclinical Hypothyroidism (SCH) Rat Silybin is metabolized to glucuronide and sulfate conjugates and undergoes biliary excretion. As the polarized expression of native transporters and liver metabolism enzymes in the SCH model creates an ideal model for studying hepatobiliary transport, the effect of baicalein and tangeretin on the pharmacokinetics of silybin in rat primary SCH model was studied.

Figure 10:
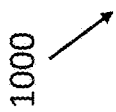
FIG. 10 illustrates the accumulation of silybin in the rat primary sandwich-cultured hepatocytes (SCH) model in accordance with an example embodiment.

FIG. 10 shows a table 1000 illustrating the accumulation of silybin in the SCH model.

FIGS. 11A, 11B, 11C, 11D, 11E and 11F show graphs 1100, 1110, 1120, 1130, 1140 and 1150 illustrating the BEI and $CL_{bile,int}$ value of silybin on the SCH model in the absence and presence of baicalein (BAC) or tangeretin (TG) at different concentrations. The BEI % value of free silybin (A, D) and total silybin (B, E) significantly decreased after treatment with baicalein or tangeretin in a dose-dependent manner as well as the $CL_{bile,int}$ value of free silybin (C, F). (*, P<0.05; , P<0.01; *, P<0.01 vs only treatment with silybin. n=3).

FIGS. 12A, 12B, 12C, 12D, 12E and 12F show graphs 1200, 1210, 1220, 1230, 1240 and 1250 illustrating the effect of baicalein (BAC, 15.8 μM) or tangeretin (TG, 5 μM) on the BEI and $CL_{bile,int}$ value of silybin (at 2.5, 5, 10 and 20 μM) on the SCH model. The BEI % value of free silybin (A, D) and total silybin (B, E) significantly decreased after treatment with baicalein or tangeretin in a dose-dependent manner as well as the $CL_{bile,int}$ value of free silybin (C, F). (*, P<0.05; , P<0.01; *, P<0.01 vs only treatment with silybin. n=3).

The cellular uptake of silybin in rat hepatocytes was in a concentration-dependent manner as shown in FIG. 10. Biliary accumulation of silybin was measured in the absence and in the presence of $Ca^{2+}/Mg^{2+}$ in the extracellular medium. Using B-CLEAR technology, the BEI and $Cl_{biliary}$ were calculated by taking into account the accumulation differences under these conditions. As illustrated in FIGS. 11A-11F, the mean BEI for free silybin A and silybin B (100) in rat hepatocytes was 35±4% and 33±1%, and the mean BEI for total silybin A and B (10 μM) in rat hepatocytes was 33±0.8% and 32±1%.

Figure 11A:
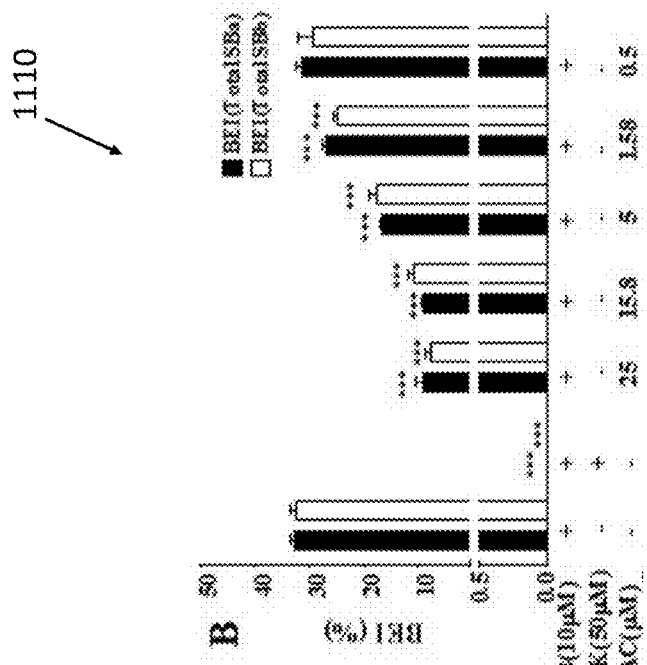
FIG. 11A illustrates the biliary excretion index (BEI) value of silybin on the subclinical hypothyroidism (SCH) model in the absence or presence of baicalein (BAC) at different concentrations in accordance with an example embodiment.
Figure 11B:
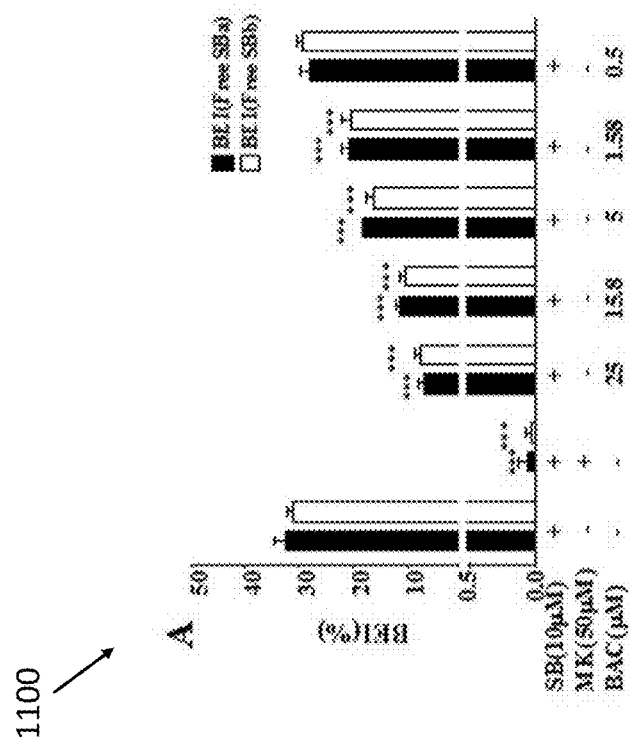
FIG. 11B illustrates the biliary excretion index (BEI) value of silybin on the subclinical hypothyroidism (SCH) model in the absence or presence of baicalein (BAC) at different concentrations in accordance with an example embodiment.
Figure 11D:
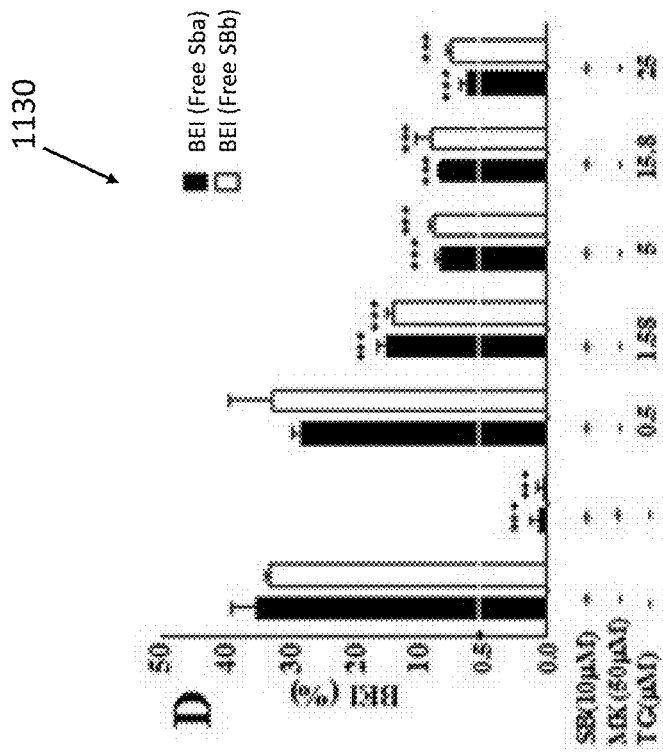
FIG. 11D illustrates the biliary excretion index (BEI) value of silybin on the subclinical hypothyroidism (SCH) model in the absence or presence of tangeretin (TG) at different concentrations in accordance with an example embodiment.
Figure 11C:
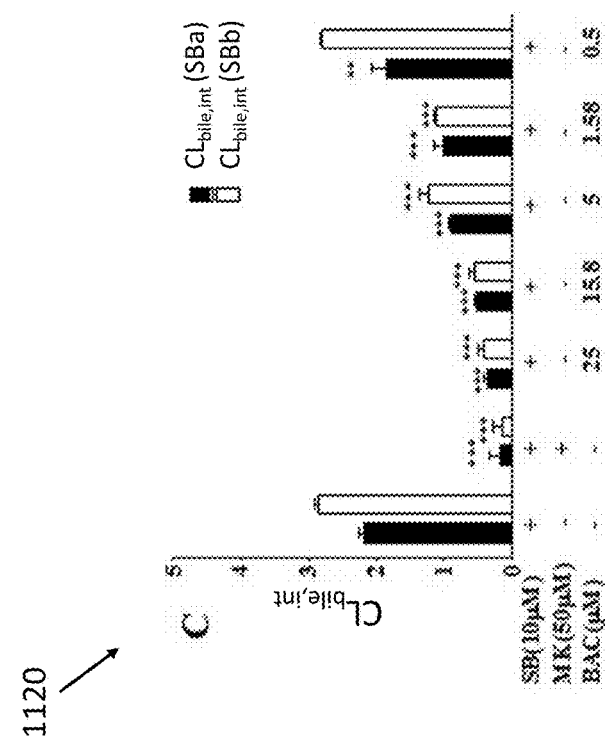
FIG. 11C illustrates the instinct biliary clearance ($CL_{bile,int}$) value of silybin on the subclinical hypothyroidism (SCH) model in the absence or presence of baicalein (BAC) at different concentrations in accordance with an example embodiment.
Figures 11E, 11F:
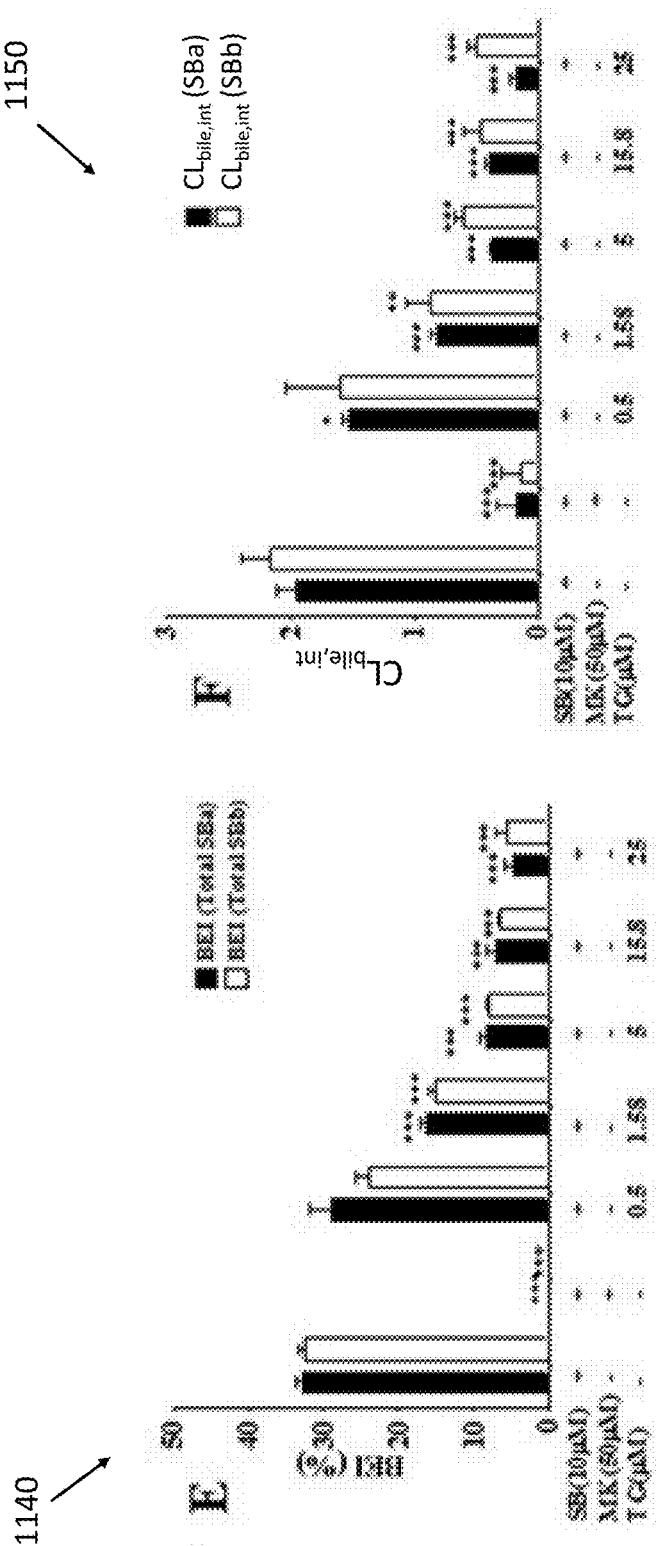
FIG. 11E illustrates the biliary excretion index (BEI) value of silybin on the subclinical hypothyroidism (SCH) model in the absence or presence of tangeretin (TG) at different concentrations in accordance with an example embodiment.
FIG. 11F illustrates the instinct biliary clearance ($CL_{bile,int}$) value of silybin on the subclinical hypothyroidism (SCH) model in the absence or presence of tangeretin (TG) at different concentrations in accordance with an example embodiment.
Figures 12A, 12B:
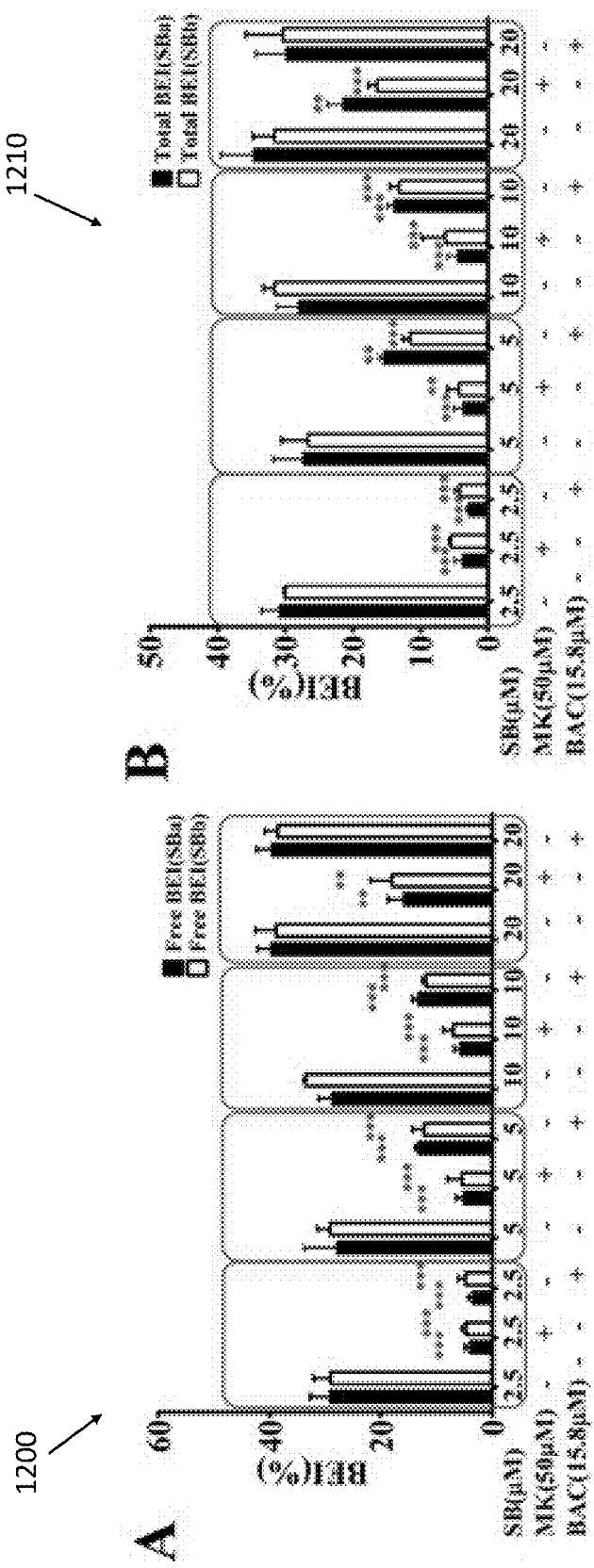
FIG. 12A illustrates the effect of baicalein (BAC) on the biliary excretion index (BEI) value of silybin on the subclinical hypothyroidism (SCH) model in accordance with an example embodiment.
FIG. 12B illustrates the effect of baicalein (BAC) on the biliary excretion index (BEI) value of silybin on the subclinical hypothyroidism (SCH) model in accordance with an example embodiment.
Figure 12D:
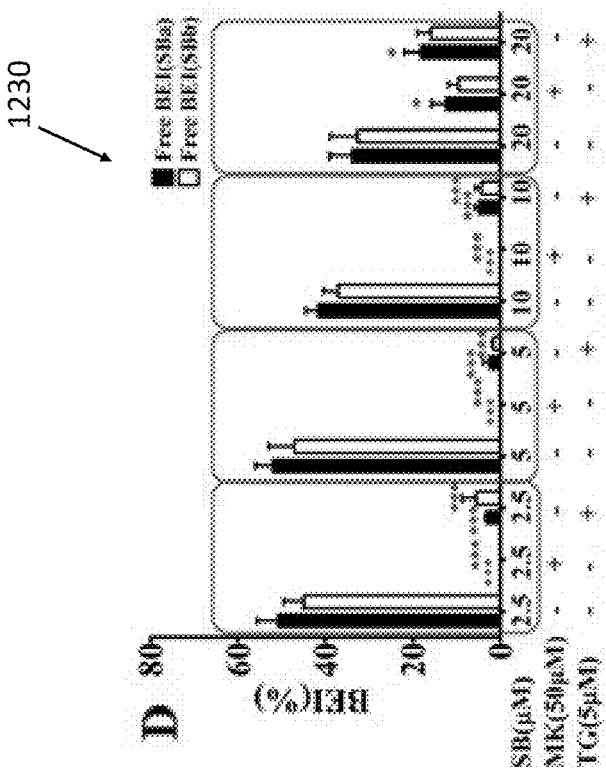
FIG. 12D illustrates the effect of tangeretin (TG) on the biliary excretion index (BEI) value of silybin on the subclinical hypothyroidism (SCH) model in accordance with an example embodiment.
Figure 12C:
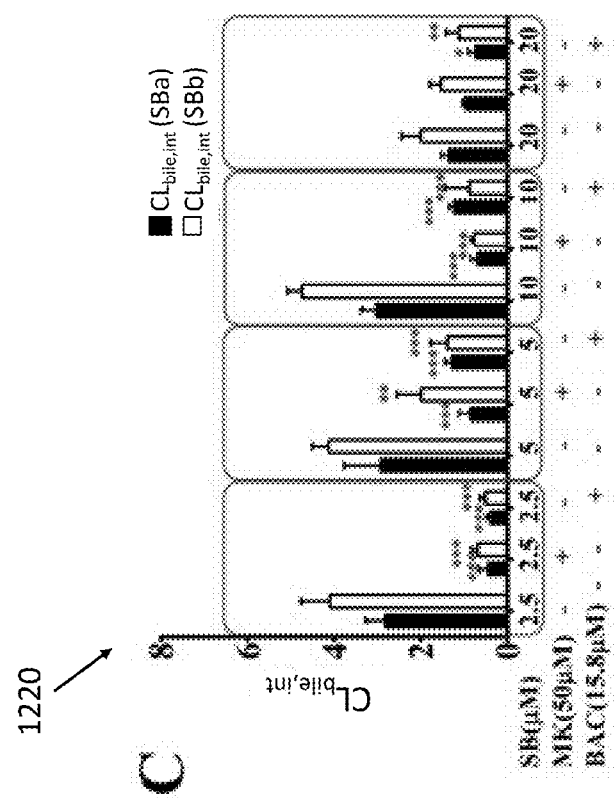
FIG. 12C illustrates the effect of baicalein (BAC) on the instinct biliary clearance ($CL_{bile,int}$) value of silybin on the subclinical hypothyroidism (SCH) model in accordance with an example embodiment.
Figures 12E, 12F:
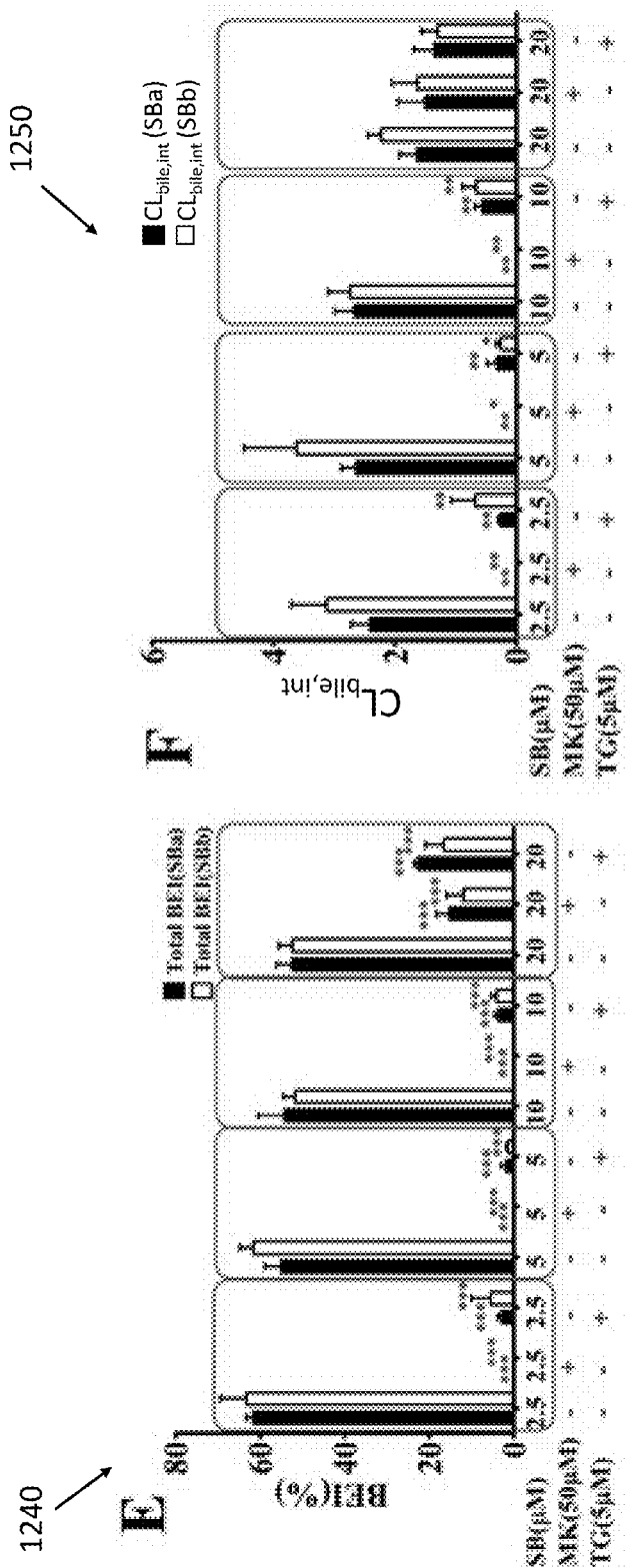
FIG. 12E illustrates the effect of tangeretin (TG) on the biliary excretion index (BEI) value of silybin on the subclinical hypothyroidism (SCH) model in accordance with an example embodiment.
FIG. 12F illustrates the effect of tangeretin (TG) on the instinct biliary clearance ($CL_{bile,int}$) value of silybin on the subclinical hypothyroidism (SCH) model in accordance with an example embodiment.
Figures 13A, 13B:
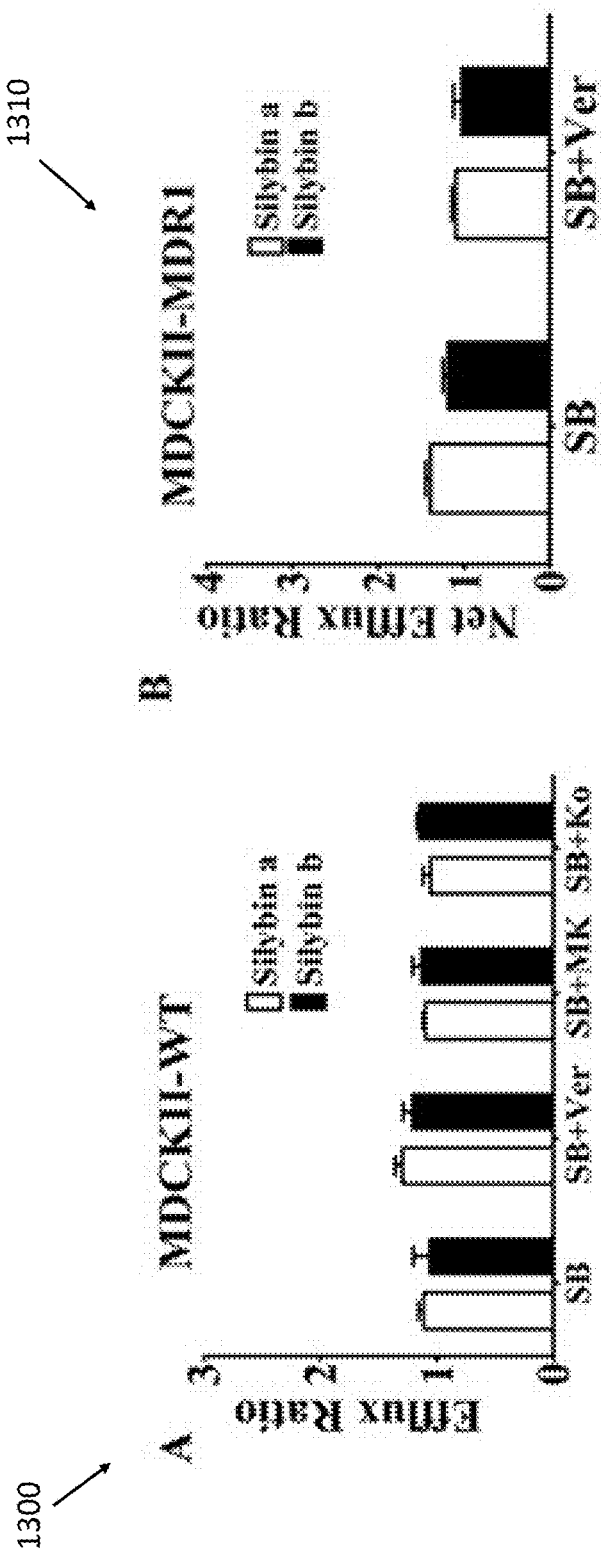
FIG. 13A illustrates the transport of silybin across the Madin-Darby canine kidney II-wild type (MDCKII-WT) cell line in accordance with an example embodiment.
FIG. 13B illustrates the transport of silybin across the Madin-Darby canine kidney II-multidrug resistance gene 1 (MDCKII-MDR1) cell line in accordance with an example embodiment.
Figures 14A, 14B:
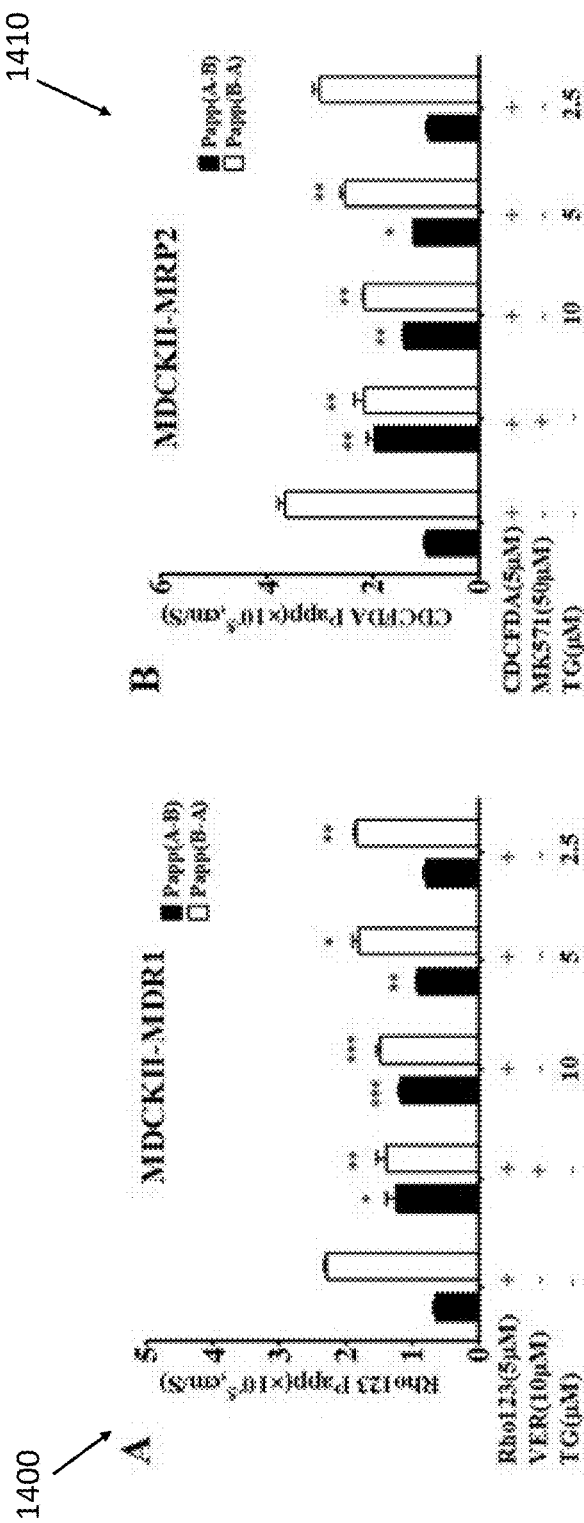
FIG. 14A illustrates the effect of tangeretin (TG) on the function of efflux transporter multi-drug resistance gene 1 (MDR1) overexpressing Madin-Darby canine kidney II cell monolayers in accordance with an example embodiment.
FIG. 14B illustrates the effect of tangeretin (TG) on the function of efflux transporter multidrug resistance-associated protein 2 (MRP2) overexpressing Madin-Darby canine kidney II cell monolayers in accordance with an example embodiment.
Figures 14C, 14D:
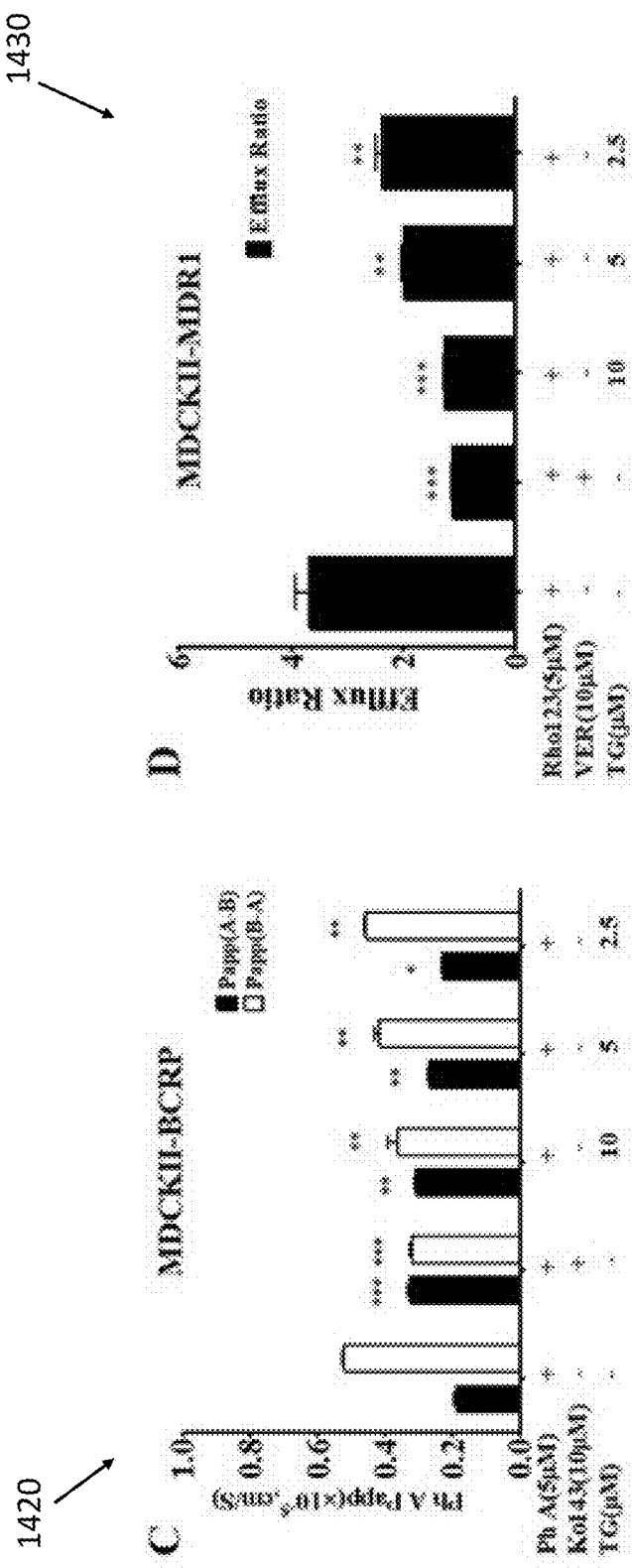
FIG. 14C illustrates the effect of tangeretin (TG) on the function of efflux transporter breast cancer resistance protein (BCRP) overexpressing Madin-Darby canine kidney II cell monolayers in accordance with an example embodiment.
FIG. 14D illustrates the effect of tangeretin (TG) on the function of efflux transporter multi-drug resistance gene 1 (MDR1) overexpressing Madin-Darby canine kidney II cell monolayers in accordance with an example embodiment.
Figures 14E, 14F:
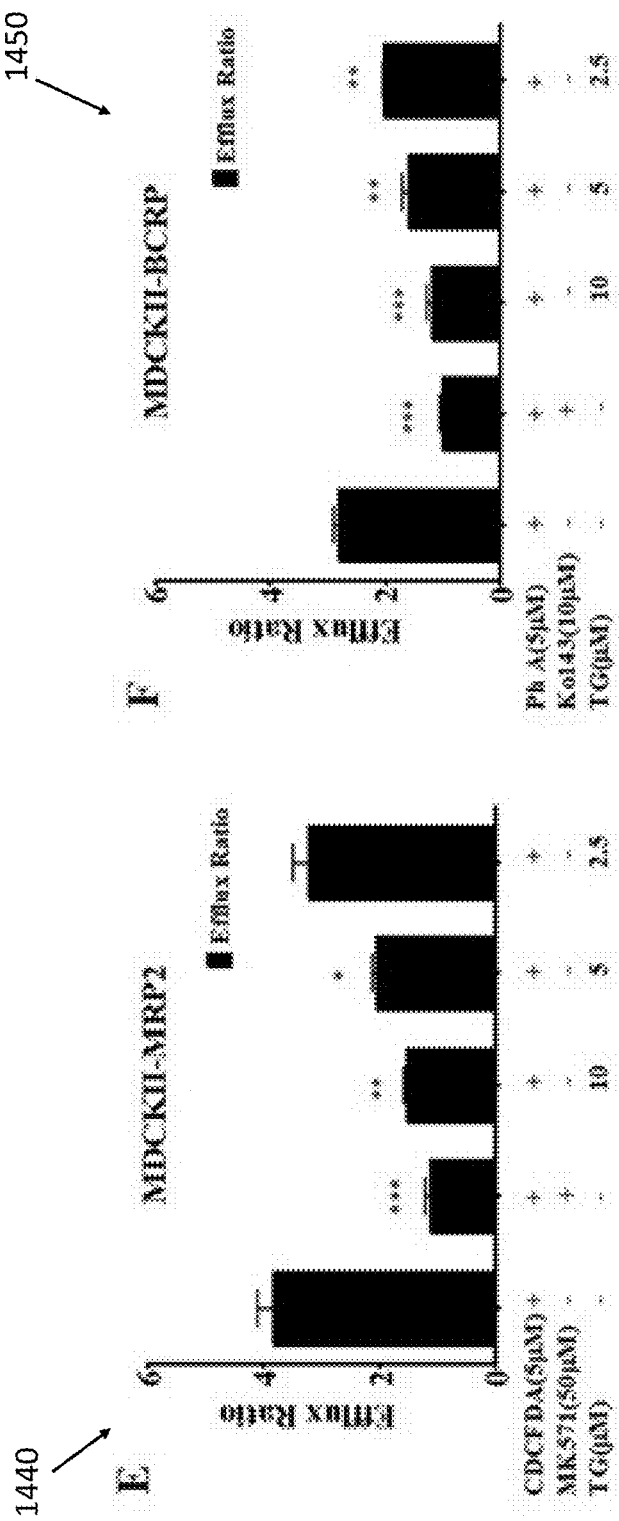
FIG. 14E illustrates the effect of tangeretin (TG) on the function of efflux transporter multidrug resistance-associated protein 2 (MRP2) overexpressing Madin-Darby canine kidney II cell monolayers in accordance with an example embodiment.
FIG. 14F illustrates the effect of tangeretin (TG) on the function of efflux transporter breast cancer resistance protein (BCRP) overexpressing Madin-Darby canine kidney II cell monolayers in accordance with an example embodiment.
Figures 15A, 15B:
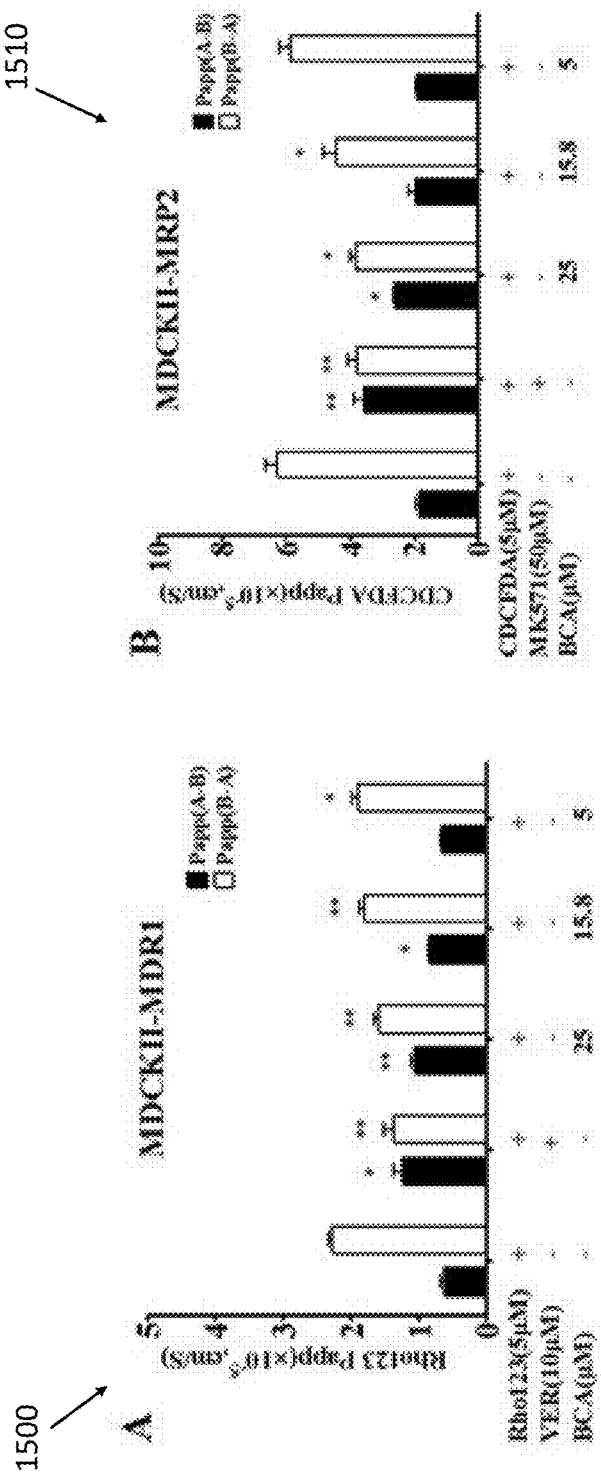
FIG. 15A illustrates the effect of baicalein (BCA) on the function of MDR1 overexpressing MDCK II cell monolayers in accordance with an example embodiment.
FIG. 15B illustrates the effect of baicalein (BCA) on the function of MRP2 overexpressing MDCK II cell monolayers in accordance with an example embodiment.
Figures 15E, 15F:
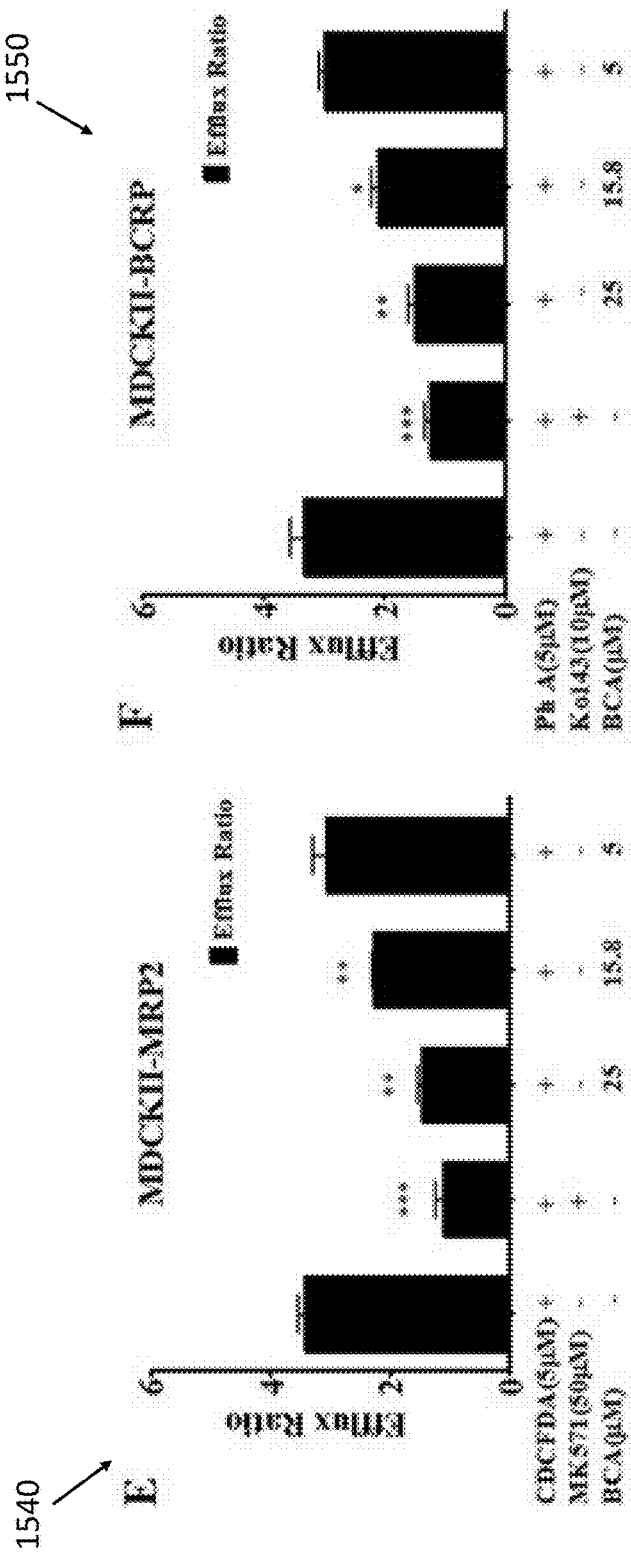
FIG. 15E illustrates the effect of baicalein (BCA) on the function of MRP2 overexpressing MDCK II cell monolayers in accordance with an example embodiment.
FIG. 15F illustrates the effect of baicalein (BCA) on the function of BCRP overexpressing MDCK II cell monolayers in accordance with an example embodiment.
Figure 16B:
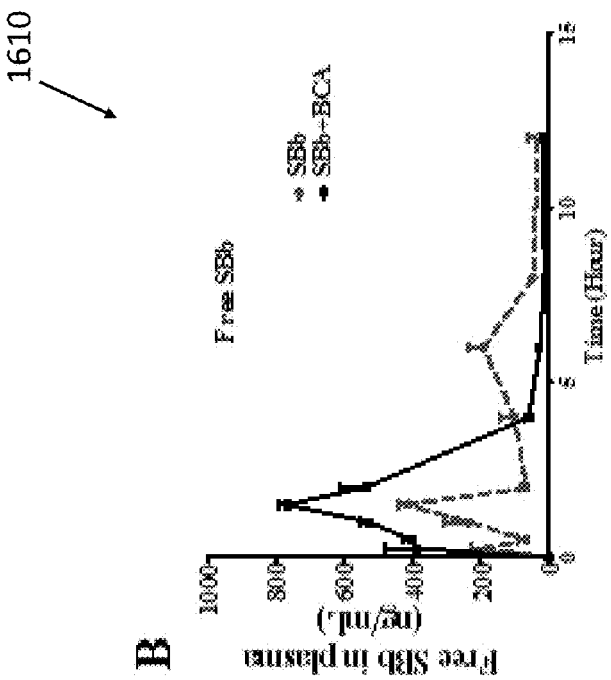
FIG. 16B illustrates the mean plasma concentration-time profile for 10 mg/kg silybin with or without simultaneous oral administration of 10 mg/kg BCA in accordance with an example embodiment.
Figure 16A:
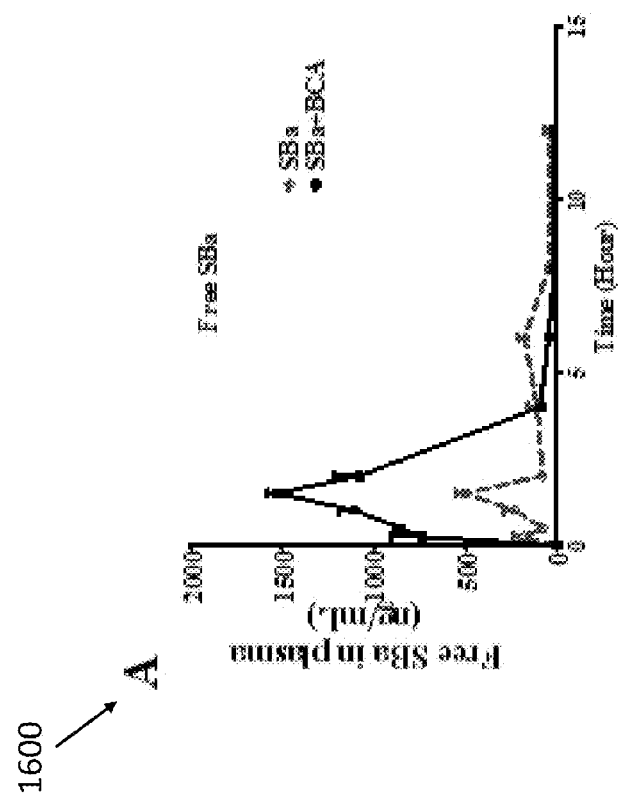
FIG. 16A illustrates the mean plasma concentration-time profile for 10 mg/kg silybin with or without simultaneous oral administration of 10 mg/kg BCA in accordance with an example embodiment.
Figure 16D:
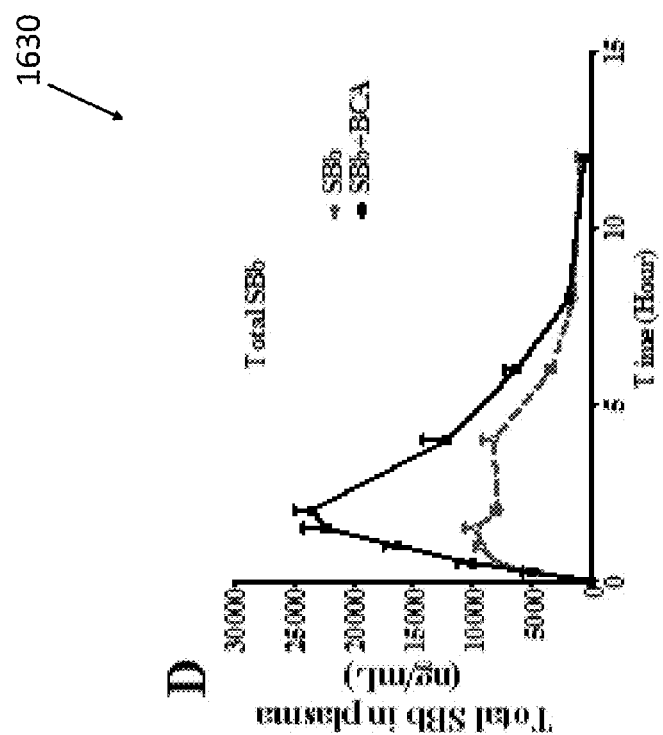
FIG. 16D illustrates the mean plasma concentration-time profile for 10 mg/kg silybin with or without simultaneous oral administration of 10 mg/kg BCA in accordance with an example embodiment.
Figure 16C:
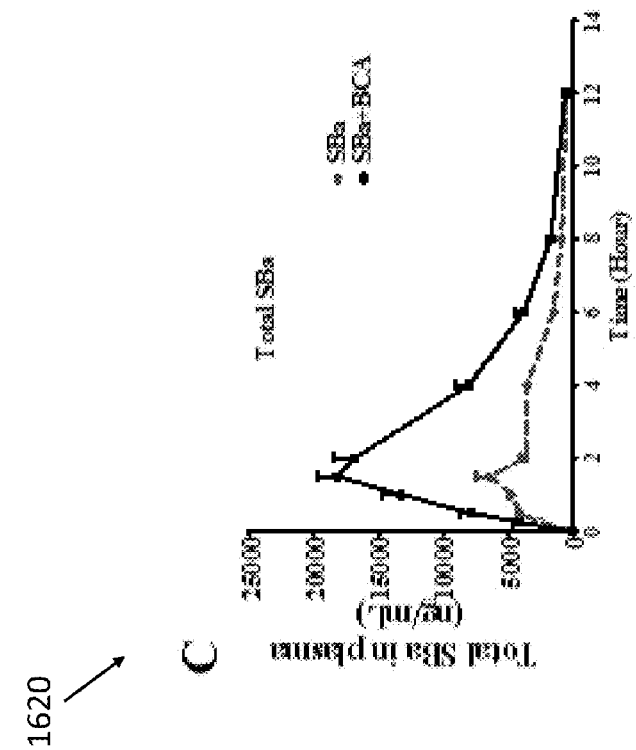
FIG. 16C illustrates the mean plasma concentration-time profile for 10 mg/kg silybin with or without simultaneous oral administration of 10 mg/kg BCA in accordance with an example embodiment.
Figure 19D:
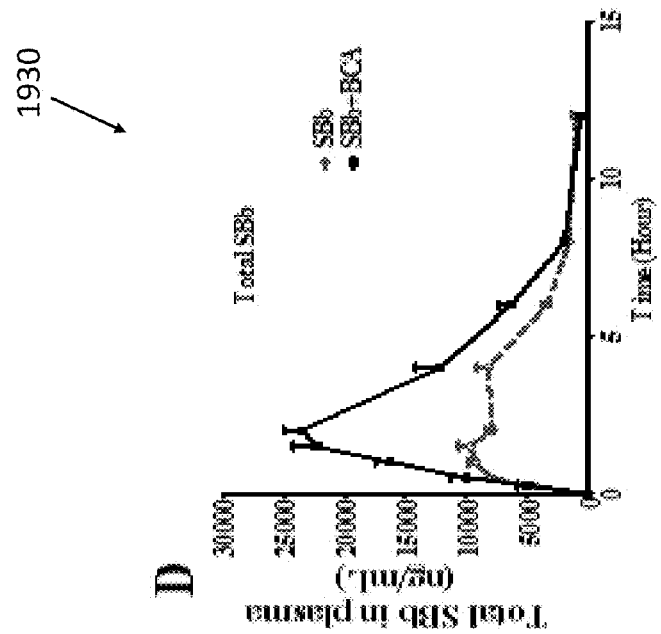
FIG. 19D illustrates the mean plasma concentration-time profile for 50 mg/kg silybin with or without simultaneous oral administration of 50 mg/kg BCA in accordance with an example embodiment.
Figure 19C:
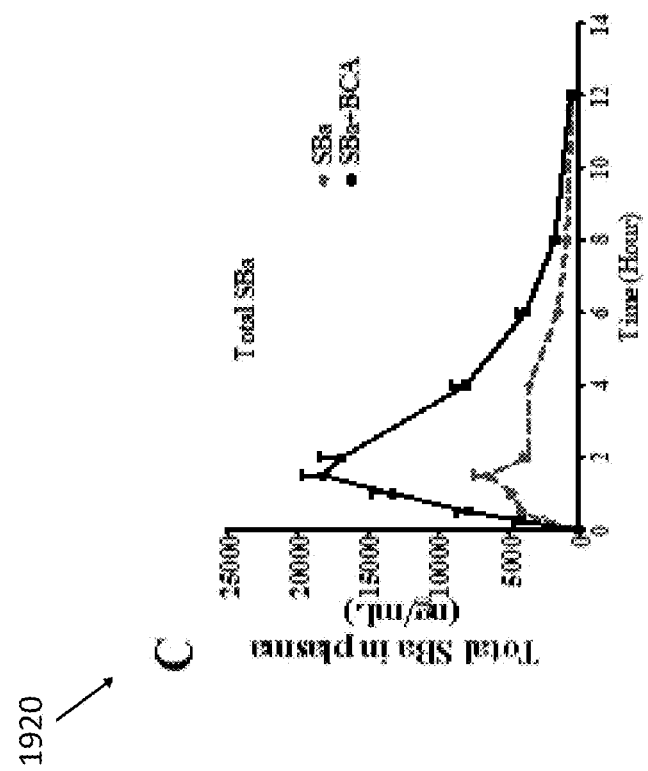
FIG. 19C illustrates the mean plasma concentration-time profile for 50 mg/kg silybin with or without simultaneous oral administration of 50 mg/kg BCA in accordance with an example embodiment.
Figure 24D:
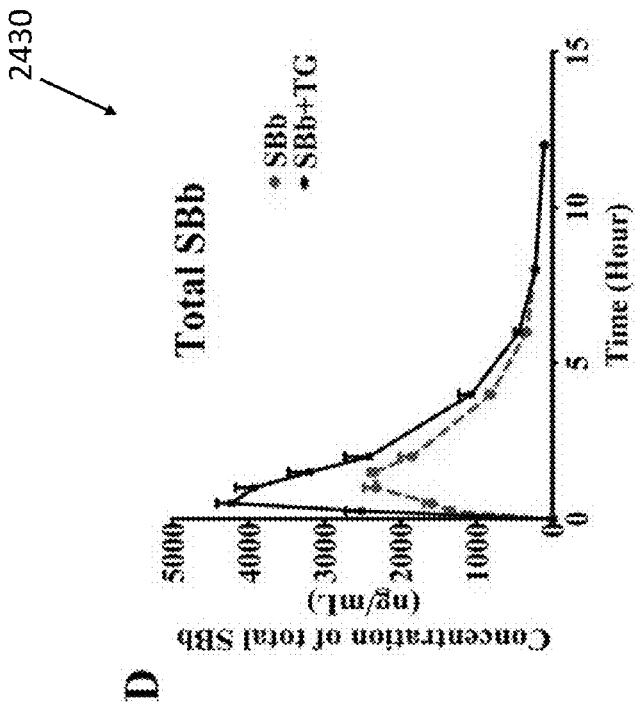
FIG. 24D illustrates the mean plasma concentration-time profile for 10 mg/kg silybin with or without simultaneous oral administration of 10 mg/kg tangeretin (TG) in accordance with an example embodiment.
Figure 24C:
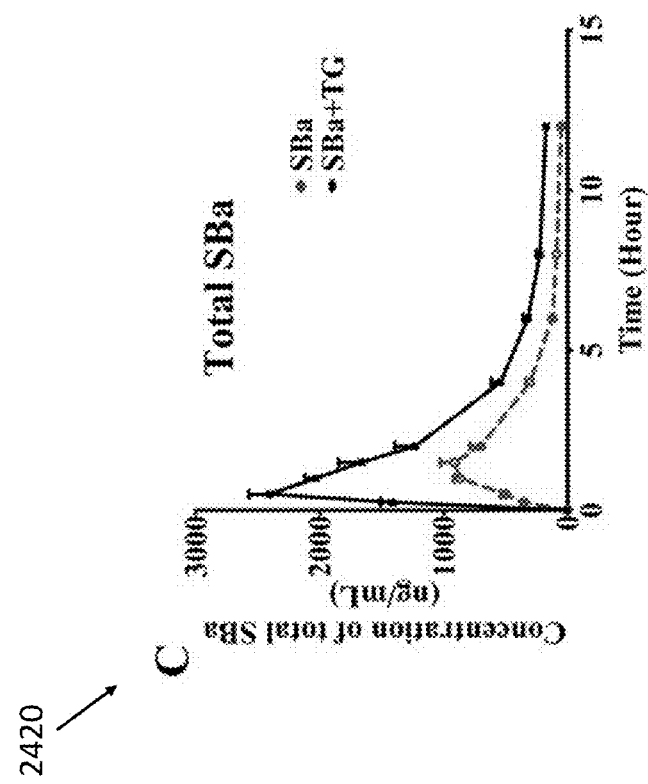
FIG. 24C illustrates the mean plasma concentration-time profile for 10 mg/kg silybin with or without simultaneous oral administration of 10 mg/kg tangeretin (TG) in accordance with an example embodiment.

The biliary excretion of silybin was inhibited by 100% with the MRPs inhibitor 50 μM MK571, consistent with the reported result about the primary role for MRP2 in the biliary elimination of silymarin flavonolignan as well as its conjugates. Co-incubation with baicalein at 25 μM significantly reduced the biliary excretion of silybin (10 μM) about ~75% (P<0.001) (FIGS. 11A, 11B, 11C). Likewise, tangeretin significantly inhibited silybin biliary efflux about 90% (P<0.001) in hepatocyte in a dose-dependent manner.

The intrinsic biliary clearance values from in vitro incubations of silybin with rat SCH were 2.1±0.2 μl/(min·mg protein) for silybin A and 2.5±0.4 μl/(min·mg protein) for silybin B. Baicalein and tangeretin inhibited the biliary clearance of silybin (at 2.5, 5 and 10 μM) in day 4 sandwich-cultured hepatocytes in a concentration-dependent manner (FIGS. 12A-12F).

Example 6: Transcellular Transport of Silybin Across MDCKII—MRP2/BCRP/MDR1 Cells The efflux transporter transfected cell line MDCKII-MRP2, MDCKII-BCRP, MDCKII-MDR1, and MDCKII-WT was used to identify the efflux transporter for silybin and study the underlying mechanism for the results observed in Caco-2 cells.

FIGS. 13A, 13B, 13C and 13D show graphs 1300, 1310, 1320 and 1330 illustrating transport of silybin across MDCKII-WT as compared to transfected cell lines. 13A shows MDCKII-WT in the absence or in the presence of efflux inhibitors (verapamil, MK-571 and Ko143), 13B shows MDCKII-MDR1 in the absence and presence of verapamil, a specific P-gp efflux inhibitor, 13C shows MDCKII-MRP2 in the absence and presence of MK-571, a specific MRP family inhibitor and 13D shows MDCKII-BCRP in the absence and presence of KO143, a specific MRP family inhibitor.

Directional transport of silybin A and B across MDCKII-WT cells in the absence of efflux inhibitors was at a similar rate as mean net efflux ratios at 1.01 for silybin A and 0.99 for silybin B. There was no significant difference in the permeability of silybin in the absence or presence of P-gp, MRP and BCRP efflux inhibitors (FIGS. 13A-13D) in both A and B directions as compared to control, indicating minimal expressions of efflux transporters in MDCKII-WT cells.

Silybin permeabilities and the respective efflux ratios (ER) obtained in the MDCKII-MRP2 transfected cell line are presented in FIGS. 13A-13D. The mean net efflux ratios of silybin in MDCKII-MRP2 are 3.06 for silybin A, and 3.30 for silybin B in the absence of any inhibitor. However, the efflux ratio of silybin was essentially abolished in the presence of MK571 (50 µM), which was caused by a significant increase of A-B transport (p<0.001). These results show that silybin is a MRP2 substrate.

The B-A direction transport of silybin was significantly higher than in the A-B direction in MDCKII-BCRP cells, while its net efflux ratio significantly reduced from 2.96 for silybin A and 3.04 for silybin B to 1.31 for silybin A and 1.04 for silybin B by incubation with Ko143 (10 µM). MDCKII-MDR1 cells did not exhibit significant directional transport of silybin. Net efflux ratio for silybin transport were found to be 1.39 for silybin A and 1.20 for silybin B in the absence of any inhibitor, and 1.10 for silybin A, 1.04 for silybin B in the presence of verapamil (10 µM). Consistent with the results observed in the Caco-2 cell monolayer, the P-gp inhibitor verapamil did not affect the bio-direction transport of silybin in MDCKII-MDR1 cell.

The differences in ER values of silybin transport across MDCKII-WT cells relative to MRP2 and BCRP transfected cell lines are highly significant. Such differences imply an increased efflux of silybin by MRP2 and BCRP respectively due to enhanced expression of these transporters in these cell lines. The ER values in MDCKII-MDR1 and MDCKII-MRP2 cell lines were reduced to almost 1.0 in presence of efflux inhibitors, which suggest that silybin is a substrate for both MRP2 and BCRP efflux proteins. However, MDR1 (P-gp) did not produce substantial differences in directional transport of silybin as compared to MDCKII-WT cells, which indicate that silybin is not a substrate for MDR1 (P-gp) efflux transporter.

Example 7: Inhibitory Effect of Tangeretin and Baicalein on Efflux Transporter(s)

FIGS. 14A, 14B, 14C, 14D, 14E and 14F show graphs 1400, 1410, 120, 1430, 1440 and 1450 illustrating the effect of tangeretin (TG) on the function of efflux transporters in MDR1, MRP2, and BCRP overexpressing MDCKII cell monolayers. The permeability values (A) and corresponding efflux ratios (D) of Rho123 (a specific substrate of P-gp) were compared in MDCKII-MDR1 cells in the absence and presence of tangeretin; the permeability values (B) and corresponding efflux ratios (E) of CDCFDA (a specific substrate of MRP2) were compared in MDCKII-MRP2 cells in the absence and presence of tangeretin; and the permeability values (C) and corresponding efflux ratios (F) of Ph A (a specific substrate of BCRP) were compared in MDCKII-BCRP cells in the absence and presence of tangeretin. (*, P<0.05;, P<0.01; *, P<0.001 vs absence of any inhibitor. n=3).

FIGS. 15A, 15B, 15C, 15D, 15E and 15F show graphs 1500, 1510, 1520, 1530, 1540 and 1550 illustrating the effect of baicalein (BCA) on the function of efflux transporters in MDR1, MRP2, and BCRP overexpressing MDCKII cell monolayers. The permeability values (A) and corresponding efflux ratios (D) of Rho123 (a specific substrate of P-gp) were compared in MDCKII-MDR1 cells in the absence and presence of baicalein; the permeability values (B) and corresponding efflux ratios (E) of CDCFDA (a specific substrate of MRP2) was compared in MDCKII-MRP2 cells in the absence and presence of baicalein; and the permeability values (C) and corresponding efflux ratios (F) of Ph A (a specific substrate of BCRP) was compared in MDCKII-BCRP cells in the absence and presence of baicalein. (*, P<0.05;, P<0.01; *, P<0.001 vs absence of any inhibitor. n=3).

The mean efflux ratio for specific MRP2 substrate CDCFDA was 3.82 in the MDCKII-MRP2 cells, and decreased to 1.11 in the presence of MK571 (MRP2 inhibitor) proving the suitability of MDCKII-BCRP cell monolayer for use in investigating the effect of BCRP in vitro (FIGS. 14A-14F and 15A-15F). The efflux ratio for CDFDA in the MDCKII-MRP2 cells decreased to 1.54 and 1.46 with treatment of tangeretin (FIGS. 14A-14F) or baicalein (FIGS. 15A-15F), indicating tangeretin and baicalein are MRP2 inhibitors. The $IC_{50}$ for tangeretin for inhibiting the efflux of CDCFDA was 8.84 µM in MDCKII-MRP2 cells. The $IC_{50}$ for baicalein for inhibiting the efflux of CDCFDA was 21.21 µM in MDCKII-MRP2 cells.

The mean efflux ratio for the pheophorbide A (Ph A, BCRP-specific substrate) was 2.82 in MDCKII-BCRP cells, and decreased to 0.99 in the presence of Ko143 (BCRP inhibitor) (FIGS. 14A-14F). With the treatment of tangeretin (FIGS. 14A-14F) or baicalein (FIGS. 15A-15F), the mean efflux ratio for Ph A decreased to 1.18 and 1.48, indicating tangeretin and baicalein are BCRP inhibitors. The $IC_{50}$ for tangeretin to inhibit the efflux of Ph A was 8.88 µM in MDCKII-BCRP cells. The $IC_{50}$ for baicalein to inhibit the efflux of Ph A was 22.15 µM.

The MDCKII-MDR1 cells monolayer model was validated by examining the bidirectional transport of Rho123 first. A predominantly B-A transport of Rho123 was observed with mean efflux ratio at 3.03 which was significantly reduced by 10 µM verapamil (MDR1 inhibitor), demonstrating the suitability of MDCKII-MDR1 cell monolayer for investigating the function of P-gp in vitro. The efflux ratio for Rho123 in the MDCKII-MDR1 cells decreased to 1.26 and 1.49 with the treatment of tangeretin (FIGS. 14A-14F) or baicalein (FIGS. 15A-15F), indicating tangeretin and baicalein are MDR1 inhibitors, consistent with previous findings. The $IC_{50}$ for tangeretin for inhibiting the efflux of Rho123 was 6.88 µM in MDCKII-MDR1 cells, while the $IC_{50}$ for baicalein to inhibit the efflux of Rho123 was 20.59 µM in MDCKII-MDR1 cells.

Example 8: Effects of Baicalein on Pharmacokinetics of Silybin in Rats

The effects of baicalein on the bioavailability and pharmacokinetics of silybin as well as its major metabolites were investigated in rats. In this study, silybin was administered orally at dosages of 10 mg/kg or 50 mg/kg with or without co-administration of baicalein at the same dosages. A developed and validated LC-MS method was successfully used for determining the concentrations of free and total silybin in the pharmacokinetic studies. The pharmacokinetic parameters of analytes were calculated with non-compartmental analysis.

FIGS. 16A, 16B, 16C and 16D show graphs 1600, 1610, 1620 and 1630 illustrating the mean plasma concentration-time profiles for 10 mg/kg silybin with or without simultaneous oral administration of 10 mg/kg baicalein. Significantly increased absorption of free silybin A (SBa, FIG. 16A), free silybin B (SBb, FIG. 16B), total silybin A (FIG. 16C), and total silybin B (FIG. 16D) were observed with co-administration of baicalein.

FIG. 17 shows a table 1700 illustrating mean pharmacokinetic parameters of free silybin after oral administration at a dose of 10 mg/kg with or without simultaneous oral administration of 10 mg/kg baicalein to rats.

FIG. 18 shows a table 1800 illustrating mean pharmacokinetic parameters of total silybin after oral administration at a dose of 10 mg/kg with or without simultaneous oral administration of 10 mg/kg baicalein to rats.

FIGS. 19A, 19B, 19C and 19D show graphs 1900, 1910, 1920, 1930 illustrating the mean plasma concentration-time profiles for 50 mg/kg silybin with or without simultaneous oral administration of 50 mg/kg baicalein (n=6). Significantly increased absorption for free silybin A (SBa, FIG. 19A), free silybin B (SBb, FIG. 19B), total silybin A (FIG. 19C), and total silybin B (FIG. 19D) were observed with co-administration of baicalein.

FIG. 20 shows a table 2000 illustrating the mean pharmacokinetic parameters of free silybin after oral administration at a dose of 50 mg/kg with or without simultaneous oral administration of 50 mg/kg baicalein to rats.

FIG. 21 shows a table 2100 illustrating the mean pharmacokinetic (PK) parameters of total silybin after oral administration at a dose of 50 mg/kg with or without simultaneous oral administration of 50 mg/kg baicalein to rats.

FIGS. 16A-16D and 19A-19D show the plasma concentration-time profiles of free and total silybin A and B after oral administration at a dose of 10 mg/kg and 50 mg/kg in rats with or without baicalein (10 mg/kg or 50 mg/kg). The oral PK parameters of free silybin are summarized in FIG. 17 and FIG. 20, while the oral PK parameters of total silybin are summarized in FIG. 18 and FIG. 20. In single administration group, the Cmax of free silybin A and B reached 26±13 and 16±5 ng/ml, while the mean Cmax of total silybin A and B included parent (free) silybin and its sulfate and glucuronide conjugates were 1109±158 and 2478±284 ng/ml. These results indicate that about 97% silybin A and 99% silybin B existed as conjugates in rat plasma. The area under the plasma concentration-time curve (AUC (0-t)) of silybin (10 mg/kg) in the presence of baicalein (10 mg/kg) significantly ($P<0.001$) increased by 19.38-fold for free SBa, 5.46-fold for free SBb, 3.73-fold for total SBa, and 1.93-fold for total SBb; and the peak concentration (Cmax) was significantly increased by 16.08-fold for free SBa, 8.50-fold for free SBb. 2.69-fold for total SBa, and 1.98-fold for total SBb.

The plasma concentration-time curves for silybin (50 mg/kg) in the presence of baicalein (50 mg/kg) show significantly enhanced absorption in comparison to single administration of silybin in Figure FIGS. 19A-19D. The plasma AUC (0-t) of silybin in the presence of baicalein was significantly ($P<0.001$) increased by 2.74-fold for free SBa, 1.51 fold for free SBb, 2.08-fold for total SBa, and 1.83-fold for total SBb; and the Cmax significantly increased by 3.01-fold for free SBa, 2.22-fold for free SBb, 2.83-fold for total SBa, and 2.43-fold for total SBb. However, there was no significant change for the t1/2, Tmax and clearance CLz/F (l/h/kg) of silybin in the presence of baicalein. Additionally, there were no significant changes in the pharmacokinetic parameters of baicalein (data not shown) after co-administration of baicalein with silybin compared with that of single administration of baicalein. Therefore, oral co-administration of baicalein significantly increased plasma concentrations of silybin as well as its conjugates, indicating enhanced bioavailability of silybin in vivo.

Example 9: Effects of Tangeretin on the Pharmacokinetics of Silybin in SD Rats

FIG. 22 shows a table 2200 illustrating mean pharmacokinetic parameters of free silybin at dosage of 10 mg/kg with or without simultaneous oral administration of 10 mg/kg tangeretin to rats.

FIG. 23 shows a table 2300 illustrating mean pharmacokinetic parameters of total silybin at a dose of 10 mg/kg with or without simultaneous oral administration of 10 mg/kg tangeretin to rats.

FIGS. 24A, 24B, 24C and 24D show graphs 2400, 2410, 2420 and 2430 illustrating mean plasma concentration-time profiles of silybin in rats after a single oral administration dose of silybin (10 mg/kg) and in combination with tangeretin (10 mg/kg). (Each point represents the mean±SD of 6 rats). Significantly increased absorption of free silybin A (SBa, figure A), free silybin B (SBb, figure B), total silybin A (figure C), and total silybin B (figure D) were observed with co-administration of tangeretin.

Figure 25:
FIG. 25 illustrates the mean pharmacokinetic parameters of free silybin after oral administration at a dose of 50 mg/kg with or without simultaneous oral administration of 50 mg/kg tangeretin in rats in accordance with an example embodiment.

FIG. 25 shows a table 2500 illustrating mean pharmacokinetic parameters of free silybin at a dose of 50 mg/kg with or without simultaneous oral administration of 50 mg/kg tangeretin to rats.

Figure 26:
FIG. 26 illustrates the mean pharmacokinetic parameters of total silybin after oral administration at a dose of 50 mg/kg with or without simultaneous oral administration of 50 mg/kg tangeretin in rats in accordance with an example embodiment.
Figure 27B:
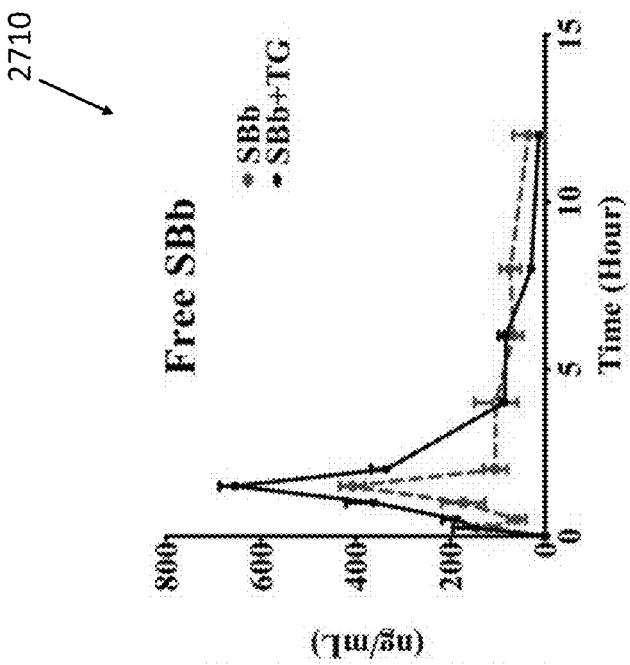
FIG. 27B illustrates the mean plasma concentration-time profile for 50 mg/kg silybin and in combination with 50 mg/kg tangeretin (TG) in accordance with an example embodiment.
Figure 27A:
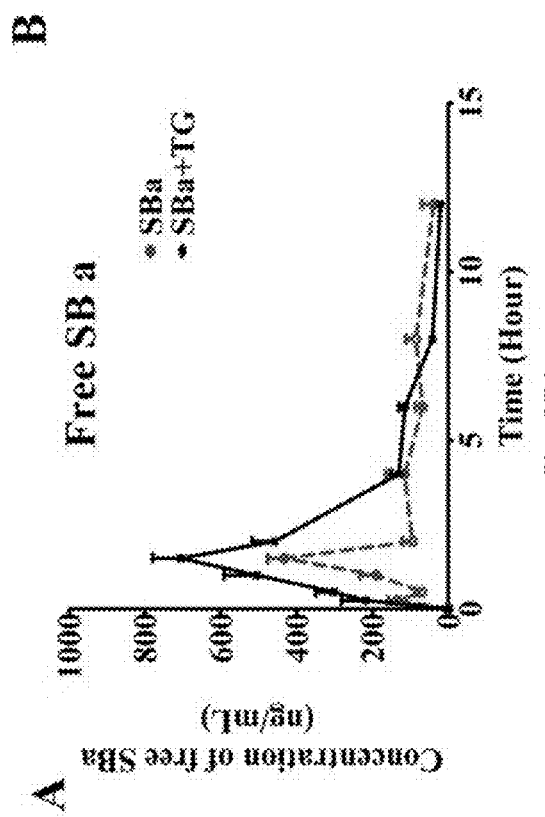
FIG. 27A illustrates the mean plasma concentration-time profile for 50 mg/kg silybin and in combination with 50 mg/kg tangeretin (TG) in accordance with an example embodiment.
Figure 27D:
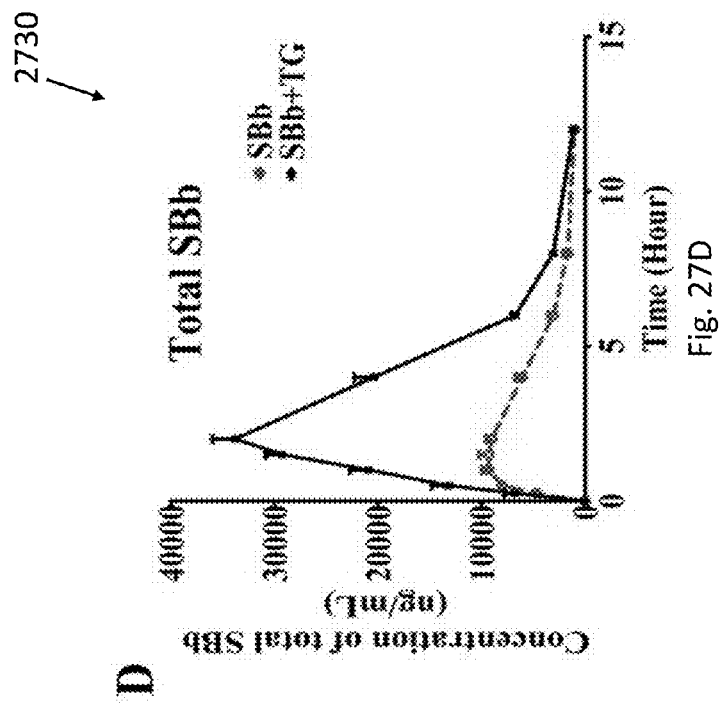
FIG. 27D illustrates the mean plasma concentration-time profile for 50 mg/kg silybin and in combination with 50 mg/kg tangeretin (TG) in accordance with an example embodiment.
Figure 27C:
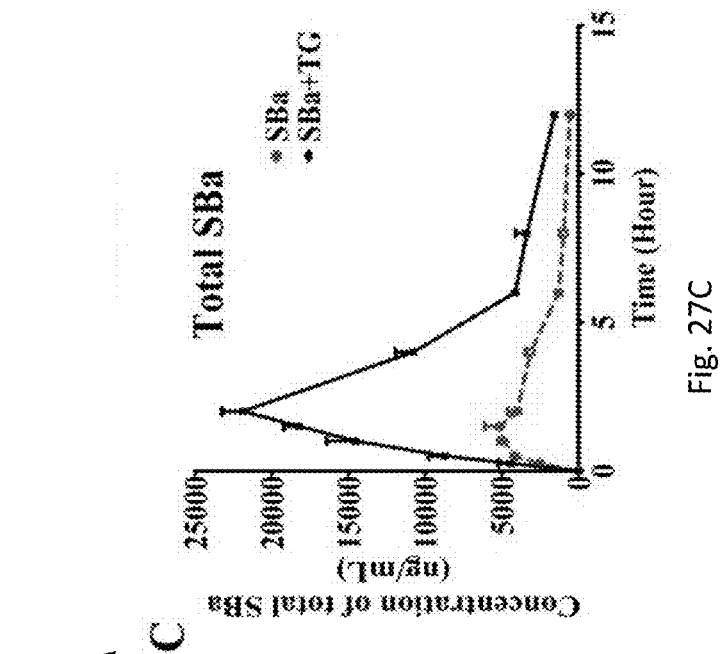
FIG. 27C illustrates the mean plasma concentration-time profile for 50 mg/kg silybin and in combination with 50 mg/kg tangeretin (TG) in accordance with an example embodiment.

FIG. 26 shows a table 2600 illustrating mean pharmacokinetic parameters of total silybin after oral administration at a dose of 50 mg/kg with or without simultaneous oral administration of 50 mg/kg tangeretin to rats.

FIGS. 27A, 27B, 27C and 27D show graphs 2700, 2710, 2720 and 2730 illustrating mean plasma concentration-time profiles of silybin in rats after a single oral administration dose of silybin (50 mg/kg) and in combination with tangeretin (50 mg/kg). (Each point represents the mean±SD of 6 rats). Significantly increased absorption were observed with co-administration of tangeretin for free silybin A (SBa, Figure A), free silybin B (SBb, Figure B), total silybin A (Figure C), and total silybin B (Figure D).

The mean plasma concentration-time profiles of silybin following oral administration (10 and 50 mg/kg) to rats in the presence or absence of tangeretin (10 or 50 mg/kg) were shown in FIGS. 24A-24D and 27A-27D, and the corresponding pharmacokinetic parameters calculated with non-compartmental analysis were shown in FIG. 22 and FIG. 25 for free silybin A and silybin B and FIG. 23 and FIG. 26 for total silybin A and silybin B, respectively. Tangeretin significantly altered the pharmacokinetic parameters of silybin. Compared to those in the oral control group (given silybin alone), AUC(0-t) of silybin (10 mg/kg) co-administration with tangeretin (10 mg/kg) significantly increased by 3.11-fold for free SBa, 3.40-fold for free SBb, 2.26-fold for total SBa, 1.45-fold for total SBb; and the peak plasma concentration (C(max)) was significantly increased by 6.47-fold for free SBa, 6.69-fold for free SBb, 2.65-fold for total SBa, 1.79-fold for total SBb, respectively.

Compared to those given silybin alone, the AUC(0-t) of silybin (50 mg/kg) in co-administration with tangeretin (50 mg/kg) significantly increased by 1.80-fold for free SBa, 1.47-fold for free SBb, 3.63-fold for total SBa, and 2.68-fold for total SBb; and the C(max) significantly increased by 1.46-fold for free SBa, 1.62-fold for free SBb, 3.60-fold for total SBa, and 3.20-fold for total SBb, respectively. However, there was no significant change in the t1/2, Tmax and clearance CLz/F (l/h/kg) of silybin in the presence of tangeretin. Additionally, there were no changes in the pharmacokinetic parameters of tangeretin (data not shown) in the absence or presence of silybin. Therefore, oral co-administration of tangeretin increased the plasma concentrations of silybin as well as its conjugates, indicating enhanced bioavailability of silybin in vivo. Moreover, we noticed that both tangeretin and baicalein at dosage of 10 mg/kg can effectively increase the absorption of 10 mg/kg of silybin in rat, which is more effective than that of 50 mg/kg dosage of tangeretin or baicalein.

Example 10: Hepatoprotective Effects of Silybin on CCl$_4$-Induced Acute Liver Injury The preventive and therapeutic effects of silybin on acute liver injury produced by carbon tetrachloride (CCl$_4$) in rats were further studied in the presence of tangeretin to demonstrate the enhanced activities associated with increased absorption of silybin in vivo.

FIG. 28 shows a table 2800 illustrating the effects of silybin co-administered with or without tangeretin on biochemical parameters in CCl$_4$-treated rats (n=6).

Figure 29:
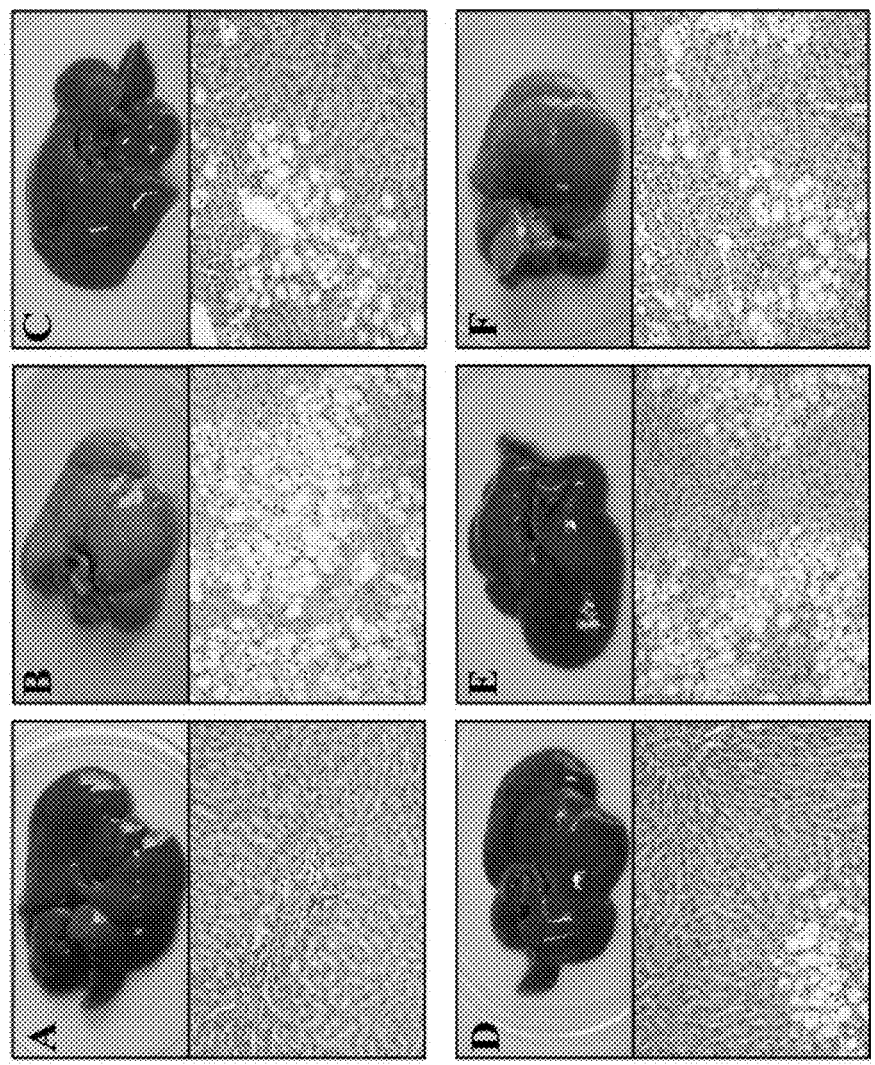
FIG. 29 illustrates the effects of silybin co-administered with tangeretin on the histopathological changes of $CCl_4$-induced acute liver injury in accordance with an example embodiment.
Figures 30A, 30B:
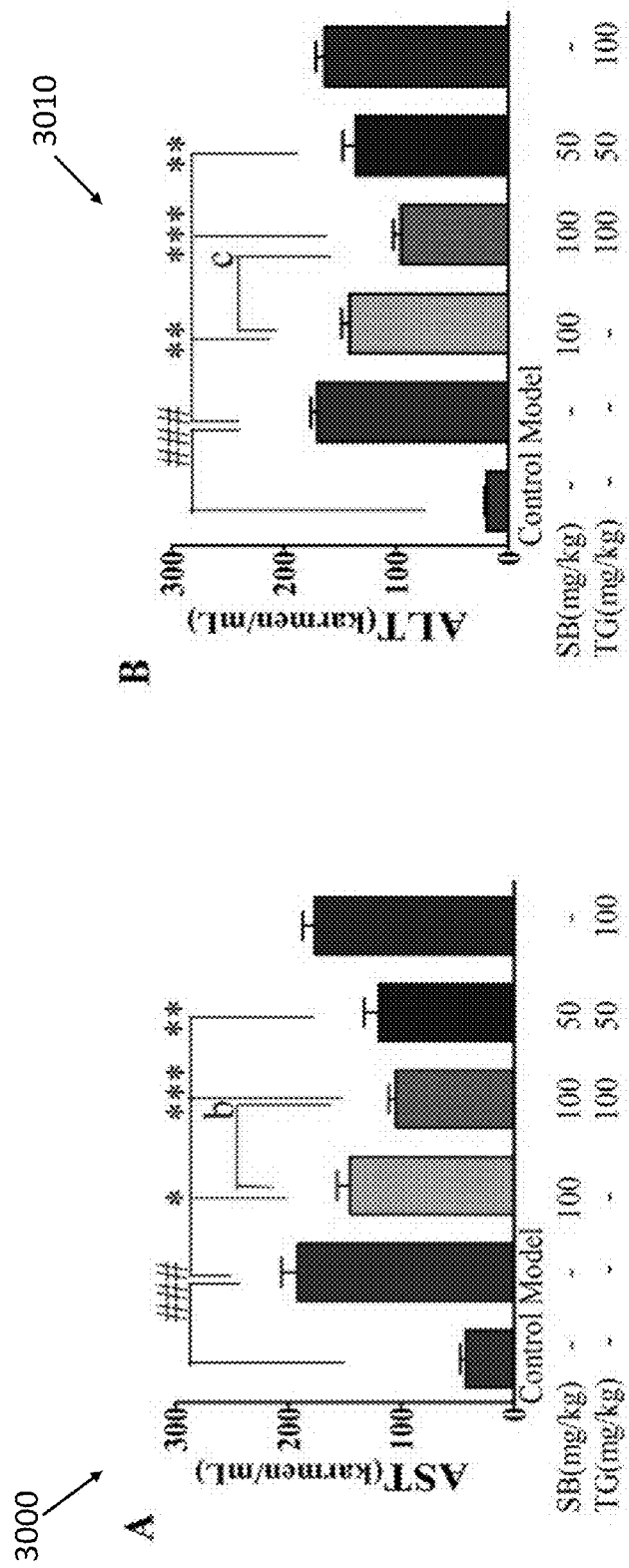
FIG. 30A illustrates the effect of silybin co-administered with or without tangeretin (TG) on the liver function index aspartate aminotransferase (AST) in the liver tissue of $CCl_4$-induced liver damage rats in accordance with an example embodiment.
FIG. 30B illustrates the effect of silybin co-administered with or without tangeretin (TG) on the liver function index alanine aminotransferase (ALT) in the liver tissue of $CCl_4$-induced liver damage rats in accordance with an example embodiment.
Figure 30D:
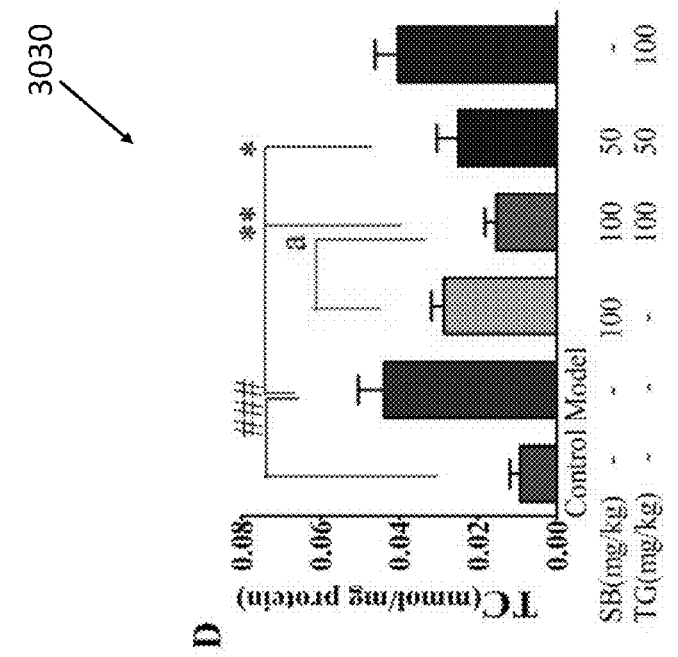
FIG. 30D illustrates the effect of silybin co-administered with or without tangeretin (TG) on the liver function index total cholesterol (TC) in the liver tissue of $CCl_4$-induced liver damage rats in accordance with an example embodiment.
Figure 30C:
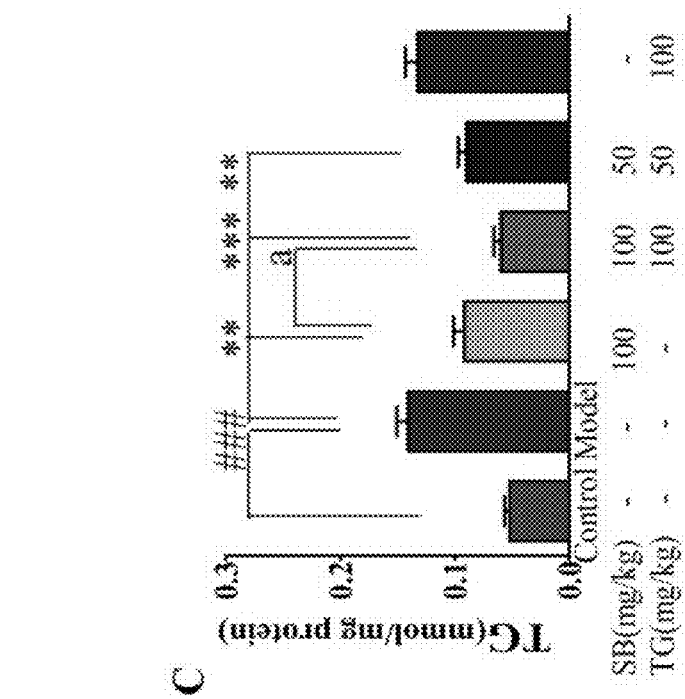
FIG. 30C illustrates the effect of silybin co-administered with or without tangeretin (TG) on the liver function index triglyceride (TG) in the liver tissue of $CCl_4$-induced liver damage rats in accordance with an example embodiment.
Figure 30F:
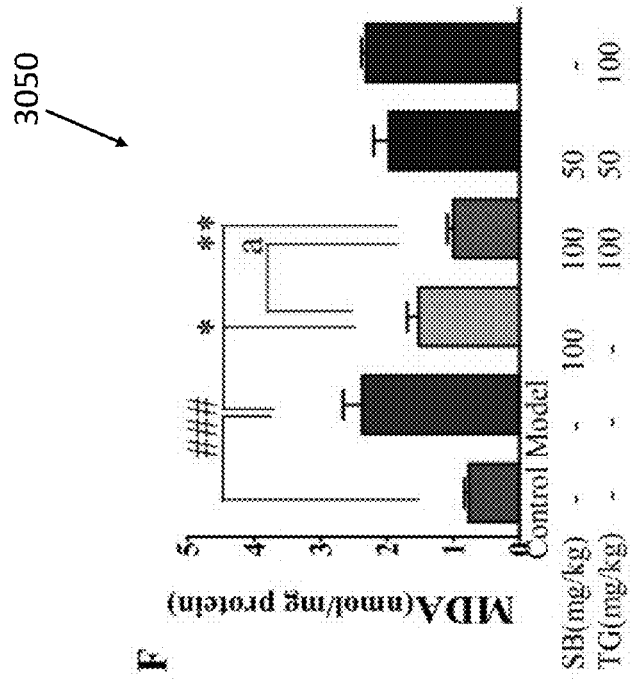
FIG. 30F illustrates the effect of silybin co-administered with or without tangeretin (TG) on the liver function index malondialdehyde (MDA) in the liver tissue of $CCl_4$-induced liver damage rats in accordance with an example embodiment.
Figure 30E:
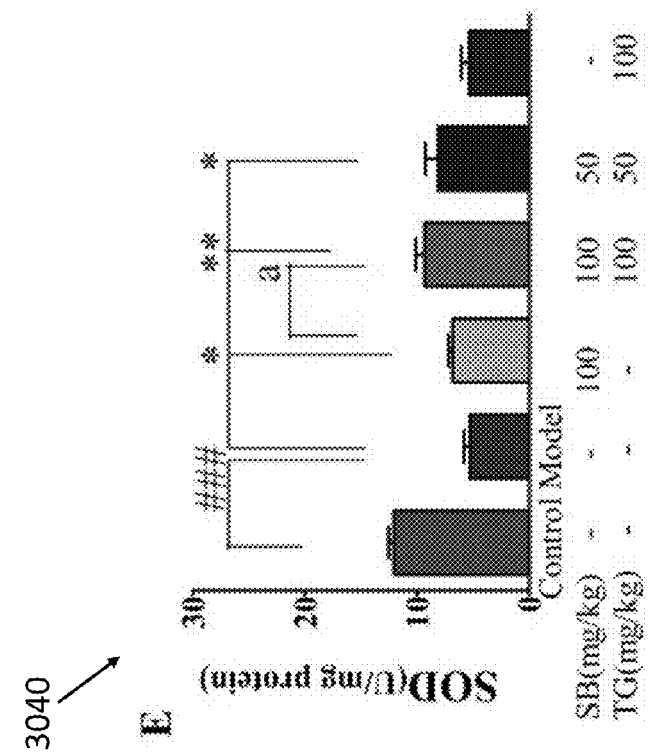
FIG. 30E illustrates the effect of silybin co-administered with or without tangeretin (TG) on the liver function index superoxide dismutase (SOD) in the liver tissue of $CCl_4$-induced liver damage rats in accordance with an example embodiment.
Figures 30G, 30H:
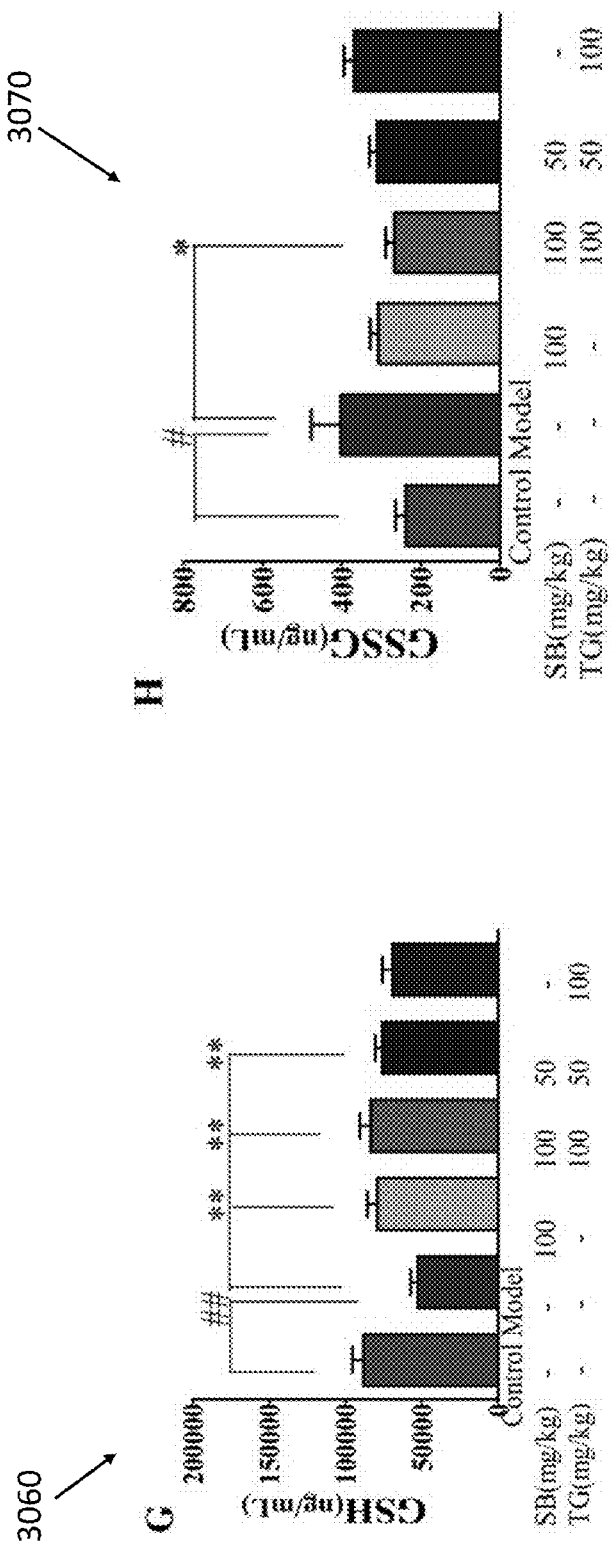
FIG. 30G illustrates the effect of silybin co-administered with or without tangeretin (TG) on the liver function index reduced glutathione (GSH) in the liver tissue of $CCl_4$-induced liver damage rats in accordance with an example embodiment.
FIG. 30H illustrates the effect of silybin co-administered with or without tangeretin (TG) on the liver function index oxidized glutathione (GSSG) in the liver tissue of $CCl_4$-induced liver damage rats in accordance with an example embodiment.
Figure 30I:
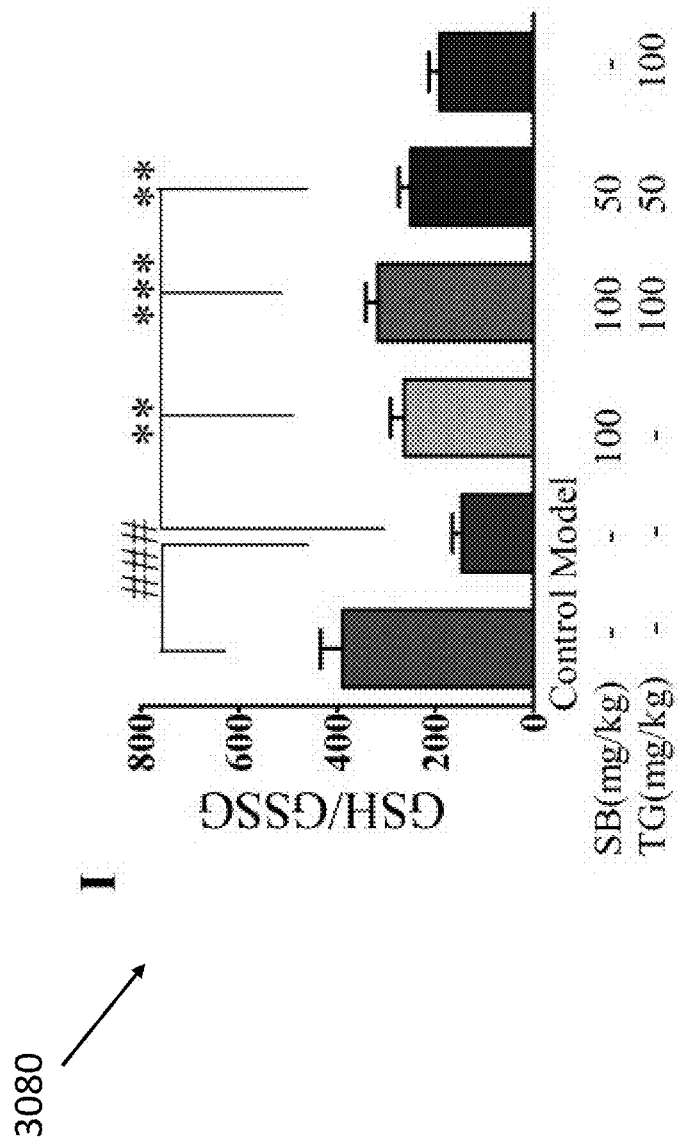
FIG. 30I illustrates the effect of silybin co-administered with or without tangeretin (TG) on the liver function index reduced glutathione/oxidized glutathione (GSH/GSSG) in the liver tissue of $CCl_4$-induced liver damage rats in accordance with an example embodiment.
Figures 31A, 31B:
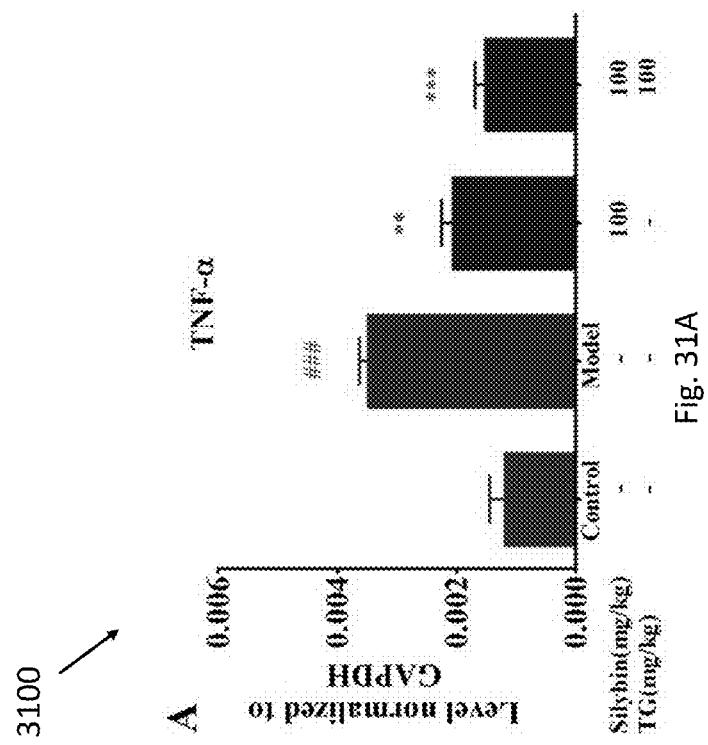
FIG. 31A illustrates the verification of tumor necrosis factor alpha (TNF-α) in livers from acute liver injury rat model in accordance with an example embodiment.
FIG. 31B illustrates the verification of interleukin-1beta (IL-1β) in livers from acute liver injury rat model in accordance with an example embodiment.
Figures 31E, 31F:
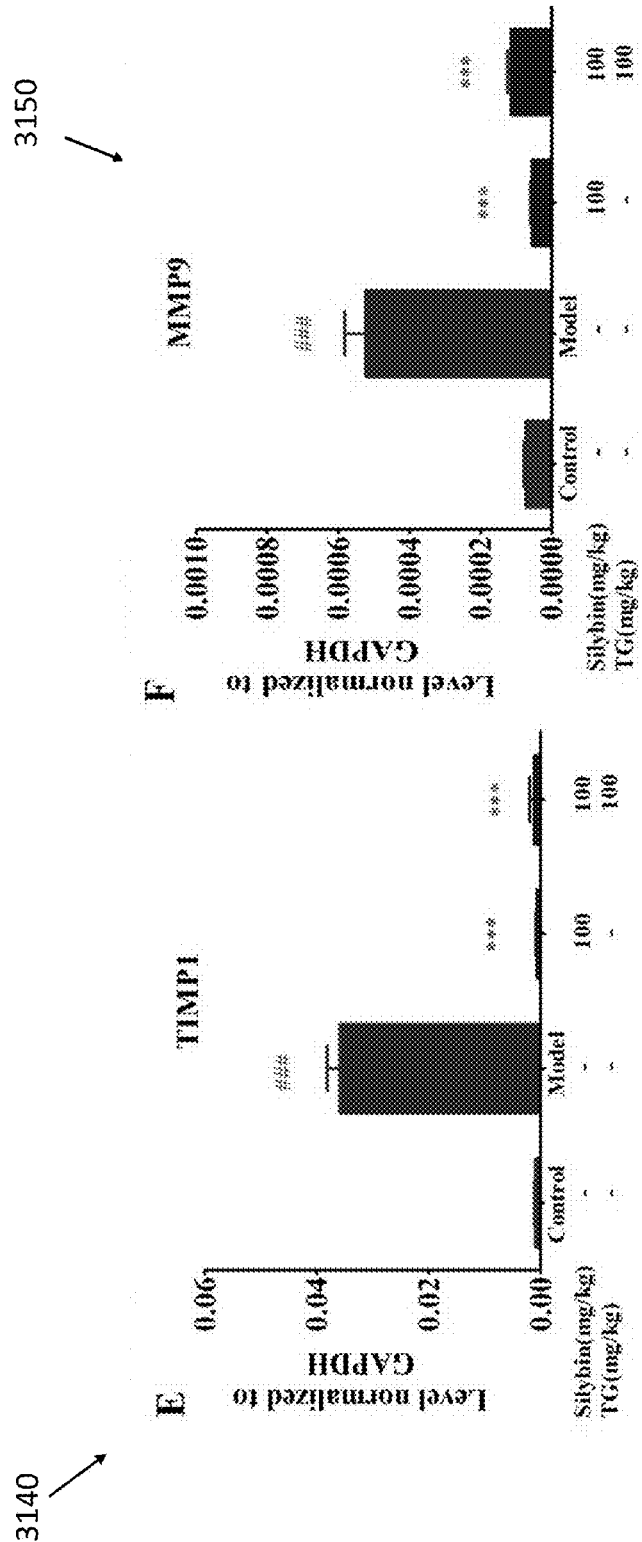
FIG. 31E illustrates the verification of TIMP metallopeptidase inhibitor 1 (TIMP1) in livers from acute liver injury rat model in accordance with an example embodiment.
FIG. 31F illustrates the verification of matrix metallopeptidase 9 (MMP9) in livers from acute liver injury rat model in accordance with an example embodiment.

FIG. 29 shows histopathological changes 2900 of silybin co-administered with tangeretin on CCl$_4$-induced acute liver injury. Representative hematoxylin and eosin (H&E) stained (×40) histopathological sections of the architecture of the liver from normal (A), vehicle-treated (B), pre-treatment with 100 mg/kg of silybin (C), pre-treatment with 100 mg/kg silybin in combination with 100 mg/kg tangeretin (D), pre-treatment with 50 mg/kg silybin in combination with 50 mg/kg tangeretin (E), and pre-treatment with 100 mg/kg of tangeretin (F) are shown (n=6).

FIGS. 30A, 30B, 30C, 30D, 30E, 30F and 30I show graphs 3000, 3010, 3020, 3030, 3040, 3050, 3060, 3070 and 3080 illustrating the effects of silybin (SB) co-administered with or without tangeretin (TG) on the liver function indexes including aspartate transaminase (AST), alanine aminotransferase (ALT), total cholesterol (TC), triglycerides (TG), malondialdehyde (MDA), reduced glutathione (GSH), oxidized glutathione (GSSG), ratio of reduced glutathione/oxidized glutathione GSH/GSSG in the liver tissue of CCl$_4$-induced liver damage rats. Values are expressed as means±S.E.M, n=6 in each group. * P<0.05, P<0.01, and * P<0.001 vs. model group; ###P<0.001 vs. control group; a P<0.05, (SB100 mg/kg+TG 100 mg/kg) group vs. SB 100 group FIGS. 31A, 31B, 31C, 31D, 31E and 31F show graphs 3100, 3110, 3120, 3130, 3140, 3150 illustrating the verification of different metabolites and enzymes in livers from acute liver injury rats model. *P<0.05 compared to Model group; **P<0.01 compared to Control group. #P<0.05, ##P<0.01, ###P<0.001 VS Control (Student's t test). SB:100 mg/kg; SB+TG: SB100 mg/kg+TG 100 mg/kg. (n=6).

Figure 32:
FIG. 32 illustrates the effect of silybin in combination with tangeretin (TG) on aspartate aminotransferase (AST), alanine aminotransferase (ALT), triglyceride (TG), total cholesterol (TC) and superoxide dismutase (SOD) index in $CCl_4$-induced liver injury rats in accordance with an example embodiment.
Figures 35A, 35B:
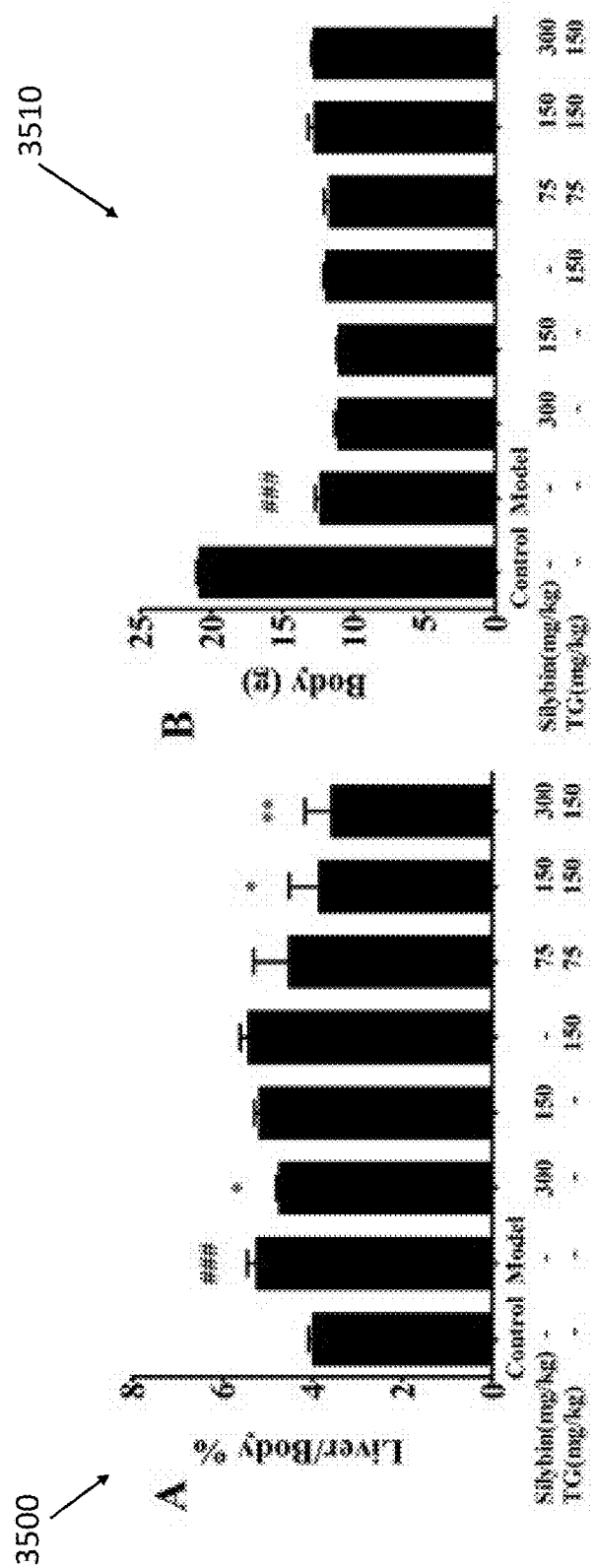
FIG. 35A illustrates the enhanced effect of silybin on the body weight of nonalcoholic steatohepatitis (NASH) mice model co-treated with tangeretin (TG) in accordance with an example embodiment.
FIG. 35B illustrates the enhanced effect of silybin on the body weight of nonalcoholic steatohepatitis (NASH) mice model co-treated with tangeretin (TG) in accordance with an example embodiment.
Figures 35C, 35D:
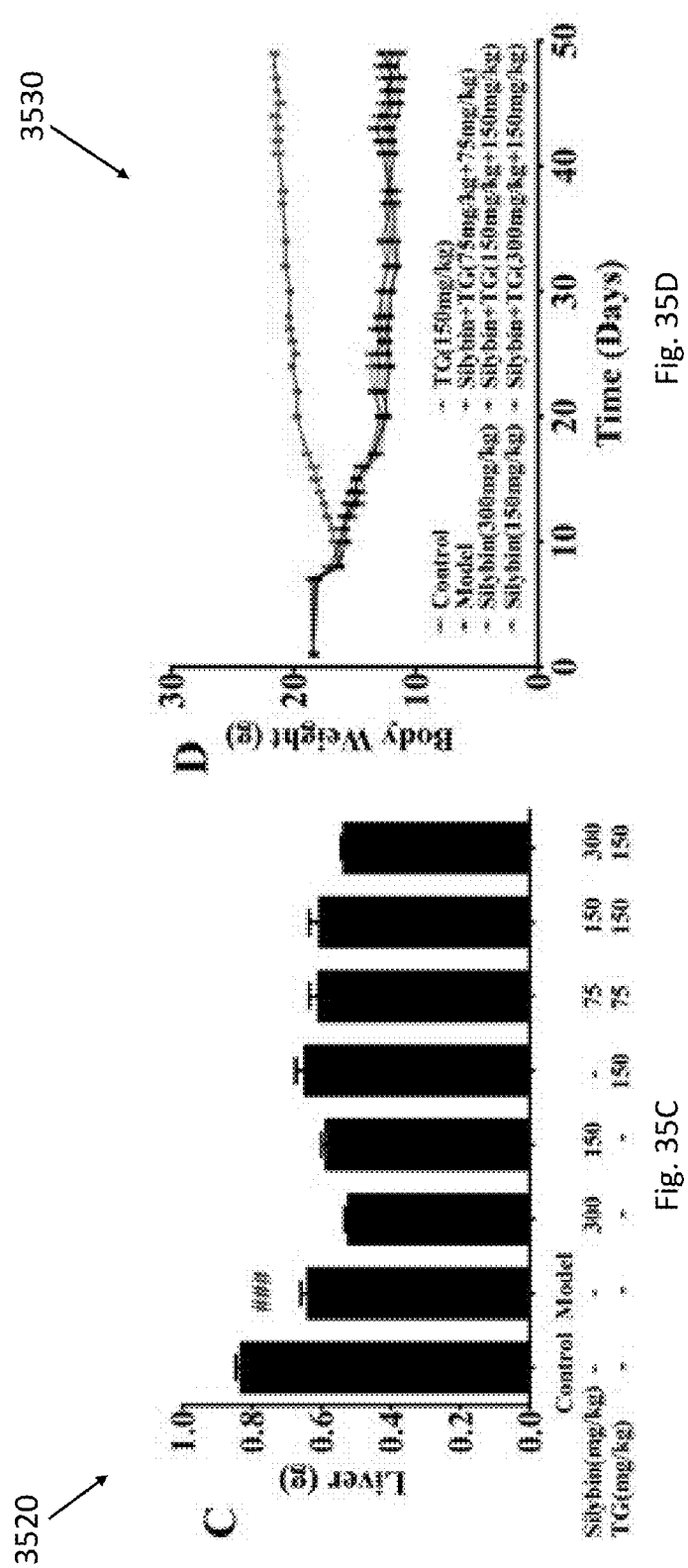
FIG. 35C illustrates the enhanced effect of silybin on the body weight of nonalcoholic steatohepatitis (NASH) mice model co-treated with tangeretin (TG) in accordance with an example embodiment.
FIG. 35D illustrates the enhanced effect of silybin on the body weight of nonalcoholic steatohepatitis (NASH) mice model co-treated with tangeretin (TG) in accordance with an example embodiment.
Figure 35E:
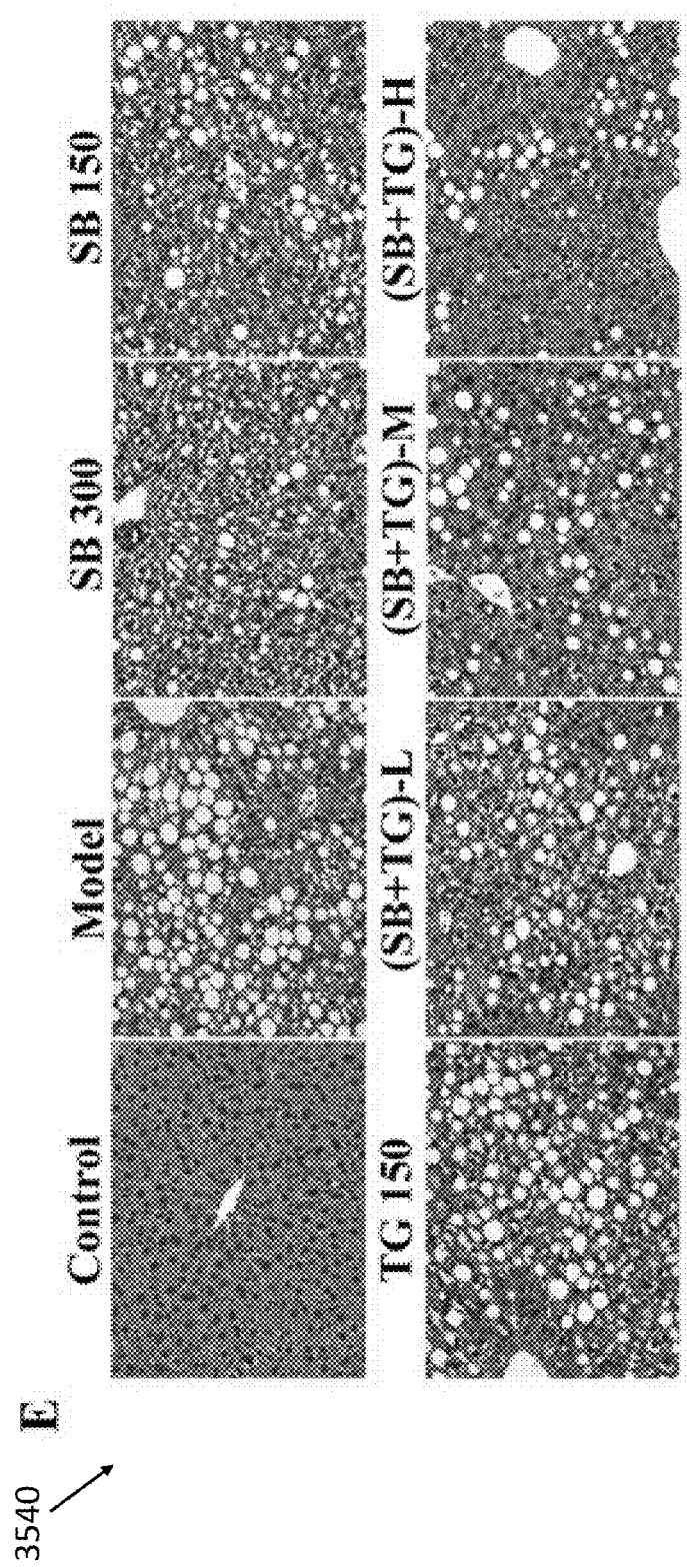
FIG. 35E illustrates the enhanced effect of silybin on the liver histologic lesions of nonalcoholic steatohepatitis (NASH) mice model co-treated with tangeretin (TG) in accordance with an example embodiment.
Figures 36A, 36B:
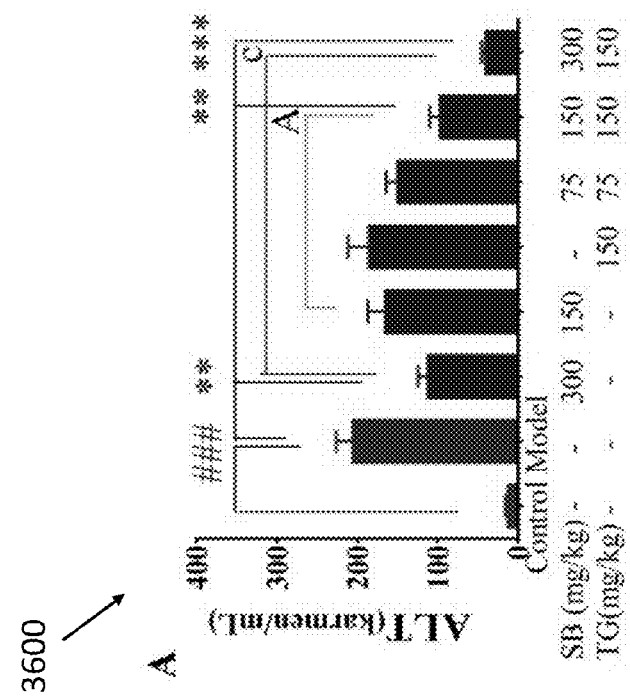
FIG. 36A illustrates the enhanced protective effect of silybin on liver function index alanine aminotransferase (ALT) levels by co-treatment with tangeretin (TG) in methionine choline-deficient (MCD)-induced nonalcoholic steatohepatitis (NASH) mouse model in accordance with an example embodiment.
FIG. 36B illustrates the enhanced protective effect of silybin on liver function index aspartate aminotransferase (AST) levels by co-treatment with tangeretin (TG) in methionine choline-deficient (MCD)-induced nonalcoholic steatohepatitis (NASH) mouse model in accordance with an example embodiment.
Figure 36D:
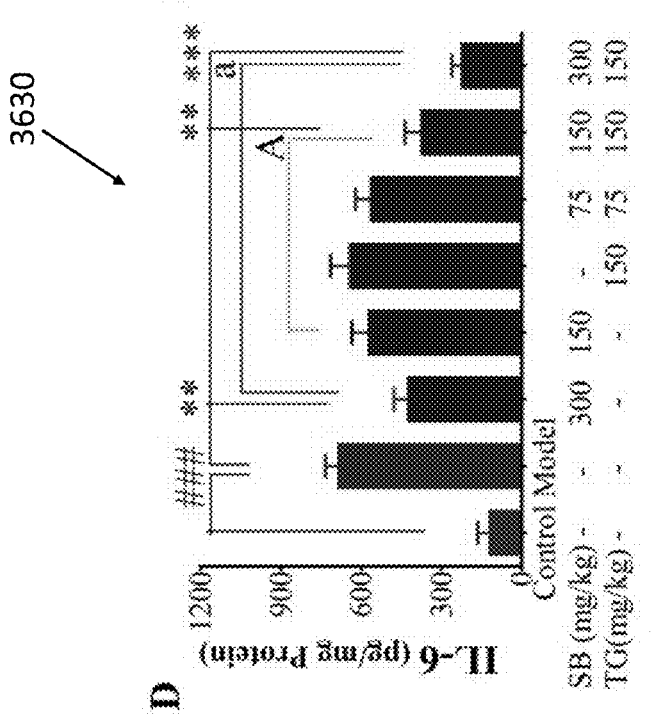
FIG. 36D illustrates the enhanced protective effect of silybin on liver function index interleukin-6 (IL-6) levels by co-treatment with tangeretin (TG) in methionine choline-deficient (MCD)-induced nonalcoholic steatohepatitis (NASH) mouse model in accordance with an example embodiment.
Figure 36C:
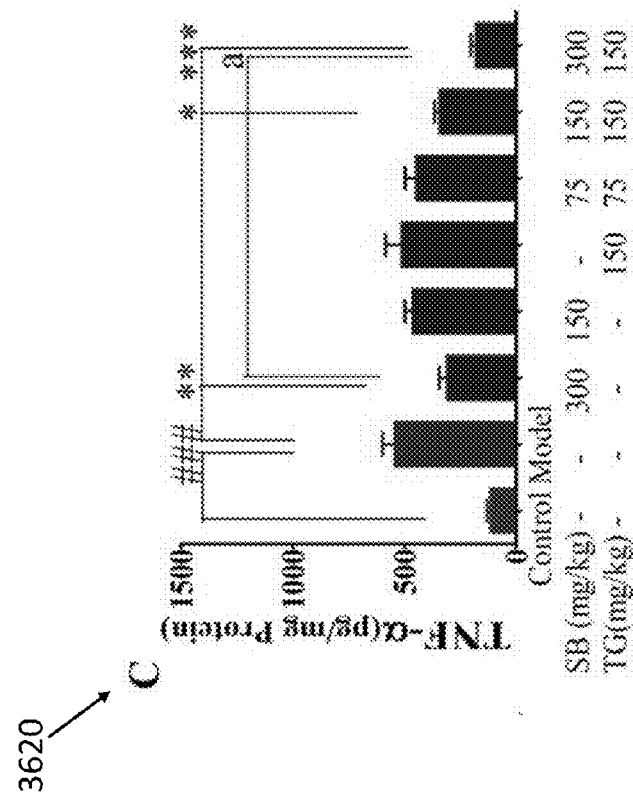
FIG. 36C illustrates the enhanced protective effect of silybin on liver function index tumor necrosis factor-α (TNF-α) levels by co-treatment with tangeretin (TG) in methionine choline-deficient (MCD)-induced nonalcoholic steatohepatitis (NASH) mouse model in accordance with an example embodiment.
Figures 36E, 36F:
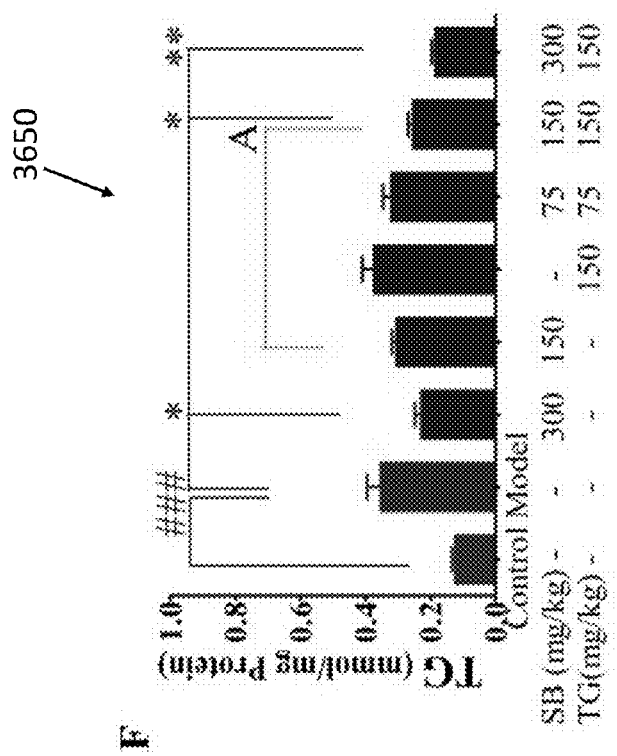
FIG. 36E illustrates the enhanced protective effect of silybin on liver function index total cholesterol (TC) levels by co-treatment with tangeretin (TG) in methionine choline-deficient (MCD)-induced nonalcoholic steatohepatitis (NASH) mouse model in accordance with an example embodiment.
FIG. 36F illustrates the enhanced protective effect of silybin on liver function index triglyceride (TG) levels by co-treatment with tangeretin (TG) in methionine choline-deficient (MCD)-induced nonalcoholic steatohepatitis (NASH) mouse model in accordance with an example embodiment.
Figure 36I:
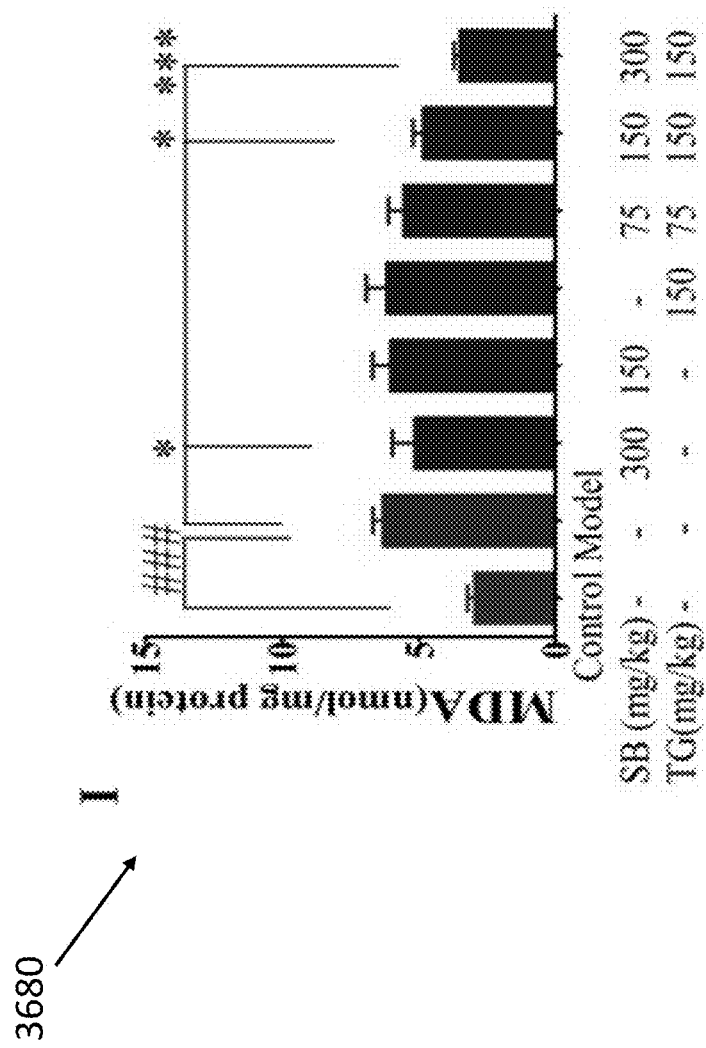
FIG. 36I illustrates the enhanced protective effect of silybin on liver function index by co-treatment with tangeretin (TG) in methionine choline-deficient (MCD)-induced nonalcoholic steatohepatitis (NASH) mouse model in accordance with an example embodiment.

FIG. 32 shows a table 3200 illustrating the effect of silybin in combination with tangeretin on AST, ALT, TC, TG and superoxide dismutase (SOD) index in CCl$_4$-induced liver injury rats. (Mean±SD, n=6).

FIG. 33 shows a table 3300 illustrating semi-quantitative histopathological changes of CCl$_4$-induced acute liver injury in rats with different treatment by using slides stained with H&E.

The body and liver weight as well as the liver to body weight ratio of the rats after treatments are shown in FIG. 28. The liver weight and liver to body weight ratio were significantly elevated 24 hours after CCl$_4$-induced toxic liver injury, while this increase was negated in silybin-treated and silybin-tangeretin-treated groups (p<0.05). The livers of CCl$_4$-treated rats appeared larger and with a pale and irregular surface indicative of severe hepatocellular damage as shown in FIG. 29. Moreover, apparent liver injuries, which were characterized by large areas of necrotic tissue, severe loss of hepatic architecture and a significant number of ballooning hepatocytes were observed in CCl$_4$-treated rats with histopathological analysis of liver sections stained with hematoxylin and eosin (H & E), which was less prominent in silybin-treated animals (FIG. 29C). However, CCl$_4$-induced macroscopic and histopathological changes (FIG. 29B) were significantly attenuated in silybin-tangeretin-treated animals (FIGS. 29D and 29E).

Liver injury in the CCl$_4$-treated group compared to the control group was also reflected by a marked increase in serum transaminases which were released into the blood once the structural integrity of the hepatocyte was damaged. As shown in FIGS. 30A-30I, after acute CCl$_4$ challenge, the serum levels of ALT and AST in CCl$_4$-treated group increased 5 to 6 times, respectively, over those in the normal control group. However, pre-administration of silybin-treated at 100 mg/kg for seven consecutive days significantly prevented the CCl$_4$-induced increase of serum activity of ALT and AST. Similarly, 100 mg/kg of silybin significantly (p<0.01) attenuated increases in the serum TG, and TC levels. However, combination treatment of silybin-tangeretin showed a better hepatoprotective effect than single silybin treatment at the same dosage.

The antioxidant properties of silybin are considered to be responsible for its protective actions. The hepatic level of malondialdehyde (MDA) and the activity of the antioxidant enzymes superoxide dismutase (SOD) as well as the ratio of GSH/GSSG were assessed as indicators of oxidative stress in CCl$_4$-induced liver injury rats. As shown in FIGS. 30A-30I, CCl$_4$ exposure induced a remarkable increase in hepatic MDA production by 162.5% (0.88±0.09 versus 2.31±0.32, p<0.001), and a remarkable decrease in hepatic activities of SOD level by 128.28% (12.10±1.13 versus 5.30±1.32, p<0.001), of those of the control group. This increase of MDA and depletion of endogenous antioxidants was markedly ameliorated in silybin-tangeretin treated group. As a radical scavenger, GSH can be oxidized to GSSG under oxidative stress. Hence, GSH/GSSG ratio has been also used as a marker of oxidative stress. CCl$_4$ exposure significantly increased the GSSG level in the liver, leading to a great decrease in GSH/GSSG ratio; these changes were remarkably ameliorated in silybin-tangeretin treated rats.

Inflammatory mediators from Kupffer cells have been proved to play a pivotal role in hematopoietic stem cell (HSC) activation and fibrogenesis. In response to liver damage caused by CCl$_4$, pro-inflammatory factors such as tumor necrosis factor alpha (TNF-α), interleukin-1beta (IL-1β), interleukin 6 (IL-6), and interleukin 17 (IL-17) were upregulated in liver. Quantitative reverse transcription polymerase chain reaction (RT-PCR) analysis revealed a strong suppression of pro-inflammatory response in combined group with silybin and tangeretin as compared with silybin alone after treatment of CCl$_4$ (FIG. 31A-31F). Similarly, the hepatic expression of profibrotic molecules TIMP metallopeptidase inhibitor 1 (TIMP1) as well as matrix metallopeptidase 9 (MMP9) was also down-regulated in combined group (FIG. 31A-31F).

Example 11: Effects of Silybin on Methionine-Choline Deficient (MCD) Diet-Induced Nonalcoholic Steatohepatitis (NASH)

MCD diet-induced NASH in BALB/c mice by feeding for 8 weeks was applied to further demonstrate the bioenhancer effect of tangeretin along with enhanced pharmacokinetic activity.

FIG. 34 shows a table 3400 illustrating characteristics of C57BL/6 mice fed with MCS diet, MCD diet, and MCD diet with silybin only or co-treatment with tangeretin.

FIGS. 35A, 35B, 35C, 35D and 35E show graphs 3500, 3510, 3520, 3530 and photomicrographs 3540 illustrating the enhanced effects of silybin on the body weight and the liver histological lesions of NASH mice model co-treated with tangeretin. Silybin significantly decreased liver/body ratio (A) by co-treatment with tangeretin, but did not significantly affect the body weight (B) and liver weight (C) as well as the body weight curve recorded from day 0 to day 49. The photomicrographs of liver sections stained with routine hematoxylin and eosin (H&E) (×200) are shown in figure E (E) after 8 weeks of administration with MCD diet as well as different treatments. SB 300: orally given silybin 300 mg/kg; SB 150: orally given silybin 150 mg/kg; TG150: orally given tangeretin 150 mg/kg; (SB+TG)-L: orally given silybin 75 mg/kg and tangeretin 75 mg/kg; (SB+TG)-M: orally given silybin 150 mg/kg and tangeretin 150 mg/kg; (SB+TG)-H: orally given silybin 300 mg/kg and tangeretin 300 mg/kg (*, P<0.05; **, P<0.01; vs. model group, ###P<0.001 vs. control group).

FIGS. 36A, 36B, 36C, 36D, 36E, 36F, 36G, 36H and 36I show graphs 3600, 3610, 3620, 3630, 3640, 3650, 3660, 3670 and 3680 illustrating the enhanced protection effects of silybin on liver function index including AST, ALT, TNF-α, IL-6, TC, TG and SOD levels by co-treatment with tangeretin in MCD-induced mice NASH model. Statistically significant differences with respect to the control are expressed as ###P<0.001; statistically significant differences with respect to the model are expressed as * P<0.05, P<0.01, and * P<0.001; statistically significant differences with respect to the silybin (300 mg/kg) group are expressed as a P<0.05, b P<0.01, and c P<0.001). n=6-8 in each group.

FIG. 37 shows a table 3700 illustrating the effect of treatment with silybin with or without tangeretin on biochemical parameters in mice fed with MCD diet (Means±SEM, n=6-8).

FIG. 38 shows a table 3800 illustrating semi-quantitative evaluation of liver damage in mice of different treatment groups using slides stained with H&E.

As shown in FIG. 34 and FIGS. 35A-35E, eight weeks of MCD diet feeding dramatically decreased body weight and liver weight (P<0.001, P<0.001) but increased liver/body weight ratio (P<0.01), while silybin and silybin-tangeretin combined treatment slightly increased body weight but caused a moderate decrease in the liver/body weight ratio.

As hepatic histopathology analysis is the gold standard in NASH diagnosis, the MCD diet induced marked lipid accumulation with inflammatory cell infiltration in the liver, hepatocyte death, and liver fibrosis (FIGS. 35A-35E). The results of semi-quantitative evaluation of liver damage based on H&E staining showed MCD diet led to elevated scores for steatosis, ballooning and inflammation indicating steatohepatitis (FIG. 38). However, lipid accumulation and inflammatory infiltration were decreased in the silybin or silybin-tangeretin treated mice. The serum biomarker levels of NASH are shown in FIG. 37. Similarly, there were significant increases in total cholesterol (TC) and triglyceride (TG) levels in MCD-fed mice compared with control mice (MCS diet group), while silybin or silybin-tangeretin administration clearly inhibited MCD diet-induced TC and TG increase (FIG. 34).

Higher levels of serum ALT (FIG. 36A) and AST (FIG. 36B) which are the hepatocellular injury markers were observed in the MCD-fed group than that of the control group. Similar trend was observed for the higher level of oxidative stress markers including MDA, SOD, GSH and GSH/GSSG ratio. Silybin (300 mg/kg) and silybin-tangeretin treatment suppressed MCD diet-induced elevation of ALT, AST, MDA, SOD, GSH and GSH/GSSG ratio.

Hepatic inflammation plays an important role in the progression of hepatic steatosis to hepatic fibrosis and cirrhosis. Hence, serum inflammatory cytokines levels were also evaluated. The levels of IL-1β, TNF-α and IL-6 were significantly increased in the liver of MCD-fed mice than that of the control mice, consistent with hepatic biochemistry and histopathology results. Additionally, silybin treatment in the absence or presence of tangeretin suppressed MCD diet-induced cytokines elevation.

The results show that silybin or combination therapy of silybin with tangeretin can attenuate hepatocyte lipid accumulation and inflammation in MCD-induced NASH, but that combination treatment of silybin-tangeretin shows a better therapeutic effect than single silybin treatment at the same dosage, which may correlate with the enhanced bioavailability of silybin.

Figure 39:
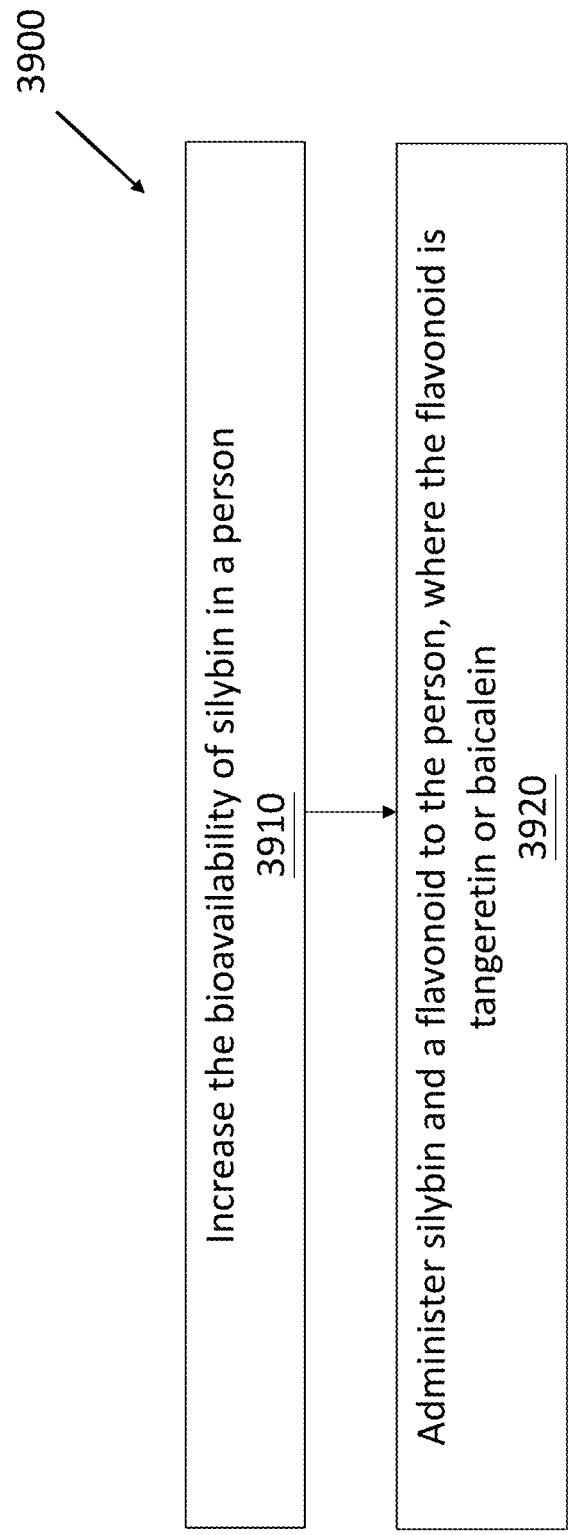

FIG. 39 is a flowchart 3900 illustrating a method to increase the bioavailability of silybin in a person in accordance with an example embodiment.

Block 3910 states increase the bioavailability of silybin in a person. In an example embodiment, silybin has low bioavailability after undergoing rapid first-pass metabolism following oral administration.

Block 3920 states administer silybin and a flavonoid to the person, where the flavonoid is tangeretin or baicalein. In an example embodiment, the silybin and flavonoid are administered to the person simultaneously or sequentially.

Figure 40:
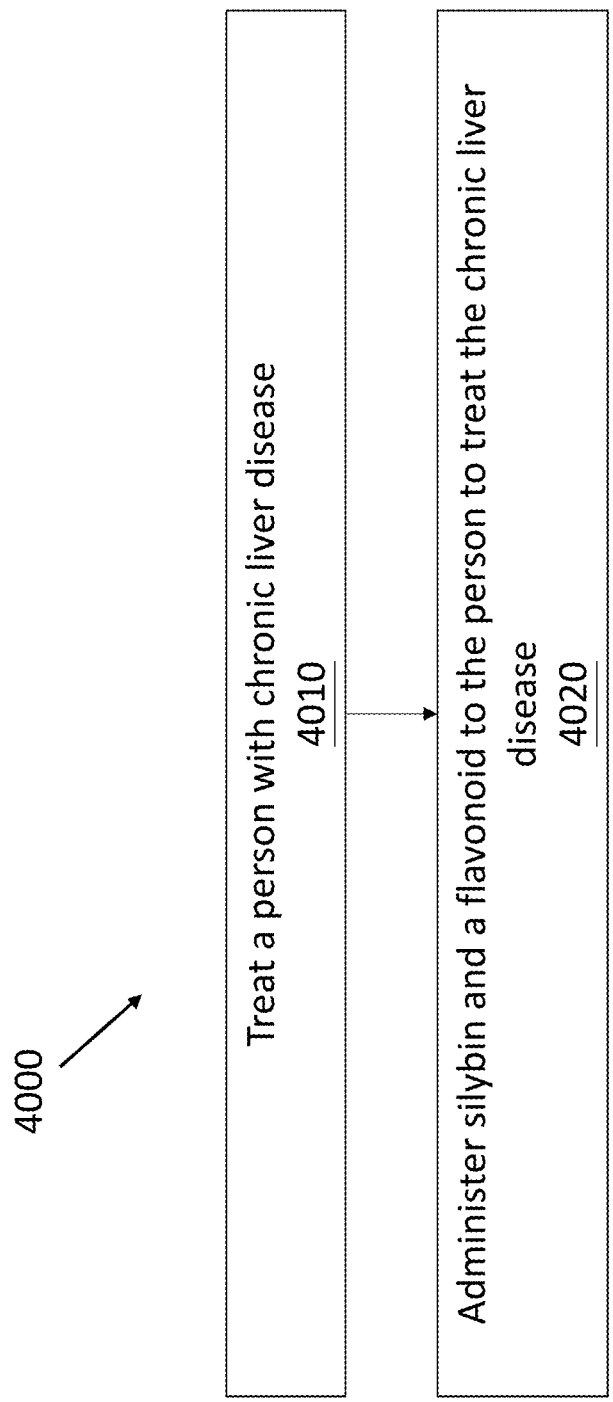

FIG. 40 is a flowchart 4000 illustrating a method to treat chronic liver disease in a person in accordance with an example embodiment.

Block 4010 states treat a person with chronic liver disease. In one example embodiment, silybin is a herbal medicine used in the treatment of chronic liver disease.

Block 4020 states administer silybin and a flavonoid to the person to treat the chronic liver disease. In an example embodiment, the silybin and flavonoid are administered to the person orally.

As used herein, the term "administration" or "administering" refers to providing a compound of an example embodiment and/or prodrugs thereof to a person in need of treatment.

As used herein, the term "simultaneously", "administered simultaneously" or "provided simultaneously" refers to two or more substances administered at the same point in time or immediately following one another. In the latter case, the two or more substances are administered at times sufficiently close that the results observed are indistinguishable from those achieved when the substances are administered at the same point in time.

As used herein, the term "sequentially", "administered sequentially" or "provided sequentially" refers to a first substance administered before one or more subsequently administered substance, or means that a first substance binds to MRP2 or BCRP in the liver before the one or more administered substance is released in the liver. In an example embodiment, the first substance is administered 10 minutes, 20 minutes, 30 minutes or 45 minutes before the subsequently administered substance. In an example embodiment, the first substance is administered 1 hour, 2 hours or 3 hours before the other substance.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

What is claimed is:

1. A method of treating chronic liver disease in a patient in need thereof, comprising:
   administering to the patient a flavonoid and silybin to treat the chronic liver disease,
   wherein the flavonoid is tangeretin, and
   wherein the flavonoid inhibits a function of efflux transporters multidrug resistance-associated protein 2 (MRP2) and breast cancer resistance protein (BCRP) such that a plasma concentration of the silybin is increased.

2. The method of claim 1, wherein the silybin and the flavonoid are administered to the patient simultaneously.

3. The method of claim 1, wherein the silybin and the flavonoid are each administered to the patient sequentially.

4. The method of claim 1, wherein the flavonoid increases bioavailability of the silybin in the patient such that the chronic liver disease is treated.

5. The method of claim 1, wherein the flavonoid is administered to the patient prior to administration of the silybin.

6. The method of claim 1, wherein the silybin and the flavonoid are administered to the patient orally.

7. A method of treating chronic liver disease in a patient in need thereof, comprising:
   administering to the patient a combination of flavonoid and silybin,
   wherein the flavonoid increases bioavailability of the silybin in the patient such that the combination of the flavonoid and the silybin shows a better therapeutic effect in treating the chronic liver disease than single silybin does, and the flavonoid is tangeretin, and
   wherein the flavonoid inhibits a function of efflux transporters multidrug resistance-associated protein 2 (MRP2) and breast cancer resistance protein (BCRP) such that a plasma concentration of the silybin is increased.

8. The method of claim 7, wherein the silybin and the flavonoid are administered at a ratio of 1:1 by weight.

9. The method of claim 7, wherein the silybin comprises silybin A and silybin B, and the silybin A accounts for 40%-70% of the silybin by weight.

10. The method of claim 7, wherein the silybin consists of silybin A and silybin B, and each of the silybin A and the silybin B accounts for 50% of the silybin by weight.

11. The method of claim 7, wherein the silybin and the flavonoid are administered to the patient simultaneously.

12. The method of claim 7, wherein the silybin and the flavonoid are administered to the patient orally.

* * * * *